(12) United States Patent
Ripin et al.

(10) Patent No.: US 6,403,776 B1
(45) Date of Patent: Jun. 11, 2002

(54) SYNTHESIS OF CARBAMATE KETOLIDE ANTIBIOTICS

(75) Inventors: David H. B. Ripin, Westbrook; Brian C. Vanderplas, Old Lyme; Takushi Kaneko, Guilford, all of CT (US); William T. McMillen, Fisher, IN (US); Robert W. McLaughlin, Groton, CT (US)

(73) Assignee: Pfizer Inc., New York, NY (US)

( * ) Notice: Subject to any disclaimer, the term of this patent is extended or adjusted under 35 U.S.C. 154(b) by 22 days.

(21) Appl. No.: 09/610,057

(22) Filed: Jul. 5, 2000

(51) Int. Cl.$^7$ .................................................. C07H 1/00
(52) U.S. Cl. ........................................ 536/7.4; 536/18.5
(58) Field of Search ................................. 536/7.4, 18.5

(56) References Cited

U.S. PATENT DOCUMENTS

| | | | |
|---|---|---|---|
| 4,474,768 A | 10/1984 | Bright | |
| 4,517,359 A | 5/1985 | Kobrehel | |
| 5,747,466 A | * 5/1998 | Elliott et al. | .................. 514/29 |

FOREIGN PATENT DOCUMENTS

WO         9856800         12/1998

* cited by examiner

*Primary Examiner*—Elli Peselev
(74) *Attorney, Agent, or Firm*—Peter C. Richardson; Paul G. Ginsburg; Jolene W. Applemen

(57) ABSTRACT

The invention relates to a method of preparing a macrolide antibiotic of the formula (15)

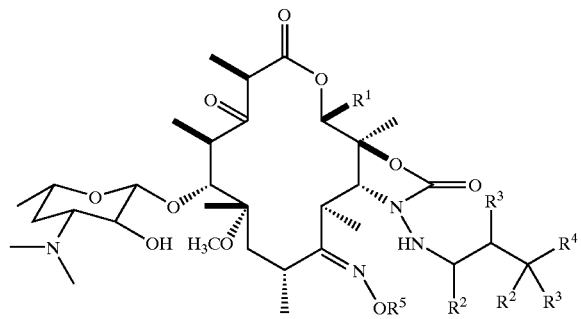

wherein $R^1$, $R^2$, $R^3$, $R^4$, $R^5$ are defined above. These antibiotics are useful as antibacterial and antiprotozoal agents in mammals, including man, as well as in fish and birds. The invention also includes novel compounds made by the preparation of the macrolide antibiotic.

66 Claims, No Drawings

SYNTHESIS OF CARBAMATE KETOLIDE ANTIBIOTICS

This invention relates to a preparation of macrolide antibiotics that are useful as antibacterial and antiprotozoal agents in mammals, including man, as well as in fish and birds.

Macrolide antibiotics are known to be useful in the treatment of a broad spectrum of bacterial and protozoal infections in mammals, fish and birds. Such antibiotics include various derivatives of erythromycin A such as azithromycin which is commercially available and is referred to in U.S. Pat. Nos. 4,474,768 and 4,517,359 both of which are incorporated herein by reference in their entirety. Other macrolide antibiotics are disclosed and claimed in PCT publication number WO 98/56800, published Dec. 17, 1998 which designates the United States, and U.S. Provisional Applications 60/111,728 and 60/101,263 all of which are incorporated herein by reference in their entirety. The new process as described below provides macrolide compounds that possess activity against various bacterial and protozoal infection.

SUMMARY OF THE INVENTION

The present invention relates to the process for preparing a compound of the formula

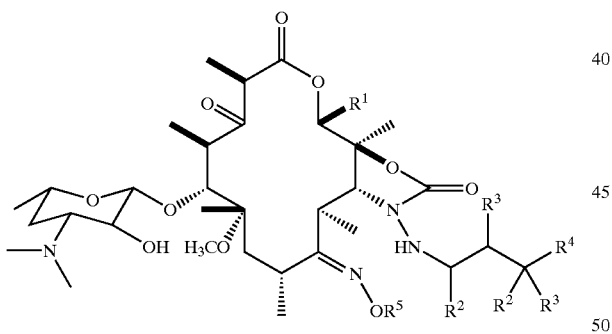

(15)

wherein:

$R^1$ is an alpha-branched $C_3$–$C_8$ alkyl, alkenyl, alkynyl, alkoxyalkyl or alkylthioalkyl group any of which may optionally be substituted by one to three hydroxyl groups; a ($C_5$–$C_8$ cycloalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally substituted with one to three groups independently selected from $C_1$–$C_4$ alkyl, $C_1$–$C_4$ alkoxy, $C_1$–$C_4$ alkylthio, halo, hydroxyl, trifluoromethyl, and cyano; or $R^1$ is formula (a) as shown below:

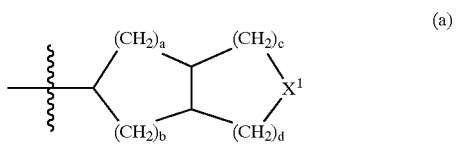

(a)

wherein $X^1$ is O, S or —$CH_2$—, a, b, c, and d are each independently selected from an integer ranging from 0 to 2 and a+b+c+d≦5; or $R^1$ is $CH_2R^{24}$, wherein $R^{24}$ is H, $C_1$–$C_8$alkyl, $C_2$–$C_8$alkenyl, $C_2$–$C_8$alkynyl, alkoxy alkylthioalkyl containing from 1 to 6 carbon atoms in each alkyl, alkylthio, alkylthio or alkoxy group wherein any of said alkyl, alkoxy, alkenyl or alkynyl groups may be substituted by one to three hydroxyl, or halo groups, or a $C_3$–$C_8$cycloalkyl or $C_5$–$C_8$cycloalkenyl either of which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and, each $R^2$ and $R^3$ is independently H or $C_1$–$C_6$ alkyl; and, each $R^4$ is independently $C_6$–$C_{10}$ aryl or 5 to 10 membered heterocycle, wherein said aryl and heterocycle groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, and —$S(O)_n(C_1$–$C_{10}$ alkyl) wherein n is an integer ranging from 0 to 2, and $SO_2NR^2R^3$; and $R^5$ is H or $C_1$–$C_{10}$ alkyl, wherein 1 to 3 carbons of said alkyl are optionally replaced by a heteroatom selected from O, S, and $NR^2$, and said alkyl group is optionally replaced by 1 to 3 substituents independantly selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n(C_1$–$C_{10}$ alkyl) wherein n is an integer ranging from 0 to 2, and $SO_2NR^2R^3$;

which comprises treating a compound of the formula

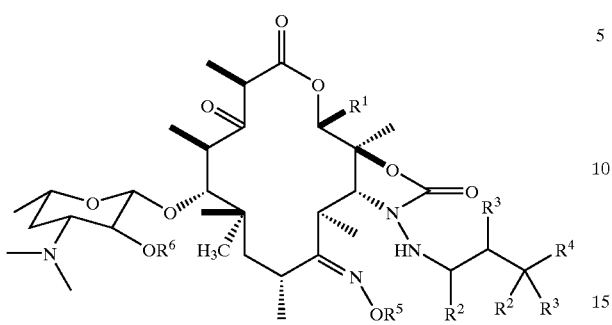

(14)

with a nucleophile or solvolysis to cleave the $R^6$ protecting group wherein:

$R^1$ to $R^5$ are as defined above; and $R^6$ is H, —C(O)$R^4$, or $C_1$–$C_{18}$ alkanoyl, wherein one or two carbons in the alkyl portion of said alkanoyl may be optionally replaced by a heteroatom selected from O, S, and $NR^2$.

In one embodiment the $R^6$ protecting group can be removed by solvolysis in an alcoholic or aqueous solvent with the optional addition of base to accelerate the reaction. In the process of preparing a compound of formula 15, examples of suitable alcoholic solvents include but are not limited to, methanol, ethanol, isopropanol and tert-butanol. Examples of bases include, but are not limited to, sodium carbonate, sodium bicarbonate, potassium carbonate, potassium hydroxide, sodium hydroxide, potassium fluoride and barium hydroxide.

In addition the $R^6$ protecting group can be removed with a nucleophile, including, but not limited to, ammonium hydroxide, monoalkyl amine, dialkyl-amine, alkane thiol or hydroxide. Useable solvents include, but are not limited to, water, methanol, ethanol, isopropanol, tertbutanol, dimethylformamide, N-methyl pyrrolidinone, acetonitrile, dimethyl acetamide, tetrahydrofuran, N-methylpyrrolidinone, acetonitrile, dimethylacetamide, tetrahydrofuran ethylacetate, and toluene. Preferably the deprotection is run in methanol with the addition of potassium carbonate at room temperature.

According to the invention compound 14 maybe prepared by the oxidation of a compound of the formula

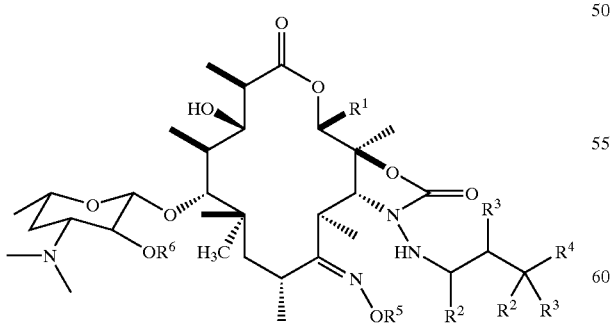

(13)

under Swern conditions wherein:

$R^1$ to $R^6$ are defined above.

Preferably, the Swern conditions are selected from the following:

(a) In an inert solvent including, but not limited to, dichloromethane, dichloroethane, and tetrachloroethane; dimethylsulfoxide is preactivated with activating agents including, but not limited to, oxalyl chloride, trifluoroacetic anhydride, sulfuryl chloride, and thionyl chloride; followed by addition of the compound 13. Trialkylamine base is added after a time period of about 5 minutes to 24 hours at a temperature range from about −80° C. to 50° C.;

(b) Compound 13 and dimethylsulfoxide are premixed in one of said inert solvents, followed by addition of said activating agent and then followed by the addition of trialkylamine base at a time period of about 5 minutes to 24 hours. This occurs at a temperature range from about −80° C. to 50° C. Preferably the reaction is run in methylene chloride at about −5° to 5° C., where the compound of the formula 13 and dimethylsulfoxide are premixed and activated by trifluoroacetic anhydride. This is followed by triethylamine about two hours later. The reaction is then warmed to room temperature.

According to the invention compound 13 may be prepared by the reduction of a compound of the formula

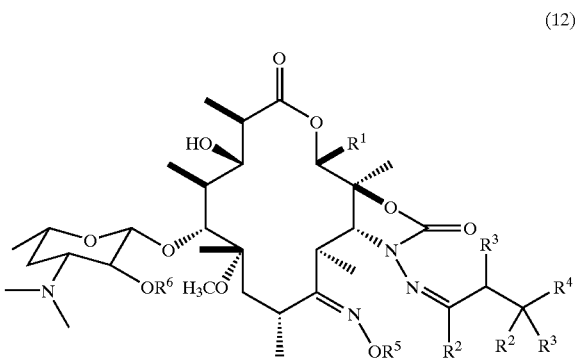

(12)

wherein:

$R^1$ to $R^6$ are defined above, with a metal hydride reducing agent including, but not limited to, sodium triacetoxyborohydride or sodium cyanoborohydride under acidic conditions.

The solvent includes, but is not limited to, acetic acid, acetonitrile, or alcoholic solvent with an acid additive such as acetic acid. The alcoholic solvent includes, but is not limited to, ethanol, methanol, isopropanol, or tertbutanol. Preferably the reaction is run at room temperature in acetic acid with an excess of sodium triacetoxyborohydride.

According to the invention, compound 12 may be prepared by the reaction of a compound of formula

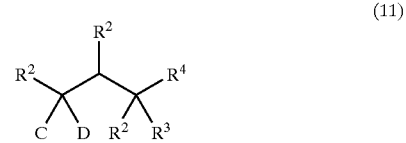

(11)

wherein:

$R^2$ to $R^4$ are defined above; and,

C and D together form oxo, or where C and D are independently hydroxy, $C_1$–$C_{10}$ alkoxy, or $C_1$–$C_{10}$ acyloxy, with a compound of formula

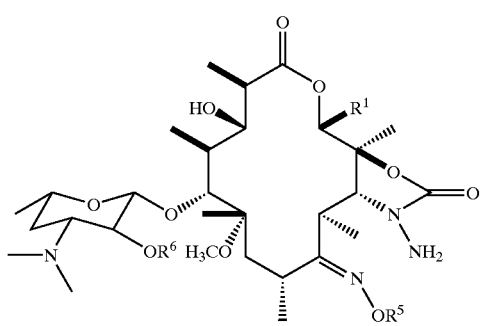
(10)

wherein:
R¹, R⁵, and R⁶ are defined above,
in inert solvent under neutral or acidic conditions.

Examples of acidic conditions include the use of an acid additive including, but is not limited to, acetic and formic acid and the solvent includes, but is not limited to water, methanol, ethanol, isopropanol, tertbutanol, dimethylformamide, N-methylpyrrolidinone, acetonitrile, dimethylacetamide, tetrahydrofuran, dimethylsulfoxide, dioxane, dimethoxyethane, dichloromethane, tetrachloroethane, dichloroethane, ethylacetate and toluene. The reaction can also be run under neutral conditions by heating the reaction in one of the above solvents without an acid additive between about 80° C. to 110° C. Preferably the reaction is run in acetic acid or ethanol with acetic acid at about room temperature.

According to the invention, compound 10 maybe prepared by the reaction of a compound of formula

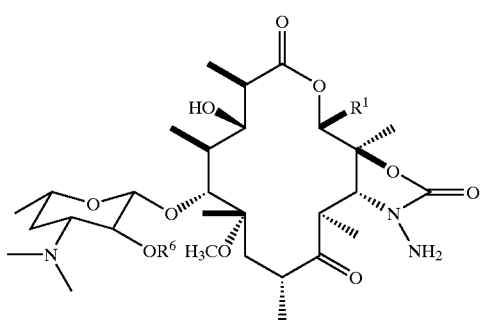
(9)

wherein:
R¹ and R⁶ are defined above,
with a reagent of the formula $H_2NOR^5$ as its free base, or acid addition salt, with or without added base. The base includes, but is not limited to, pyridine, 2,6-lutidine, imidazole, amine bases, or dimethylaminopyridine in a polar solvent including, but not limited to, methanol, ethanol, isopropanol, tert-butanol, dimethylformamide, N-methylpyrrolidinone, acetonitrile, dimethylacetamide and dimethylsulfoxide. The reaction is run at elevated temperatures between about 40° C. and 150° C. Preferably, the reaction is run with an excess of methoxylamine hydrochloride in isopropanol at about 80° C. to 85° C.

According to the invention, compound 9 may be prepared by the reaction of a compound of the formula

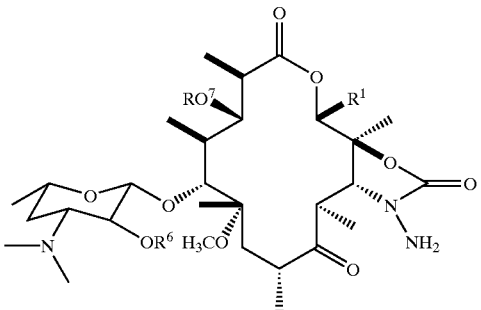
(2)

wherein:
R¹ and R⁶ are defined above; and,
R⁷ is a radical of formula

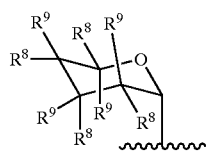

wherein each R⁸ and R⁹ are independently hydrogen, hydroxy, $C_1$–$C_6$ alkoxy, —OC(O)R⁴, —OC(O)NHNH₂, —OSi(R¹⁰)₃, or $C_1$–$C_{18}$ O-alkanoyl, wherein one or two carbons in the alkyl portion of said alkanoyl may be optionally replaced by a heteroatom selected from O, S, and NR²; and, R⁸ & R⁹ may be taken together to form

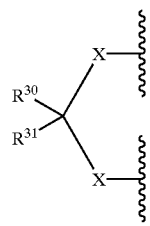

wherein:
X=O or S
Y=O or S
R³⁰, and R³¹=H, $C_1$–$C_6$ alkyl, $C_6$–$C_{10}$ aryl, or R³⁰ and R³¹ taken together form =O or =S
or R⁸ & R⁹ can be taken together to form;

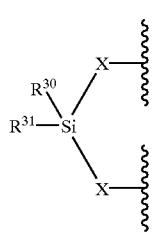

and each R¹⁰ is independently $C_1$–$C_{10}$ alkyl or $C_6$–$C_{10}$ aryl, with or without water, in a polar solvent including, but not limited to, water, methanol, ethanol, isopropanol, tert-butanol, dimethyl formamide, N-methylpyrrolidinone, acetonitrile, dimethylacetamide, tetrahydrofuran, dimethylsulfoxide, acetic acid, and formic acid. The acid includes, but is not limited to, hydrochloric, hydrobromic, hydroiodic, sulfuric, nitric, alkylsulfonic, tosic, triflic, or trifluoroacetic acid and the temperature is about −25° C. to 100° C. Preferably, the reaction is run in methanol with 12N HCL at about 30 to 40° C.

According to the invention, compound 2 may be prepared by the reaction of a compound of the formula (1)

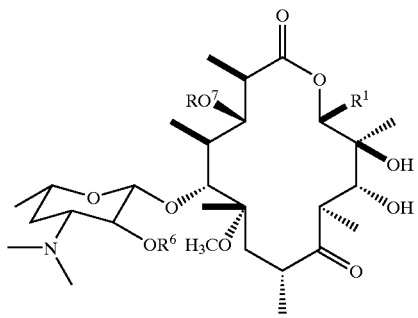

wherein:

$R^1$ and $R^6$ are as defined above and, $R^7$ is a radical of formula

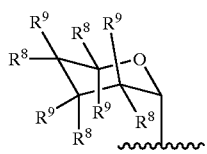

wherein each $R^8$ and $R^9$ are independently hydrogen, hydroxy, $C_1$–$C_6$ alkoxy, —OC(O)$R^4$, —OSi($R^{10}$)$_3$, or $C_1$–$C_{18}$ O-alkanoyl, wherein one or two carbons in the alkyl portion of said alkanoyl may be optionally replaced by a heteroatom selected from O, S, and $NR^2$;

and or $R^8$ & $R^9$ may be taken together to form

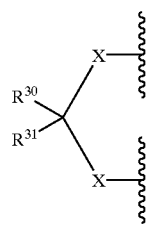

wherein:

X=O or S

Y=O or S $R^{30}$, and $R^{31}$=H, $C_1$–$C_6$ alkyl, $C_6$–$C_{10}$ aryl, or $R^{30}$ and $R^{31}$ taken together form =O or =S or $R^8$ & $R^9$ can be taken together to form

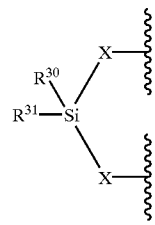

and each $R^{10}$ is independently $C_1$–$C_{10}$ alkyl or $C_6$–$C_{10}$ aryl, with a carboxyl source including, but not limited to, carbonyl diimidazole (CDI) phosgene, triphosgene, carbonyl bis-benzotriazole, carbonyl bishydroxybenzotriazole or carbonyl bis-1,2,4-triazole and a base including, but not limited to, 1,8-diazabicyclo[5,4,0]undec-7-ene (DBU), 1,2-dimethyl-1,4,5,6-tetrahydropyrimidine, sodium hexamethyldislazane, lithium dissopropylamide, or potassium hexamethyldisilazane in a range of inert solvents followed by treatment with hydrazine. The inert solvents include, but are not limited to, isopropylether, dimethyl formamide, N-methylpyrrolidinone, acetonitrile, dimethylacetamide, tetrahydrofuran dimethylsulfoxide, dioxane, dimethoxythane, dicholoromethane, tetrachloroethane, or dichloroethane. The reaction is monitored for the formation of an intermediate of formula (5)

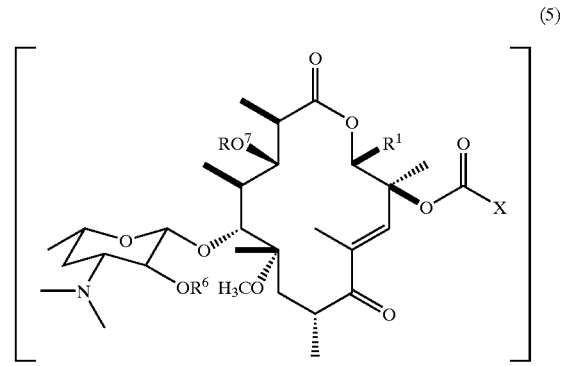

wherein:

$R^1$ and $R^6$ are as defined above and, $R^7$ is a radical of formula

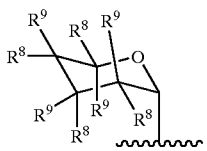

wherein each $R^6$ and $R^9$ are independently hydrogen, hydroxy, $C_1$–$C_6$ alkoxy, —OC(O)$R^4$, —OSi($R^{10}$)$_3$, —OC(O)X or $C_1$–$C_{18}$ O-alkanoyl, wherein one or two carbons in the alkyl portion of said alkanoyl may be optionally replaced by a heteroatom selected from O, S, and $NR^2$; and

9

$R^8$ & $R^9$ may be taken together to form

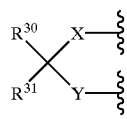

wherein:
X=O or S
Y=O or S
$R^{30}$, and $R^{31}$=H, $C_1$–$C_6$ alkyl, $C_6$–$C_{10}$ aryl, or $R^{30}$ and $R^{31}$ taken together form =O or =S
or $R^8$ & $R^9$ can be taken together to form

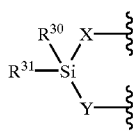

and each $R^{10}$ is independently $C_1$–$C_{10}$ alkyl or $C_6$–$C_{10}$ aryl; and, X is imidazole, 1,2,4-triazole, hydroxybenzotriazole, or benzotriazole.

Preferably, the reaction is run with CDI and DBU in ether solvent, and most preferably in tetrahydrofuran, with or without isopropylether.

Once conversion to intermediate 5 is complete, hydrazine or hydrazine hydrate is added to the reaction between about −78° C. to 50° C. Preferably hydrazine is added at about 10° C. to 20° C.

In a further aspect of this invention, a compound of formula (15)

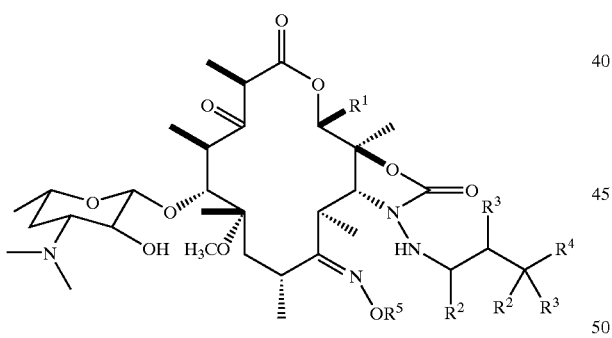

wherein:
$R^1$ is an alpha-branched $C_3$–$C_8$ alkyl, alkenyl, alkynyl, alkoxyalkyl or alkylthioalkyl group any of which may optionally be replaced by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be replaced by methyl or one to three groups independently selected from hydroxyl $C_1$–$C_4$ alkyl and halo, or a 3 to 6 membered oxygen or sulphur containing heterocyclic ring which may be saturated, or fully or partially unsaturated and which may optionally be replaced by one to three $C_1$–$C_4$ alkyl groups or halo atoms; or $R^1$ is phenyl which may be optionally replaced with one to three groups independently selected from $C_1$–$C_4$

10 alkyl, $C_1$–$C_4$ alkoxy and $C_1$–$C_4$ alkylthio groups, halogen atoms, hydroxyl groups, trifluoromethyl, and cyano; or $R^1$ has a formula (a) as shown below (a)

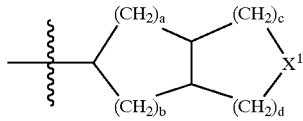

wherein $X^1$ is O, S or —$CH_2$—, a, b, c, and d are each independently selected from an integer ranging from 0 to 2 and a+b+c+d≦5; or $R^1$ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either of which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and each $R^2$ and $R^3$ is independently H or $C_1$–$C_6$ alkyl; and each $R^4$ is independently $C_6$–$C_{10}$ aryl or 5 to 10 membered heterocycle, wherein said aryl and heterocycle groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n$($C_1$–$C_{10}$ alkyl) wherein n is an integer ranging from 0 to 2, and $SO_2NR^2R^3$; and $R^5$ is H or $C_1$–$C_{10}$ alkyl, wherein 1 to 3 carbons of said alkyl are optionally replaced by a heteroatom selected from O, S, and $NR^2$, and said alkyl group is optionally replaced by 1 to 3 substituents independantly selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n$($C_1$–$C_{10}$ alkyl) wherein n is an integer ranging from 0 to 2, and $SO_2NR^2R^3$;

may be prepared by the oxidation of a compound of the formula (13)

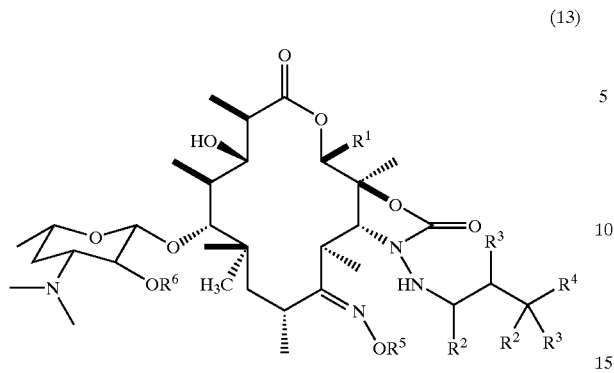

under Swern conditions wherein:
$R^1$ to $R^5$ are defined above and
$R^6$ is hydrogen.

Preferably, the Swern conditions are selected from the following:

(a) In an inert solvent including, but not limited to, dichloromethane, dichloroethane, and tetrachloroethane; dimethylsulfoxide is preactivated with activating agents including, but not limited to, oxalyl chloride, trifluoroacetic anhydride, sulfuryl chloride, and thionyl chloride; followed by addition of a compound of the formula 13. Trialkylamine base is added after a time period of about 5 minutes to 24 hours at a temperature range from about −80° C. to 50° C.;

(b) Compound 13 and dimethylsulfoxide are premixed in one of said inert solvents, followed by addition of said activating agent and then followed by the addition of trialkylamine base at a time period of about 5 minutes to 24 hours. This occurs at a temperature range from about −80° C. to 50° C. Preferably the reaction is run in methylene chloride at about −5° C. to 5° C., wherein the compound of the formula 13 and dimethylsulfoxide are premixed and activated by trifluoroacetic anhydride. This is followed by triethylamine about two hours later. The reaction is then warmed to room temperature.

In a further aspect of this invention, a compound of formula (10)

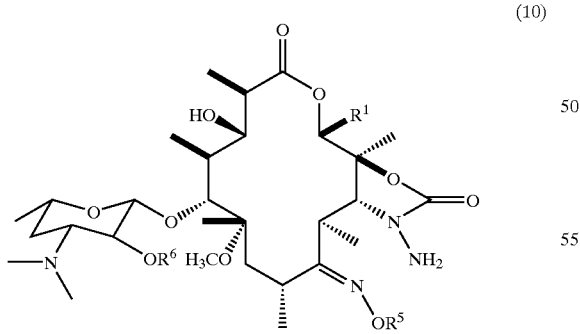

wherein:
$R^1$ and $R^5$ are defined above; and
$R^6$ is H, —C(O)$R^4$, or $C_1$–$C_{18}$ alkanoyl and wherein one or two carbons in the alkyl portion of said alkanoyl are optionally replaced by a heteroatom selected from O, S, and $NR^2$; is prepared by reaction of a compound of formula (2)

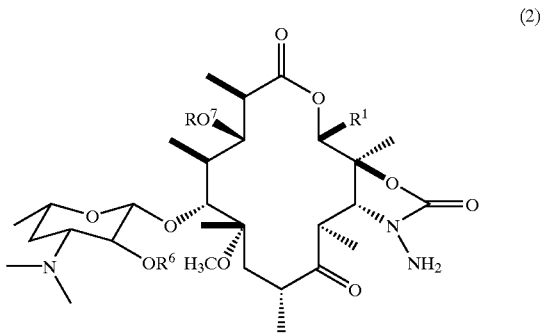

wherein:
$R^1$ and $R^6$ are defined above; and,
$R^7$ is a radical of formula

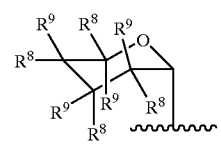

wherein each $R^8$ and $R^9$ are independently hydrogen, hydroxy, $C_1$–$C_6$ alkoxy, —OC(O)$R^4$, —OC(O)NHNH$_2$, —OSi($R^{10}$)$_3$, or $C_1$–$C_{18}$ O-alkanoyl, wherein one or two carbon in the alkyl portion of said alkanoyl may be optionally replaced by a heteroatom selected from O, S, and $NR^2$; and $R^8$ & $R^9$ may be taken together to form

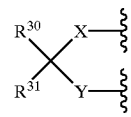

wherein:
X=O or S
Y=O or S
$R^{30}$, and $R^{31}$=H, $C_1$–$C_6$ alkyl, $C_6$–$C_{10}$ aryl, or $R^{30}$ and $R^{31}$ taken together form =O or =S
or $R^8$ & $R^9$ can be taken together to form

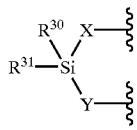

and each $R^{10}$ is independently $C_1$–$C_{10}$ alkyl or $C_6$–$C_{10}$ aryl,
with a reagent of the formula

H$_2$NOR$^5$ wherein $R^5$ is defined above, as its acid addition salt, with or without added base. The base includes, but is not limited to, pyridine, 2,6-lutidine, imidazole, amine bases, or dimethylaminopyridine in a polar solvent including, but not limited to, methanol, ethanol, isopropanol, tert-butanol, dimethylformamide, N-methylpyrrolidinone, acetonitrile, dimethylacetamide and dimethylsulfoxide. The reaction is run at elevated temperatures between about 40° C. and 150° C. Preferably, the reaction is run with an excess of methoxylamine hydrochloride and one equivalent of 2,6-lutidine in tert-butanol at about 75° C. to 85° C.

In a further aspect of this invention, a compound of formula 13 may be prepared by the reaction of a compound of formula 10

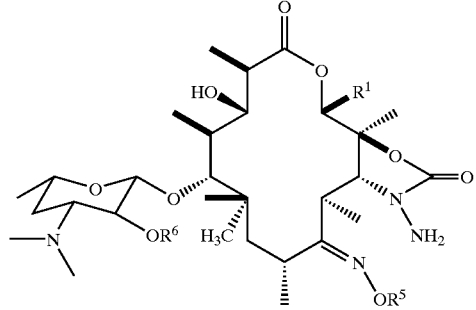

(10)

wherein:

$R^1$, $R^5$ and $R^6$ are defined above, with a compound of formula

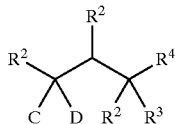

(11)

wherein:

$R^2$ to $R^4$ are defined above; and

C and D together form oxo, or where C and D are independently hydroxy, $C_1$–$C_{10}$ alkoxy or $C_1$–$C_{10}$ acyloxy, in a variety of solvents under acidic conditions.

The solvents include, but are not limited to, methanol, ethanol, isopropanol, tert-butanol, dimethylformamide, N-methylprrolidinone, acetonitrile, dimethylacetamide, tetrahydrofuran, dimethylsulfoxide, dichloromethane, tetrachloroethane, and dicholoethane. Acetic acid can be used as an additive, solvent or co-solvent. Preferably, the reaction is run in acetic acid or ethanol with acetic acid at room temperature. The reaction is monitored for conversion to an intermediate of formula 12. The intermediate of formula 12 is treated with a metal hydride reducing agent including, but not limited to, sodium triacetoxyborohydride or sodium cyanoborohydride. Preferably intermediate 12 is treated with an excess of sodium triacetoxyborohydride at room temperature to produce a compound of formula 13.

In a further aspect of this invention, a compound of formula 12

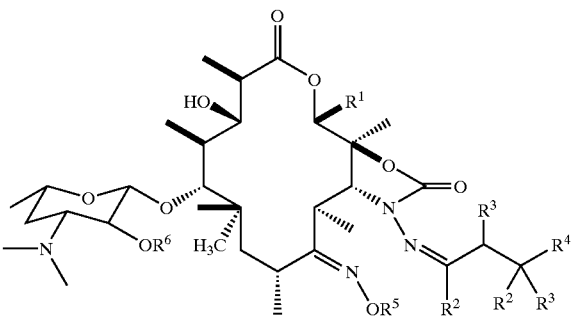

(12)

wherein:

$R^1$ to $R^6$ are defined above, may be prepared by a reaction of a compound of formula

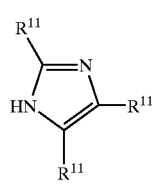

(20)

wherein:

each $R^{11}$ is independently selected from H, —C(O)O ($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n$($C_1$–$C_{10}$ alkyl) wherein n is an integer ranging from 0 to 2, and $SO_2NR^2R^3$; wherein said aryl and heterocycle groups are optionally replaced by 1 to 3 substituents independently selected from the group consisting of —C(O)O ($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n$($C_1$–$C_{10}$ alkyl) wherein n is an integer ranging from 0 to 2, and $SO_2NR^2R^3$; wherein one or two carbons in the alkyl portion of said alkyl, alkoxy, or alkanoyl groups may be optionally replaced by a heteroatom selected from O, S, and $NR^2$;

with a compound of formula

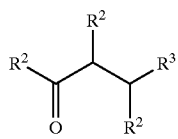

wherein:

$R^2$ and $R^3$ are defined above, in an alcoholic solvents under acidic conditions.

The alcohol solvent includes, but is not limited to, methanol, ethanol, isopropanol or tert-butanol and the acid includes, but is not limited to, acetic or formic acid. The reaction is monitored for the formation of the intermediate of formula 11 at which point a compound of formula 10 above is added. Preferably, the reaction is run in ethanol with acetic acid at room temperature.

In another aspect of the invention, a compound of formula (13)

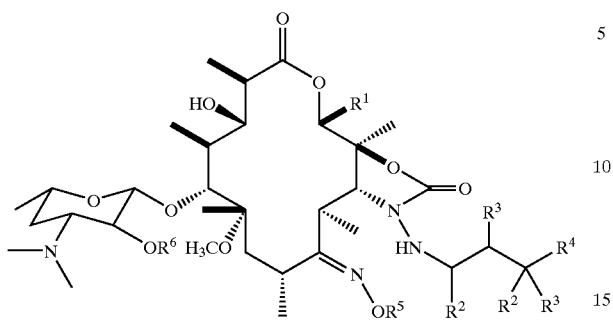

wherein:
R$^1$ to R$^5$ are defined above and
R$^6$ is H, —C(O)R$^4$, or C$_1$–C$_{18}$ alkanoyl, wherein one or two carbons in the alkyl portion of said alkanoyl may be optionally replaced by a heteroatom selected from O, S, and NR$^2$; may be prepared by reaction of a compound of formula (20)

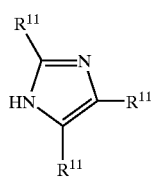

as its free base or acid addition salt
wherein:
R$^{11}$ is defined above,
with a compound of formula

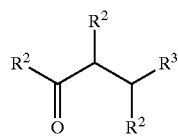

wherein:
R$^2$ and R$^3$ are defined above
and a compound of formula (10)

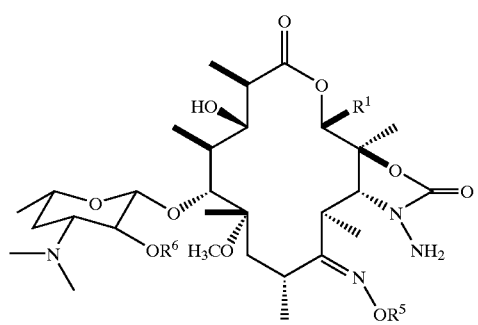

under acidic conditions.
wherein:
R$^1$, R$^5$ and R$^6$ are defined above. Acids that are used as additives or co-solvent are acetic and formic acid, and solvents include, but are not limited to, acetic acid, formic acid, dichloromethane, dichloroethane, tetrachloroethane, or tetrahydrofuran. The reaction is monitored for the formation of an intermediate of the formula 12 above, at which point it is treated with a metal hydride reducing agent such as sodium triacetoxyborohydride or sodium cyanoborohydride. Preferably, the reaction is run at room temperature in acetic acid with or without dichloromethane as a co-solvent, using an excess of the compound of formula 20 as its bishydrochloric acid salt, and is followed by an excess of sodium triacetoxyborohydride after formation of the compound of formula 12.

In another aspect of the invention, a compound of formula (12)

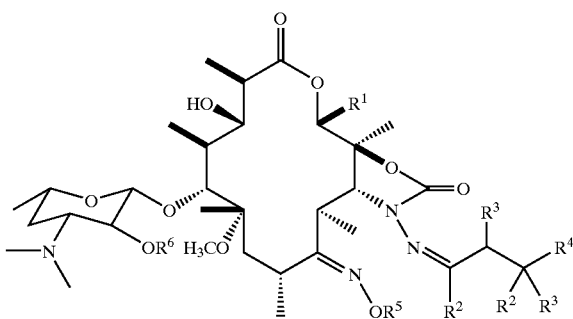

wherein:
R$^1$ to R$^6$ are defined above,
may be prepared by reaction of a compound of formula (20)

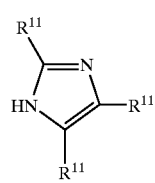

as its free base or acid addition salt
wherein:
R$^{11}$ is defined above,
with a compound of formula

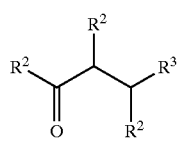

wherein:
R$^2$ and R$^3$ are defined above, and a compound of formula

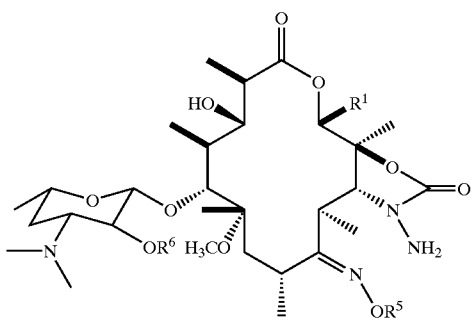
(10)

wherein:
$R^1$, $R^5$ and $R^6$ are defined above, under acidic conditions. Acids that are used as additives or co-solvent are acetic and formic acid, and solvents include, but are not limited to, acetic acid, formic acid, dichloromethane, dichloroethane, tetrachloroethane, or tetrahydrofuran.

In another aspect of the invention, a compound of formula

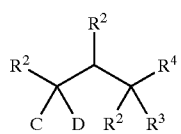
(11)

wherein:
$R^2$ to $R^4$ are defined above; and
C and D together form oxo, or where C and D are independently hydroxy, $C_1$–$C_{10}$ alkoxy or $C_1$–$C_{10}$ acyloxy, may be prepared by the reaction of a compound of formula

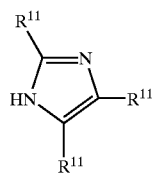
(20)

wherein:
$R^{11}$ is defined above,
with a compound of formula

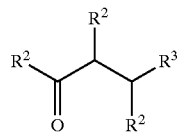

wherein
$R^2$ and $R^3$ are defined above, in a variety of alcoholic solvents under acidic conditions. The solvents include, but are not limited to, methanol, ethanol, isopropanol, or tert-butanol. Acids that can be used as an additive or co-solvent include, but are not limited to acetic and formic acid. Preferably the reaction is run in ethanol with acetic acid at room temperature.

In another aspect of the invention a compound of formula 20 may be prepared by the reaction of a compound of formula

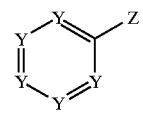
(21)

wherein:
each Y is independently selected from N or $CR^{12}$; and
each $R^{12}$ is independently selected from the group consisting of hydrogen, $C(O)O(C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n(C_1$–$C_{10}$ alkyl) wherein n is an integer ranging from 0 to 2, and $SO_2NR^2R^3$; and,
Z is chlorine, bromine, or iodine,
with a compound of formula (22)

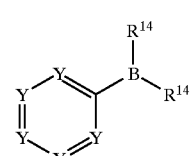

wherein
$R^{11}$ is defined above, and
$R^{13}$ is hydrogen, $C(O)R^4$, —$Si(R^{10})_3$, $C_1$–$C_{10}$ alkyl, or $C_1$–$C_{18}$ alkanoyl, wherein one or two carbons in the alkyl portion of said alkyl or alkanoyl may be optionally replaced by a heteroatom selected from O, S, and $NR^2$.

The reaction is run in the presence of a palladium catalyst including, but not limited to, palladium (II) acetate and a trialkyl or triarylphosphine including, but not limited to triphenylphosphine, tri-t-butyl-phosphine, or tri-o-tolylphosphine. In the reaction the base includes but is not limited to cessium carbonate or potassium carbonate and the solvent includes, but is not limited to, dimethylformamide or N-methylpyrrlidinone at a temperature of about 25° C. to 200° C. Preferably the reaction is run with benzylimidazole and 3-bromopyridine in dimethylformamide at reflux with palladium (II) acetate, triphenyl phosphine and cessium carbonate.

In another aspect of the invention, a compound of formula 20 may be prepared by the reaction of a compound of formula (23)

wherein:
$R^{14}$ is selected from hydroxy, $C_1$–$C_{10}$ alkoxy, and $C_1$–$C_{10}$ alkyl, wherein one or two carbons in the alkyl portion of the alkyl or alkoxy may be optionally replaced by a heteroatom selected from O, S, and $NR^2$; and
Y is defined above, with a compound of formula

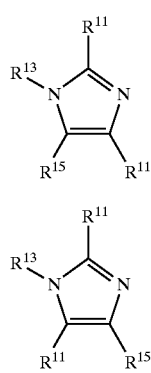

(24)

(25)

wherein:
$R^{11}$ and $R^{13}$ are defined above, and,
$R^{15}$ is selected from chlorine, bromine or iodine.

The reaction is run in the presence of an inert solvent, base and a palladium catalyst at a temperature at about 25° C. to 125° C. for about 30 minutes to 48 hours. The base includes, but is not limited to, sodium carbonate, sodium bicarbonate, potassium carbonate, potassium hydroxide, sodium hydroxide, potassium fluoride, and barium hydroxide. Suitable palladium catalysts include, but are not limited to, tetrakis(triphenylphosphine)palladium(0), dichlorobis(triphenylphosphine)palladium(II), palladium(II) acetate, allyllpalladium chloride dimer, and tris(dibenezylideneacetone)dipalladium(0). Optionally the reaction medium could also contain a triarylphosphine or trialkylphosphine, examples of which include, but are not limited to, triphenylphosphine, tri(o-tolyl)phosphine and trit-butylphosphine and could also contain tetrabutylammonium iodide. The inert solvent includes, but is not limited to tetrahydrofuran, dioxane, and dimethoxyethane. Preferably, the reaction is run at reflux in dimethylformamide with potassium hydroxide, tetrakis(triphenylphosphine)palladium(0), and tetrabutylammonium iodide.

In another aspect a compound of formula 20 may be prepared by reaction of a compound of formula

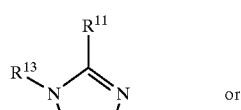

or (24)

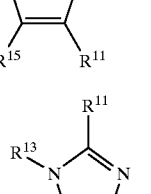

(25)

wherein:
$R^{11}$, $R^{13}$ and $R^{15}$ are defined above,
with reagents including, but not limited to,
(a) alkylmagnesium chloride, bromide or iodide, where the alkyl includes, but is not limited to, methyl, ethyl, isopropyl, or t-butyl, or magnesium(0), followed by treatment with zinc chloride, zinc bromide, or zinc iodide, or (b) with reagents such as alkylzinc chloride, alkyl zinc bromide or alkylzinc iodide, where the alkyl includes, but is not limited to methyl, ethyl, isopropyl, or t-butyl or zinc(0) and zinc chloride, zinc bromide, or zinc iodide followed by reaction with a compound of formula

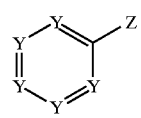

(21)

wherein:
Y and Z are defined above,
in the presence of a palladium catalyst including, but not limited to, tetrakis(triphenylphosphine)palladium(0), dichlorobis(triphenylphosphine)palladium(II), palladium(II)acetate, allylpalladium chloride dimer, and tris(dibenzylideneacetone)dipalladium(0). The reaction medium may optionally also contain a triarylphosphine or trialkylphosphine including, but are not limited to, triphenylphosphine, tri(o-tolyl) phosphine and trit-butylphosphine. The inert solvent includes, but is not limited to, tetrahydrofuran, dioxane, and dimethoxyethane. Preferably, the reaction is run in tetrahydrofuran, with ethylmagnesium bromide followed by zinc chloride, followed by the compound of formula 21 and tetrakis(triphenylphosphine)palladium (0), and the reaction is heated from about room temperature to 70° C.

In another aspect of the invention, a compound of formula 20 may be prepared by the reaction of a compound of formula

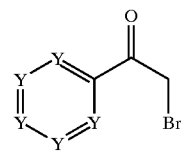

(26)

as its free base or acid addition salt
wherein:
Y is defined above
with formamide at the elevated temperature of about 120° C. to 220° C. Preferably the reaction is run in formamide at about 150° C. to 170° C.

In another aspect of the invention, a compound of formula 20 may be prepared by the reaction of a compound of formula

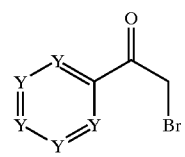

(26)

as its free base or acid addition salt
wherein:
Y is defined above
with formamidine acetate in a polar solvent with or without added base at temperatures between about 25°

C. to 200° C. Examples of polar solvents include, but are not limited to, dimethylformamide, dimethylacetamide, acetonitrile, formamide, and dimethylsulfoxide. Examples of bases include, but are not limited to, potassium acetate and sodium acetate. Preferably, the reaction is run in dimethylformamide with potassium acetate at about 60° C. to 70° C.

In another aspect of the invention, a compound of formula 13 may be prepared by the reaction of a compound of formula (19)

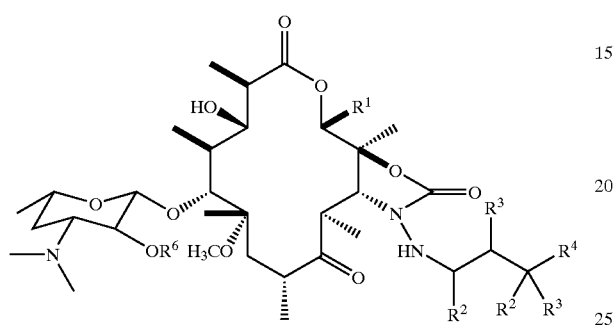

wherein:

$R^1$ to $R^4$ and $R^6$ are defined above, with a reagent of the formula as its free base or acid addition salt,

$H_2NOR^5$ wherein $R^5$ is defined above, with or without the addition of a base. This reaction includes run with a base including, but not limited to, pyridine, 2,6-lutidine, imidazole, amine base, or dimethylaminopyridine in a polar solvent including but not limited to, methanol, ethanol, isopropanol, tert butanol, dimethylformamide, N-methylpyrrolidinone, acetonitrile dimethylacetamide and dimethyl sulfoxide. The reaction is usually run at elevated temperatures between about 40° C. to 150° C. Preferably, the reaction is run with an excess of methoxylamine hydrochloride in isopropanol at about 75° C. to 85° C.

According to the invention compound 19 may be prepared by the reaction of a compound of the formula (17)

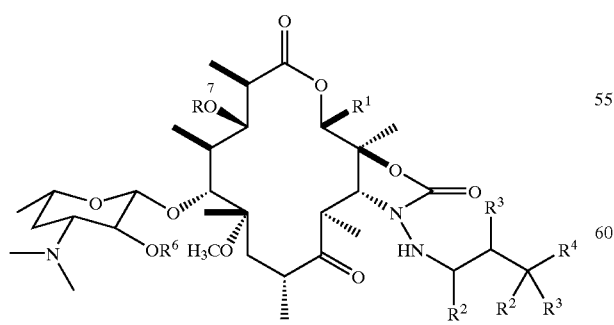

wherein $R^1$ to $R^4$ and $R^6$ are as defined above, $R^7$ is a radical of formula

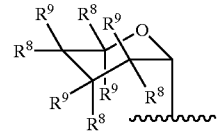

wherein each $R^8$ and $R^9$ are independently hydrogen, hydroxy, $C_1$–$C_6$ alkoxy, —OC(O)$R^4$, —OSi($R^{10}$)$_3$, —OC(O)X or $C_1$–$C_{18}$ O-alkanoyl, wherein one or two carbons in the alkyl portion of the alkanoyl may be optionally replaced by a heteroatom selected from O, S, and $NR^2$ and $R^8$ & $R^9$ may be taken together to form

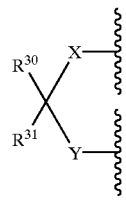

wherein:

X=O or S

Y=O or S $R^{30}$, and $R^{31}$=H, $C_1$–$C_6$ alkyl, $C_6$–$C_{10}$ aryl, or $R^{30}$ and $R^{31}$ taken together form =O or =S or $R^8$ & $R^9$ can be taken together to form

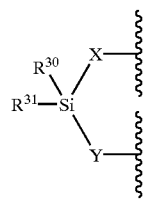

and each $R^{10}$ is independently $C_1$–$C_{10}$ alkyl or $C_6$–$C_{10}$ aryl;

with acids such as hydrochloric, hydrobromic, hydroiodic, sulfuric, nitric, alkylsulfonic, tosic, triflic, or trifluoroacetic acid, with or without water, in a polar solvent including but not limited to water, methanol, ethanol, isopropanol, tertbutanol, dimethylformamide, N-methylpyrrolidinone, acetonitrile, dimethylacetamide, tetrahydrofuran, dimethylsulfoxide, acetic acid, or formic acid over a range of temperatures from about −25° C. to 100° C. Preferably, the reaction is run in methanol with 12N HCl at about 30° C. to 40° C.

According to the invention, a compound of formula 17 may be prepared by the reaction of a compound of the formula

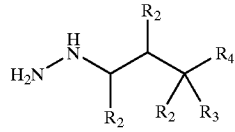

(16)

wherein:
$R^2$, $R^3$, and $R^4$ are defined above,
with a compound of formula

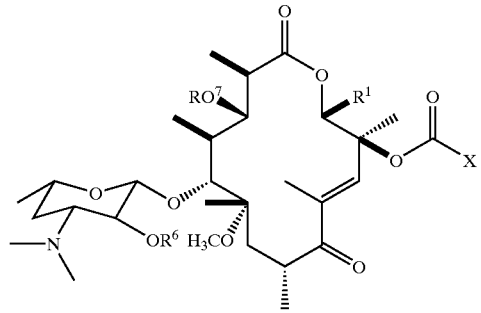

(5)

wherein:
$R^1$, $R^6$ and $R^7$ are as defined above, and
X is imidazole, 1,2,4-triazole, hydroxybenzotriazole, or benzotriazole, in an inert solvent including, but not limited to, isopropylether, dimethyl formamide N-methylpyrrolidinone, acetonitrile, dimethylacetamide, tetrahydrofuran, dimethyl sulfoxide, dioxane, dimethoxyethane, dichloromethane, tetrachloroethane, and dichloroethane. The reaction is run at a temperature between 0° C. to 150° C. Preferably, the reaction is run in acetonitrile at reflux.

According to the invention, a compound of formula (5) may be prepared by reacting a compound of formula

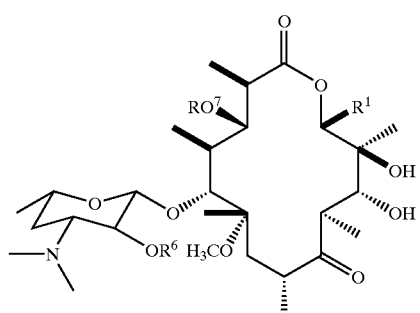

(1)

wherein:
$R^1$, $R^6$ and $R^7$ are as defined above,
with a carboxyl source including, but not limited to, carbonyl diimidazole (CDI) phosgene, triphosgene, carbonyl bis-benzotriazole, carbonyl bishydroxybenzotriazole or carbonyl bis-1,2,4-triazole and a base including, but not limited to, 1,8-diazabicyclo[5,4,0]undec-7-ene (DBU), 1,2-dimethyl-1,4,5,6-tetrahydropyrimidine, sodium hexamethyldislazane, lithium dissopropylamide, or potassium hexamethyidisilazane in a range of inert solvents. The inert solvent includes, but is not limited to, isopropylether, dimethyl formamide, N-methylpyrrolidinone, acetonitrile, dimethylacetamide, tetrahydrofuran dimethylsulfoxide, dioxane, dimethoxythane, dichloromethane, tetrachloroethane, or dichioroethane. Preferably, the reaction is run with CDI and DBU in ether solvent, and most preferably in tetrahydrofuran, with or without isopropylether.

In another aspect of the invention a compound of formula (13) may be prepared by a reaction of a compound of the formula

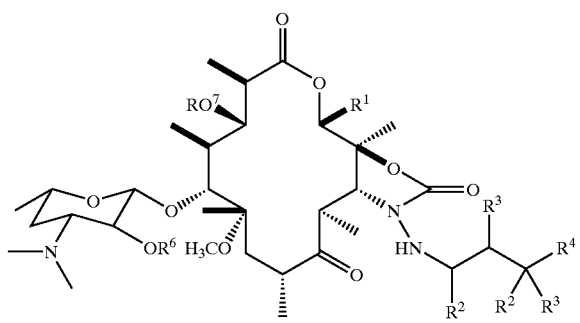

(17)

wherein:
$R^1$ to $R^4$, $R^6$ and $R^7$ are as defined above,
with a reagent of the formula $H_2NOR^5$ wherein $R^5$ is defined above,
as its acid addition salt, with or without a base including, but not limited to, pyridine, 2,6-lutidine, imidazole, amine, or dimethylaminopyridine in a polar solvent including, but not limited to methanol, ethanol isopropyl, tertbutanol, dimethylforamide, N-methylpyrrolidinone, acetonitrile, and dimethylacetamide, or dimethylsulfoxide at an elevated temperature between about 40 and 150° C. Preferably the reaction is run with an excess methoxylamine hydrochloride and about one equivalent of 2,6-lutidine in t-butanol at about 70° C. to 90° C.

In another aspect of the invention, a compound of formula 17 may be prepared by the reaction of a compound of formula

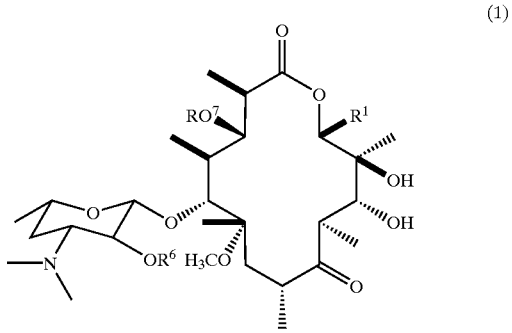

(1)

wherein:
$R^1$, $R^6$ and $R^7$ are as defined above,
with a carboxyl source including but not limited to, carbonyl diimidazole (CDI) phosgene, triphosgene, carbonyl bis-benzotriazole, carbonyl bishydroxybenzotriazole or carbonyl bis-1,2,4-triazole and a base including, but not limited to 1,8-diazabicyclo[5,4,0]undec-7-ene (DBU), 1,2-dimethyl-1,4,5,6-tetrahydropyrimidine, sodium hexamethyldislazane, lithium dissopropylamide, or potassium hexamethyldisilazane in a range of inert solvents followed by reaction with a compound of formula (16). The inert solvent includes, but is not limited to, isopropylether, dimethyl formamide, N-methylpyrrolidinone, acetonitrile, dimethylacetamide, tetrahydrofuran dimethylsulfoxide, dioxane, dimethoxythane, dicholoromethane, tetrachloroethane, or dichloroethane. Preferably, the reaction is run with CDl and DBU in acetonitrile. The reaction is monitored for the formation of intermediate of formula

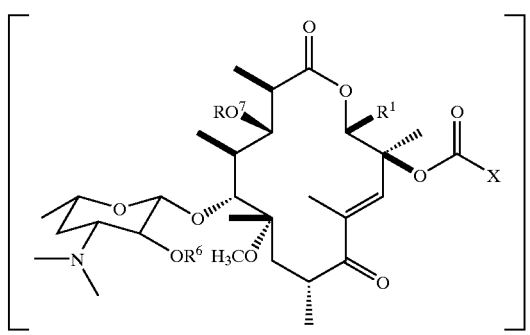

(5)

wherein:

$R^1$, $R^6$, X, and $R^7$ are as defined above.

Once conversion to formula 5 is complete, a compound of formula 16 is added to the reaction between about 0° C. and 150° C. Preferably the addition is done between about 25° C. and 75° C.

According to the invention, a compound of formula 16 may prepared by the reaction of a compound of formula

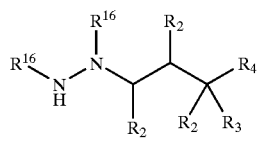

(32)

wherein:

$R^2$, $R^3$, and $R^4$ are defined above; and, $R^{16}$ is —C(O)OR$^5$, under conditions suitable to remove the $R^{16}$ protecting group. Where $R^{16}$ is tert-butylcarbamate (BOC), the reaction is with acids such as hydrochloric, hydrobromic, hydroiodic, sulfuric, nitric, alkylsulfonic acids, tosic acid, triflic acid, or trifluoroacetic acid, with or without water, in a variety of polar or nonpolar solvents including, but not limited to water, methanol, ethanol, isopropanol, tertbutanol, dimethylformamide, N-methylpyrrolidinone, acetonitrile, dimethylacetamide, tetrahydrofuran, dimethylsulfoxide, acetic acid, formic acid, toluene, dichloroethane, tetrachloroethane, dioxane, and dichloromethane over a range of temperatures from about 25° C. to 200° C. Preferably, the reaction is run in methanol with 6N HCl at about 40° C. to 60° C.

According to the invention, a compound of formula 32 may be prepared by the reaction of a compound of formula

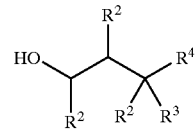

(31)

wherein:

$R^2$, $R^3$, and $R^4$ are defined above, with a trialkyl or triaryl phosphine and a reagent of formula

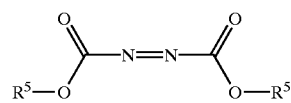

in an inert solvent, wherein:

$R^5$ is defined above,

Examples of phosphines include, but are not limited to, triphenylphosphine, trimethylphosphine, tritbutylphosphine, or tributylphosphine. Examples of inert solvents include, but are not limited to, dichloromethane, dichloroethane, tetrachloroethane, dioxane, acetonitrile, or tetrahydrofuran. Preferably, the reaction is run with triphenylphosphine and ditert-butylazadicarboxylate in tetrahydrofuran from about 0° C. to room temperature.

According to the invention, a compound of formula 31 may be prepared by the deprotection of a compound of formula

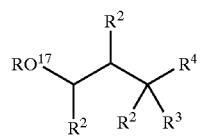

(30)

wherein:

$R^2$, $R^3$, and $R^4$ are defined above; and, $R^{17}$ is Si($R^{10}$)$_3$, $R^5$, $R^6$, or C(O)OR$^5$, under conditions appropriate to remove the alcohol protecting group $R^{17}$.

a) When $R^{17}$ is trisubstitutedsilyl, disubstituted ketal, or monosubstituted acetal, the reaction is with acids such as hydrochloric, hydrobromic, hydroiodic, sulfuric, nitric, alkylsulfonic acids, tosic acid, triflic acid, or trifluoroacetic acid; or if b) $R^{17}$ is trisubstitutedsilyl, the reaction is with flouride sources including but not limited to, tetrabutylammonium flouride, hydroflouric acid, HF-pyridine, potassium flouride, cesium flouride, and sodium flouride, with or without water, in a polar or nonpolar solvents including, but not limited to water, methanol, ethanol, isopropanol, tert-butanol, dimethylformamide, N-methylpyrrolidinone, acetonitrile, dimethylacetamide, tetrahydrofuran, dimethylsulfoxide, acetic acid, formic acid, toluene, dichloroethane, tetrachloroethane, dioxane, and dichloromethane over a range of temperatures from about 25°

C. to 200° C. Preferably, $R^{17}$ is tert-butyldimethylsilyl and the reaction is run in tetrahydrofuran with tetrabutylammonium flouride.

When $R^{17}$ is —C(O)OR$^5$ or $R^6$, the protecting group includes cleaved with a nucleophile.

a) solvolysis in alcoholic or aqueous solvent, with the addition of base optional to accelerate the reaction. Examples of alcoholic solvents include, but are not limited to, methanol, ethanol, isopropanol, and tert-butanol. Examples of useable bases include, but are not limited to, sodium carbonate, sodium bicarbonate, potassium carbonate, potassium hydroxide, sodium hydroxide, potassium flouride, and barium hydroxide, or b) with a nucleophile including but not limited to, ammonium hydroxide, monoalky amine, dialkylamine, alkanethiol, or hydroxide in a solvent including but not limited to, water, methanol, ethanol, isopropanol, tertbutanol, dimethylformamide, N-methylpyrrolidinone, acetonitrile, dimethylacetamide, tetrahydrofuran, dimethylsulfoxide, dioxane, dimethoxyethane, dichloromethane, tetrachloroethane, dichloroethane, ethylacetate and toluene.

Preferably, this deprotection is run in methanol with the addition of potassium carbonate at room temperature.

According to the invention, a compound of formula 30 may be prepared by the reaction of a compound of formula

(29)

wherein:

$R^2$, $R^3$, and $R^{17}$ are defined above, with a compound of formula 20 and base in a polar solvent. Examples of bases include, but are not limited to, sodium hydride, potassium tert-butoxide, sodium tert-butoxide, potassium hexamethyldisilazide, sodium hexamethyidisilazide, and lithium diisopropylamide. Examples of solvents include, but are not limited to, dimethylformamide, N-methylpyrrolidinone, acetonitrile, dimethylacetamide, tetrahydrofuran, and dimethylsulfoxide. Preferably, the reaction is run with sodium hydride in dimethylformamide.

According to the invention, a compound of formula 29 may be prepared by the reaction of a compound of formula

(28)

wherein:

$R^2$, $R^3$, and $R^{17}$ are defined above, with a mesylating agent and base in inert solvent. Mesylating agents include, but are not limited to, mesic anyhydride, mesyl chloride, and mesyl bromide. Useable bases include, but are not limited to, trialkylamines such as triethylamine or diisopropylethylamine, pyridine, lutidine, and dimethylaminopyridine.

Examples of inert solvents include, but are not limited to, tetrahydrofuran, dichloroethane, tetrachloroethane, dioxane, and dichloromethane. Preferably, the reaction is run with mesyl chloride and triethylamine in dichloromethane.

According to the invention, a compound of formula 28 may be prepared by the selective protection of a compound of formula

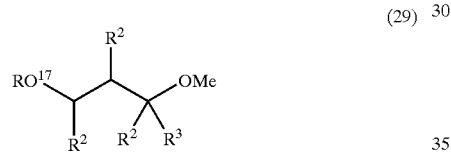

(27)

wherein:

$R^2$, and $R^3$ are defined above, with reagents including but not limited to, trisubstitutedsilyl chloride, trisubstitutedsilyl imidazole, trisubstitutedsilyl triflate, acid chlorides, acid anhydrides, chloroformates, carbonate anhydrides, mixed anhydrides, and isocyanates and a base including but not limited to, imidazole, trialkylamines such as triethylamine or diisopropylethylamine, pyridine, lutidine, and dimethylaminopyridine in aprotic solvents including but not limited to, dimethylformamide, N-methylpyrrolidinone, acetonitrile, dimethylacetamide, tetrahydrofuran, dimethylsulfoxide, toluene, dichloroethane, tetrachloroethane, dioxane, and dichloromethane. Preferably, the reaction is run with tert-butyldimethylsilyl chloride and imidazole in dichloromethane at about –5° C. to 50° C. range.

In another aspect of the invention, a compound of formula (16) may be prepared by the reduction of a compound of formula

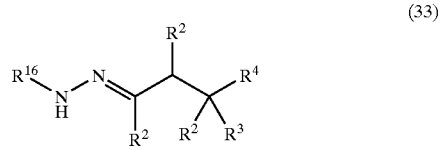

(33)

wherein:

$R^2$, $R^3$, $R^4$, and $R^{16}$ are defined above, with a metal hydride reducing agent such as sodium triacetoxyborohydride or sodium cyanoborohydride under acidic conditions. The solvent includes, but is not limited to, acetic acid, acetonitrile, or alcoholic solvent with an acid additive such as acetic acid. The alcoholic solvent includes, but is not limited to ethanol, methanol, isopropanol, and tert-butanol. Preferably, the reaction is run at room temperature in acetic acid with an excess of sodium triacetoxyborohydride.

According to the invention, a compound of formula (33) includes prepared by the reaction of a compound of the formula

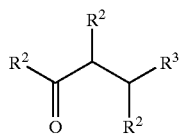

wherein:

R² and R³ are defined above, with a reagent of formula

wherein:

R¹⁶ is defined above under neutral or acidic conditions.

Some representative acids included as additives, solvent, or co-solvent are acetic and formic acid, and usable solvents include, but are not limited to water, methanol, ethanol, isopropanol, tertbutanol, dimethylformamide, N-methylpyrrolidinone, acetonitrile, dimethylacetamide, tetrahydrofuran, dimethylsulfoxide, dioxane, dimethoxyethane, dichloromethane, tetrachloroethane, dichloroethane, ethylacetate and touene. Examples of neutral conditions are heating the reaction in solvent without acid additive between about 80° C. and 110° C. Preferably, the reaction is run in acetic acid or ethanol with acetic acid at about room temperature.

In another aspect of the invention, a compound of formula 16 may be prepared by the reaction of a compound of formula

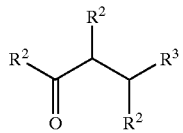

wherein:

R² and R³ are defined above, with reagent of formula

wherein:

R¹⁶ is defined above in a variety of solvents under acidic conditions, followed by reduction with a metal hydride reducing agent including sodium triacetoxyborohydride or sodium cyanoborohydride under acidic conditions. Some representative acids that may be used as additives, solvent, or co-solvent includes but are not limited to acetic and formic acid, and the solvents include, but are not limited to, acetonitrile, dichloromethane, tetrachloroethane, and dichloroethane. Preferably, the reaction is run in acetic acid at about room temperature, followed by reduction with sodium triacetoxyborohydride.

The invention also includes a compound of the formula (14)

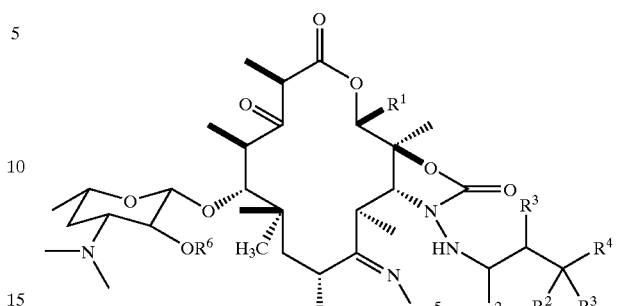

wherein:

R¹ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydrox $C_1$–$C_4$ alkyl and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or R¹ is phenyl which may be optionally replaced one to three groups selected independently from $C_1$–$C_4$ alkyl, $C_1$–$C_4$ alkoxy and $C_1$–$C_4$ alkylthio groups, halogen atoms, hydroxyl groups, trifluoromethyl, and cyano; or R¹ may be a formula (a) as shown below (a)

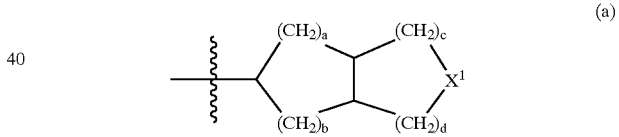

wherein $X^1$ is O, S or —$CH_2$—, a, b, c, and d are each independently selected from an integer ranging from 0 to 2 and a+b+c+d≦5; or R¹ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either or which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and, each $R^2$ and $R^3$ is independently H or $C_1$–$C_6$ alkyl; except that neither $R^2$ or $R^3$ can be H when $R^1$ is —$CH_2CH_3$; and each $R^4$ is independently $C_6$–$C_{10}$ aryl or 5 to 10 membered heterocycle, wherein said aryl and heterocyclic groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n(C_1$–$C_{10}$ alkyl) wherein n is an integer ranging from 0 to 2, and $SO_2NR^2R^3$; and $R^5$ is H or $C_1$–$C_{10}$ alkyl, wherein 1 to 3 carbons of said alkyl are optionally replaced by a heteroatom selected from O, S, and $NR^2$, and said alkyl group is optionally replaced by 1 to 3 substituents independantly selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n(C_1$–$C_{10}$ alkyl) wherein n is an integer ranging from 0 to 2, and $SO_2NR^2R^3$; and $R^6$ is H, —C(O)$R^4$, or $C_1$–$C_{18}$ alkanoyl, wherein one or two carbons in the alkyl portion of said alkanoyl may be optionally replaced by a heteroatom selected from O, S, and $NR^2$.

The invention also includes a compound of the formula (13)

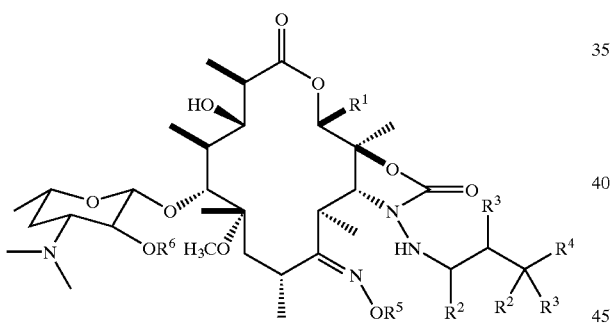

wherein:

$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from $C_1$–$C_4$ alkyl, $C_1$–$C_4$ alkoxy and $C_1$–$C_4$ alkylthio groups, halogen atoms, hydroxyl groups, trifluoromethyl, and cyano; or $R^1$ can be a formula (a) as shown below

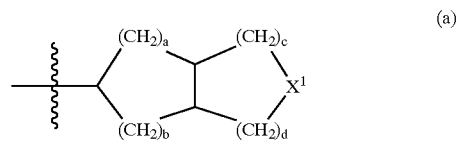

(a)

wherein $X^1$ is O, S or —$CH_2$—, a, b, c, and d are each independently selected from an integer ranging from 0 to 2 and a+b+c+d≦5; or $R^1$ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either or which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms except that $R^1$ is not —$CH_2CH_3$; and each $R^2$ and $R^3$ is independently H or $C_1$–$C_6$ alkyl except that neither $R^2$ or $R^3$ can be H when R1 is —$CH_2CH_3$; and, each $R^4$ is independently $C_6$–$C_{10}$ aryl or 5 to 10 membered heterocycle, wherein said aryl and heterocyclic groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n(C_1$–$C_{10}$ alkyl) wherein n is an integer ranging from 0 to 2, and $SO_2NR^2R^3$; and $R^5$ is H or $C_1$–$C_{10}$ alkyl, wherein 1 to 3 carbons of said alkyl are optionally replaced by a heteroatom selected from O, S, and $NR^2$, and said alkyl group optionally replaced by 1 to 3 substituents independantly selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n(C_1$–$C_{10}$ alkyl) wherein n is an integer ranging from 0 to 2, and $SO_2NR^2R^3$; and $R^6$ is H, —C(O)$R^4$, or $C_1$–$C_{18}$ alkanoyl, wherein one or two carbons in the alkyl portion of said alkanoyl may be optionally replaced by a heteroatom selected from O, S, and $NR^2$.

The invention also relates a compound of the formula (12)

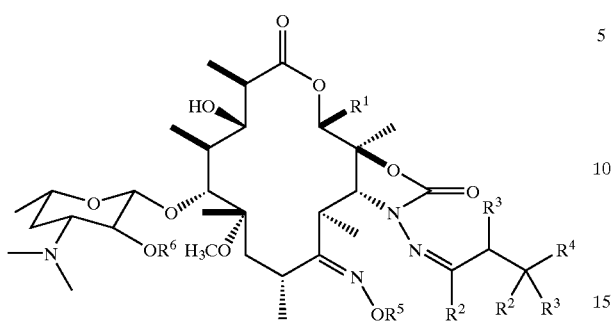

wherein:
- $R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or
- $R^1$ is phenyl which may be optionally replaced with one to three groups independently selected from $C_1$–$C_4$ alkyl, $C_1$–$C_4$ alkoxy and $C_1$–$C_4$ alkylthio groups, halogen atoms, hydroxyl groups, trifluoromethyl, and cyano; or
- $R^1$ may be a formula (a) as shown below (a)

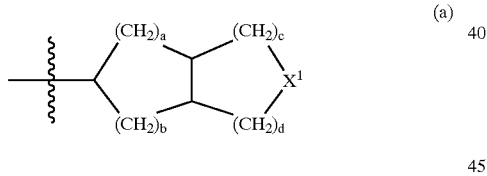

wherein $X^1$ is O, S or —$CH_2$—, a, b, c, and d are each independently selected from an integer ranging from 0 to 2 and $a+b+c+d \leq 5$; or
- $R^1$ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either or which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; except $R^1$ can not be —$CH_2CH_3$; and
- each $R^2$ and $R^3$ is independently H or $C_1$–$C_6$ alkyl except that neither $R^2$ or $R^3$ can be H when R1 is —$CH_2CH_3$; and
- each $R^4$ is independently $C_6$–$C_{10}$ aryl or 5 to 10 membered heterocycle, wherein said aryl and heterocyclic groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n(C_1$–$C_{10}$ alkyl) wherein n is an integer ranging from 0 to 2, and $SO_2NR^2R^3$; and
- $R^5$ is H or $C_1$–$C_{10}$ alkyl, wherein 1 to 3 carbons of said alkyl are optionally replaced by a heteroatom selected from O, S, and $NR^2$, and said alkyl group is optionally replaced by 1 to 3 substituents independantly selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n(C_1$–$C_{10}$ alkyl) wherein n is an integer ranging from 0 to 2, and $SO_2NR^2R^3$; and,
- $R^6$ is H, —$C(O)R^4$, or $C_1$–$C_{18}$ alkanoyl, wherein one or two carbons in the alkyl portion of said alkanoyl may be optionally replaced by a heteroatom selected from O, S, and $NR^2$.

The invention also includes a compound of the formula (10)

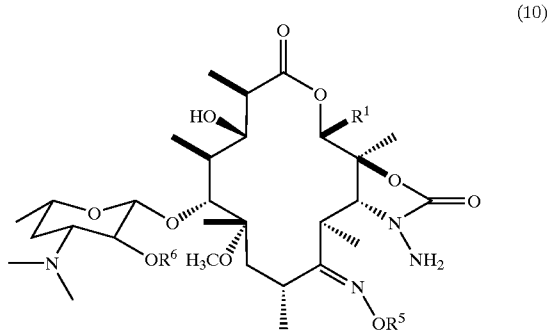

wherein:
- $R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms;
- or $R^1$ is phenyl which may be optionally replaced with one to three groups independently selected from $C_1$–$C_4$ alkyl, $C_1$–$C_4$ alkoxy and $C_1$–$C_4$ alkylthio groups, halogen atoms, hydroxyl groups, trifluoromethyl, and cyano; or

35

$R^1$ may be a formula (a) as shown below

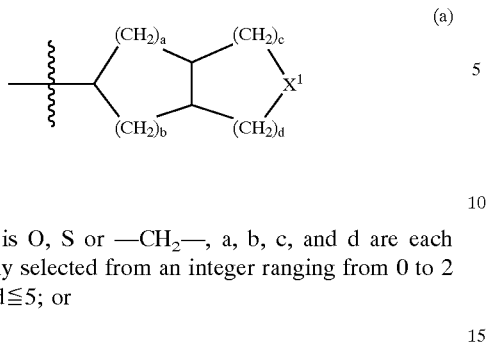

(a)

wherein $X^1$ is O, S or —CH$_2$—, a, b, c, and d are each independently selected from an integer ranging from 0 to 2 and a+b+c+d≦5; or $R^1$ is CH$_2$R$^{24}$, wherein R$^{24}$ is H, C$_1$–C$_8$alkyl, C$_2$–C$_8$alkenyl, C$_2$–C$_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a C$_3$–C$_8$cycloalkyl or C$_5$–C$_8$cycloalkenyl either or which may be optionally replaced by methyl or one to three C$_1$–C$_4$alkyl groups or halo atoms; or a 3 to 6 membered oxygen or sulphur containing heterocyclic ring which may be saturated or fully or partially unsaturated and which may optionally be substituted by one to three C$_1$–C$_4$alkyl groups or halo atoms; or a group of the formula SR$^{23}$ wherein R$^{23}$ is C$_1$–C$_8$alkyl, C$_2$–C$_8$alkenyl, C$_2$–C$_8$alkynyl, C$_3$–C$_8$cycloalkyl, C$_5$–C$_8$cycloalkenyl, phenyl or substituted phenyl wherein the substituent is C$_1$–C$_4$alkyl, C$_1$–C$_4$alkoxy or halo, or a 3 to 6 membered oxygen or sulphur-containing heterocyclic ring which may be saturated, or fully or partially unsaturated and which may optionally be substituted by one to three C$_1$–C$_4$alkyl groups or halo atoms except that R$^1$ is not —CH$_2$CH$_3$; and each R$^2$ and R$^3$ is independently H or C$_1$–C$_6$ alkyl; and each R$^4$ is independently C$_6$–C$_{10}$ aryl or 5 to 10 membered heterocycle, wherein said aryl and heterocycle groups are optionally replaced by 1 to 3 substituents independently selected from the group consisting of —C(O)O(C$_1$–C$_{10}$ alkyl), C$_1$–C$_{10}$ alkoxy, C$_1$–C$_{10}$ alkanoyl, halo, nitro, cyano, 5 to 10 membered heterocycle, C$_6$–C$_{10}$ aryl, C$_1$–C$_{10}$ alkyl, —NR$^2$R$^3$, —S(O)$_n$(C$_1$–C$_{10}$ alkyl) wherein n is an integer ranging from 0 to 2, and SO$_2$NR$^2$R$^3$; and R$^5$ is H or C$_1$–C$_{10}$ alkyl, wherein 1 to 3 carbons of said alkyl may be substituted by a heteroatom selected from O, S, and NR$^2$, and said alkyl group may be substituted by 1 to 3 substituents independantly selected from the group consisting of —C(O)O(C$_1$–C$_{10}$ alkyl), C$_1$–C$_{10}$ alkoxy, C$_1$–C$_{10}$ alkanoyl, halo, nitro, cyano, 5 to 10 membered heterocycle, C$_6$–C$_{10}$ aryl, C$_1$–C$_{10}$ alkyl, —NR$^2$R$^3$, —S(O)$_n$(C$_1$–C$_{10}$ alkyl) wherein n is an integer ranging from 0 to 2, and SO$_2$NR$^2$R$^3$; and R$^6$ is H, —C(O)R$^4$, or C$_1$–C$_{18}$ alkanoyl, wherein one or two carbons in the alkyl portion of said alkanoyl may be optionally replaced by a heteroatom selected from O, S, and NR$^2$.

36

The invention also includes a compound of the formula

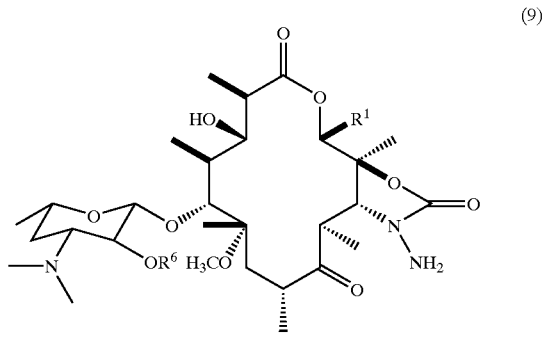

(9)

wherein:
$R^1$ is an alpha-branched C$_3$–C$_8$ alkyl, alkenyl, alkynyl, alkoxyalkyl or alkylthioalkyl group any of which may optionally be substituted by one to three hydroxyl groups; a C$_5$–C$_8$ cycloalkylalkyl group wherein the alkyl group is an alpha-branched C$_2$–C$_5$ alkyl group; a C$_3$–C$_8$ cycloalkyl or C$_5$–C$_8$ cycloalkenyl group, either of which may optionally be substituted by methyl or one to three groups independently selected from hydroxy, C$_1$–C$_4$ alkyl, and halo; or a 3 to 6 membered oxygen or sulphur containing heterocyclic ring which may be saturated, or fully or partially unsaturated and which may optionally be substituted by one to three C$_1$–C$_4$ alkyl groups or halo atoms; or $R^1$ is phenyl which may be optionally replaced with one to three groups independently selected from C$_1$–C$_4$ alkyl, C$_1$–C$_4$ alkoxy and C$_1$–C$_4$ alkylthio groups, halogen atoms, hydroxyl groups, trifluoromethyl, and cyano; or $R^1$ may be a formula (a) as shown below

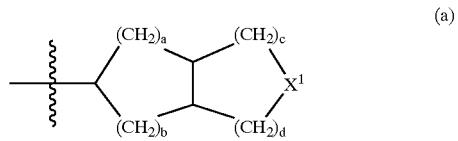

(a)

wherein $X^1$ is O, S or —CH$_2$—, a, b, c, and d are each independently selected from an integer ranging from 0 to 2 and a+b+c+d≦5; or $R^1$ is CH$_2$R$^{24}$, wherein R$^{24}$ is H, C$_1$–C$_8$alkyl, C$_2$–C$_8$alkenyl, C$_2$–C$_8$alkynyl, alkoxyalkyl or alkylthioalkyl containing from 1 to 6 carbon atoms in each alkyl, alkylthiol or alkoxy group wherein any of said alkyl, alkoxy, alkenyl or alkynyl groups may be substituted by one to three hydroxyl groups or by one to three halo atoms; or a C$_3$–C$_8$cycloalkyl or C$_5$–C$_8$cycloalkenyl either or which may be optionally replaced by methyl or one to three C$_1$–C$_4$alkyl groups or halo atoms; or a 3 to 6 membered oxygen or sulphur containing heterocyclic ring which may be saturated or fully or partially unsaturated and which may optionally be substituted by one to three C$_1$–C$_4$alkyl groups or halo atoms; or a group of the formula SR$^{23}$ wherein R$^{23}$ is C$_1$–C$_8$alkyl, C$_2$–C$_8$alkenyl, C$_2$–C$_8$alkynyl, C$_3$–C$_8$cycloalkyl, C$_5$–C$_8$cycloalkenyl, phenyl or substituted phenyl wherein the substituent is C$_1$–C$_4$alkyl, C$_1$–C$_4$alkoxy or halo, or a 3 to 6 membered oxygen or sulphur-containing heterocyclic ring which may be saturated, or fully or partially unsaturated and which may optionally be substituted by one to three $C_1$-$C_4$alkyl groups or halo atoms except that $R^1$ can not —$CH_2CH_3$; and each $R^2$ and $R^3$ is independently H or $C_1$-$C_6$alkyl; and each $R^4$ is independently $C_6$-$C_{10}$ aryl or 5 to 10 membered heterocycle, wherein said aryl and heterocyclic groups are optionally replaced by 1 to 3 substituents independently selected from the group consisting of —C(O)O($C_1$-$C_{10}$ alkyl), $C_1$-$C_{10}$ alkoxy, $C_1$-$C_{10}$ alkanoyl, halo, nitro, cyano, 5 to 10 membered heterocycle, $C_6$-$C_{10}$ aryl, $C_1$-$C_{10}$ alkyl, —$NR^2R^3$, —$S(O)_n$($C_1$-$C_{10}$ alkyl) wherein n is an integer ranging from 0 to 2, and $SO_2NR^2R^3$; and $R^6$ is H, —C(O)$R^4$, or $C_1$-$C_{18}$ alkanoyl, wherein one or two carbons in the alkyl portion of said alkanoyl may be optionally replaced by a heteroatom selected from O, S, and $NR^2$.

The invention also includes a compound of the formula (2)

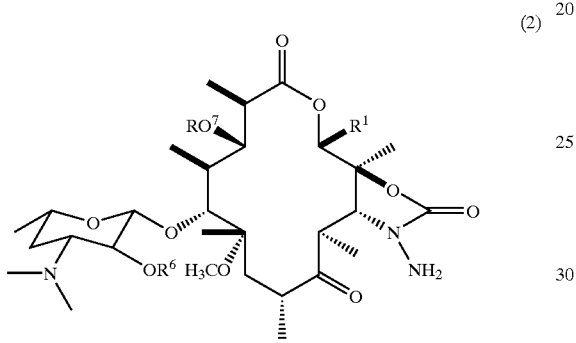

wherein:
$R^1$ is an alpha-branched $C_3$-$C_8$ alkyl, alkenyl, alkynyl, alkoxyalkyl or alkylthioalkyl group any of which may optionally be substituted by one to three hydroxyl groups; a $C_5$-$C_8$ cycloalkylalkyl group wherein the alkyl group is an alpha-branched $C_2$-$C_5$ alkyl group; a $C_3$-$C_8$ cycloalkyl or $C_5$-$C_8$ cycloalkenyl group, either of which may optionally be substituted by methyl or one to three groups independently selected from hydroxy, $C_1$-$C_4$ alkyl, and halo; or a 3 to 6 membered oxygen or sulphur containing heterocyclic ring which may be saturated, or fully or partially unsaturated and which may optionally be substituted by one to three $C_1$-$C_4$ alkyl groups or halo atoms; or $R^1$ is phenyl which may be optionally replaced with one to three groups independently selected from $C_1$-$C_4$ alkyl, $C_1$-$C_4$ alkoxy and $C_1$-$C_4$ alkylthio groups, halogen atoms, hydroxyl groups, trifluoromethyl, and cyano; or $R^1$ can be a formula (a) as shown below (a)

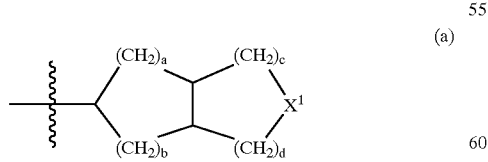

wherein $X^1$ is O, S or —$CH_2$—, a, b, c, and d are each independently selected from an integer ranging from 0 to 2 and $a+b+c+d \leq 5$; or $R^1$ is $CH_2R^{24}$, wherein $R^{24}$ is H, $C_1$-$C_8$alkyl, $C_2$-$C_8$alkenyl, $C_2$-$C_8$alkynyl, alkoxyalkyl or alkylth-ioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$-$C_8$cycloalkyl or $C_5$-$C_8$cycloalkenyl either or which may be optionally replaced by methyl or one to three $C_1$-$C_4$alkyl groups or halo atoms; or a 3 to 6 membered oxygen or sulphur containing heterocyclic ring which may be saturated or fully or partially unsaturated and which may optionally be substituted by one to three $C_1$-$C_4$alkyl groups or halo atoms; or a group of the formula $SR^{23}$ wherein $R^{23}$ is $C_1$-$C_8$alkyl, $C_2$-$C_8$alkenyl, $C_2$-$C_8$alkynyl, $C_3$-$C_8$cycloalkyl, $C_5$-$C_8$cycloalkenyl, phenyl or substituted phenyl wherein the substituent is $C_1$-$C_4$alkyl, $C_1$-$C_4$alkoxy or halo, or a 3 to 6 membered oxygen or sulphur-containing heterocyclic ring which may be saturated, or fully or partially unsaturated and which may optionally be substituted by one to three $C_1$-$C_4$alkyl groups or halo atoms; and each $R^4$ is independently $C_6$-$C_{10}$ aryl or 5 to 10 membered heterocycle, wherein said aryl and heterocyclic groups are optionally replaced by 1 to 3 substituents independently selected from the group consisting of —C(O)O($C_1$-$C_{10}$ alkyl), $C_1$-$C_{10}$ alkoxy, $C_1$-$C_{10}$ alkanoyl, halo, nitro, cyano, 5 to 10 membered heterocycle, $C_6$-$C_{10}$ aryl, $C_1$-$C_{10}$ alkyl, —$NR^2R^3$, —$S(O)_n$($C_1$-$C_{10}$ alkyl) wherein n is an integer ranging from 0 to 2, and $SO_2NR^2R^3$; and $R^6$ is H, —C(O)$R^4$, or $C_1$-$C_{18}$ alkanoyl, wherein one or two carbons in the alkyl portion of said alkanoyl may be optionally replaced by a heteroatom selected from O, S, and $NR^2$.

$R^7$ is a radical of formula

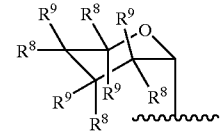

wherein each $R^8$ and $R^9$ are independently hydrogen, hydroxy, $C_1$-$C_6$ alkoxy, —OC(O)$R^4$, —OC(O)NHNH$_2$, —OSi($R^{10}$)$_3$, or $C_1$-$C_{18}$ O-alkanoyl, wherein one or two carbons in the alkyl portion of said alkanoyl may be optionally replaced by a heteroatom selected from O, S, and $NR^2$; and $R^8$ & $R^9$ may be taken together to form

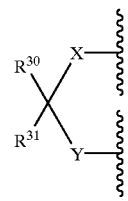

wherein:
X=O or S
Y=O or S
$R^{30}$, and $R^{31}$=H, $C_1$-$C_6$ alkyl, $C_6$-$C_{10}$ aryl, or $R^{30}$ and $R^{31}$ taken together form =O or =S or $R^8$ & $R^9$ can be taken together to form

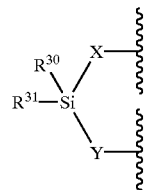

except that when $R^1$ is —CH$_2$CH$_3$, $R^7$ can not be a radical of the formula

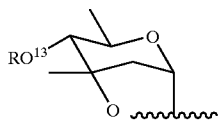

wherein $R^{13}$ is hydrogen, C(O)R$^4$, —Si(R$^{10}$)$_3$, $C_1$–$C_{10}$ alkyl, or $C_1$–$C_{18}$ alkanoyl, wherein one or two carbons in the alkyl portion of said alkyl or alkanoyl may be optionally replaced by a heteroatom selected from O, S, and NR$^2$; and each $R^{10}$ is independently $C_1$–$C_{10}$ alkyl or $C_6$–$C_{10}$ aryl.

The invention also includes a compound of the formula

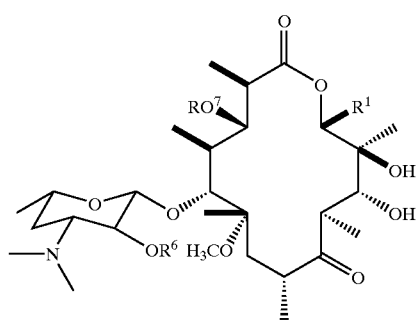

(1)

wherein:

$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from $C_1$–$C_4$ alkyl, $C_1$–$C_4$ alkoxy and $C_1$–$C_4$ alkylthio groups, halogen atoms, hydroxyl groups, trifluoromethyl, and cyano; or $R^1$ may be a formula (a) as shown below

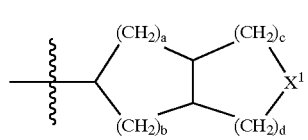

(a)

wherein $X^1$ is O, S or —CH$_2$—, a, b, c, and d are each independently selected from an integer ranging from 0 to 2 and a+b+c+d≦5; or $R^1$ is CH$_2$R$^{24}$, wherein R$^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either or which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula SR$^{23}$ wherein R$^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and each $R^4$ is independently $C_6$–$C_{10}$ aryl or 5 to 10 membered heterocycle, wherein said aryl and heterocyclic groups are optionally replaced by 1 to 3 substituents independently selected from the group consisting of —C(O)O(C$_1$–C$_{10}$ alkyl), $C_1$–$C_{10}$ alkoxy, $C_1$–$C_{10}$ alkanoyl, halo, nitro, cyano, 5 to 10 membered heterocycle, $C_6$–$C_6$ aryl, $C_1$–$C_{10}$ alkyl, —NR$^2$R$^3$, —S(O)$_n$(C$_1$–C$_{10}$ alkyl) wherein n is an integer ranging from 0 to 2, and SO$_2$NR$^2$R$^3$; and $R^6$ is H, —C(O)R$^4$, or $C_1$–$C_{18}$ alkanoyl, wherein one or two carbons in the alkyl portion of said alkanoyl may be optionally replaced by a heteroatom selected from O, S, and NR$^2$; and $R^7$ is a radical of formula

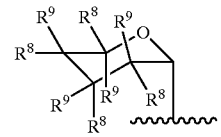

wherein each $R^8$ and $R^9$ are independently hydrogen, hydroxy, $C_1$–$C_6$ alkoxy, —OC(O)R$^4$, —OC(O)NHNH$_2$, —OSi(R$^{10}$)$_3$, or $C_1$–$C_{18}$ O-alkanoyl, wherein one or two carbons in the alkyl portion of said alkanoyl may be optionally replaced by a heteroatom selected from O, S, and NR$^2$; except when $R^1$ is —CH$_2$CH$_3$, $R^7$ can not be a radical of the formula

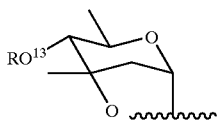

wherein $R^{13}$ is hydrogen, $C(O)R^4$, $-Si(R^{10})_3$, $C_1-C_{10}$ alkyl, or $C_1-C_{18}$ alkanoyl, wherein one or two carbons in the alkyl portion of said alkyl or alkanoyl may be optionally replaced by a heteroatom selected from O, S, and $NR^2$; and $R^8$ & $R^9$ may be taken together to form

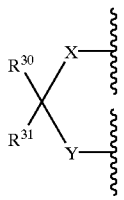

wherein:
X=O or S
Y=O or S
$R^{30}$, and $R^{31}$=H, $C_1-C_6$ alkyl, $C_6-C_{10}$ aryl, or $R^{30}$, and $R^{31}$ taken together form =O or =S or $R^8$ & $R^9$ can be taken together to form

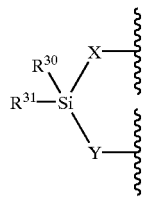

and each $R^{10}$ is independently $C_1-C_{10}$ alkyl or $C_6-C_{10}$ aryl.

The invention also includes a compound of the formula (34)

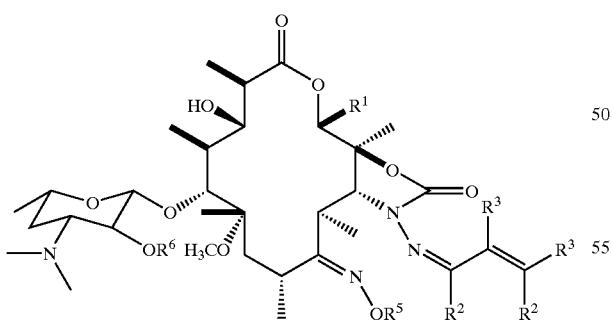

wherein:
$R^1$ is an alpha-branched $C_3-C_8$ alkyl, alkenyl, alkynyl, alkoxyalkyl or alkylthioalkyl group any of which may optionally be substituted by one to three hydroxyl groups; a $C_5-C_8$ cycloalkylalkyl group wherein the alkyl group is an alpha-branched $C_2-C_5$ alkyl group; a $C_3-C_8$ cycloalkyl or $C_5-C_8$ cycloalkenyl group, either of which may optionally be substituted by methyl or one to three groups independently selected from hydroxy, $C_1-C_4$ alkyl, and halo; or a 3 to 6 membered oxygen or sulphur containing heterocyclic ring which may be saturated, or fully or partially unsaturated and which may optionally be substituted by one to three $C_1-C_4$ alkyl groups or halo atoms; or $R^1$ is phenyl which may be optionally replaced with one to three groups independently selected from $C_1-C_4$ alkyl, $C_1-C_4$ alkoxy and $C_1-C_4$ alkylthio groups, halogen atoms, hydroxyl groups, trifluoromethyl, and cyano; or $R^1$ may be a formula (a) as shown below (a)

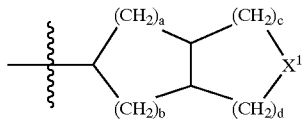

wherein $X^1$ is O, S or $-CH_2-$, a, b, c, and d are each independently selected from an integer ranging from 0 to 2 and $a+b+c+d \leq 5$; or $R^1$ is $CH_2R^{24}$, wherein $R^{24}$ is H, $C_1-C_8$alkyl, $C_2-C_8$alkenyl, $C_2-C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3-C_8$cycloalkyl or $C_5-C_8$cycloalkenyl either or which may be optionally replaced by methyl or one to three $C_1-C_4$alkyl groups or halo atoms; or a 3 to 6 membered oxygen or sulphur containing heterocyclic ring which may be saturated or fully or partially unsaturated and which may optionally be substituted by one to three $C_1-C_4$alkyl groups or halo atoms; or a group of the formula $SR^{23}$ wherein $R^{23}$ is $C_1-C_8$alkyl, $C_2-C_8$alkenyl, $C_2-C_8$alkynyl, $C_3-C_8$cycloalkyl, $C_5-C_8$cycloalkenyl, phenyl or substituted phenyl wherein the substituent is $C_1-C_4$alkyl, $C_1-C_4$alkoxy or halo, or a 3 to 6 membered oxygen or sulphur-containing heterocyclic ring which may be saturated, or fully or partially unsaturated and which may optionally be substituted by one to three $C_1-C_4$alkyl groups or halo atoms; except that $R^1$ can not be $-CH_2CH_3$, and each $R^2$ and $R^3$ is independently H or $C_1-C_6$ alkyl; and, each $R^4$ is independently $C_6-C_{10}$ aryl or 5 to 10 membered heterocycle, wherein said aryl and heterocyclic groups are optionally replaced by 1 to 3 substituents independently selected from the group consisting of $-C(O)O(C_1-C_{10}$ alkyl), $C_1-C_{10}$ alkoxy, $C_1-C_{10}$ alkanoyl, halo, nitro, cyano, 5 to 10 membered heterocycle, $C_6-C_{10}$ aryl, $C_1-C_{10}$ alkyl, $-NR^2R^3$, $-S(O)_n(C_1-C_{10}$ alkyl) wherein n is an integer ranging from 0 to 2, and $SO_2NR^2R^3$; and $R^5$ is H or $C_1-C_{10}$ alkyl, wherein 1 to 3 carbons of said alkyl are optionally replaced by a heteroatom selected from O, S, and $NR^2$, and said alkyl group is optionally replaced by 1 to 3 substituents independantly selected from the group consisting of $-C(O)O(C_1-C_{10}$ alkyl), $C_1-C_{10}$ alkoxy, $C_1-C_{10}$ alkanoyl, halo, nitro, cyano, 5 to 10 membered heterocycle, $C_6-C_{10}$ aryl, $C_1-C_{10}$ alkyl, $-NR^2R^3$, $-S(O)_n(C_1-C_{10}$ alkyl) wherein n is an integer ranging from 0 to 2, and $SO_2NR^2R^3$; and $R^6$ is H, $-C(O)R^4$, or $C_1-C_{18}$ alkanoyl, wherein one or two carbons in the alkyl portion of said alkanoyl may be optionally replaced by a heteroatom selected from O, S, and $NR^2$.

The invention also includes a compound of the formula

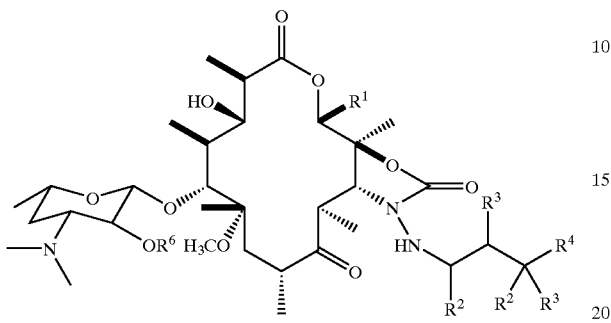

(19)

wherein:

$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from $C_1$–$C_4$ alkyl, $C_1$–$C_4$ alkoxy and $C_1$–$C_4$ alkylthio groups, halogen atoms, hydroxyl groups, trifluoromethyl, and cyano; or $R^1$ may be a formula (a) as shown below

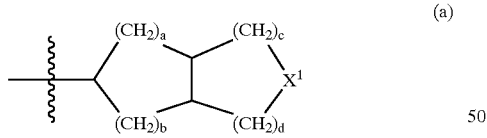

(a)

wherein $X^1$ is O, S or —$CH_2$—, a, b, c, and d are each independently selected from an integer ranging from 0 to 2 and a+b+c+d$\leq$5; or $R^1$ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either or which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and each $R^2$ and $R^3$ is independently H or $C_1$–$C_6$ alkyl except that $R^2$ and $R^3$ can not both be H when $R^1$ is —$CH_2CH_3$; and each $R^4$ is independently $C_6$–$C_{10}$ aryl or 5 to 10 membered heterocycle, wherein said aryl and heterocycle groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n$($C_1$–$C_{10}$ alkyl) wherein n is an integer ranging from 0 to 2, and $SO_2NR^2R^3$; and $R^6$ is H, —C(O)$R^4$, or $C_1$–$C_{18}$ alkanoyl, wherein one or two carbons in the alkyl portion of said alkanoyl may be optionally replaced by a heteroatom selected from O, S, and $NR^2$.

The invention also includes a compound of formula

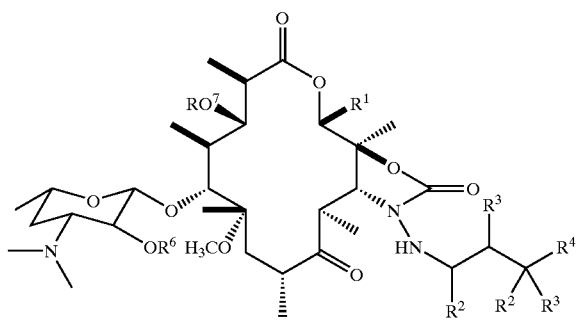

(17)

wherein:

$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from $C_1$–$C_4$ alkyl, $C_1$–$C_4$ alkoxy and $C_1$–$C_4$ alkylthio groups, halogen atoms, hydroxyl groups, trifluoromethyl, and cyano; or $R^1$ may be a formula (a) as shown below

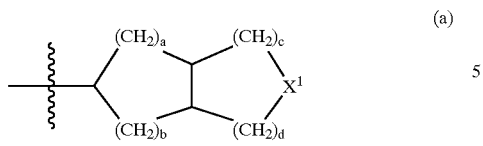

wherein $X^1$ is O, S or —CH$_2$—, a, b, c, and d are each independently selected from an integer ranging from 0 to 2 and a+b+c+d≦5; or $R^1$ is CH$_2$R$^{24}$, wherein R$^{24}$ is H, C$_1$–C$_8$alkyl, C$_2$–C$_8$alkenyl, C$_2$–C$_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a C$_3$–C$_8$cycloalkyl or C$_5$–C$_8$cycloalkenyl either of which may be optionally replaced by methyl or one to three C$_1$–C$_4$alkyl groups or halo atoms; or a 3 to 6 membered oxygen or sulphur containing heterocyclic ring which may be saturated or fully or partially unsaturated and which may optionally be substituted by one to three C$_1$–C$_4$alkyl groups or halo atoms; or a group of the formula SR$^{23}$ wherein R$^{23}$ is C$_1$–C$_8$alkyl, C$_2$–C$_8$alkenyl, C$_2$–C$_8$alkynyl, C$_3$–C$_8$cycloalkyl, C$_5$–C$_8$cycloalkenyl, phenyl or sustituted phenyl wherein the substituent is C$_1$–C$_4$alkyl, C$_1$–C$_4$alkoxy or halo, or a 3 to 6 membered oxygen or sulphur-containing heterocyclic ring which may be saturated, or fully or partially unsaturated and which may optionally be substituted by one to three C$_1$–C$_4$alkyl groups or halo atoms; and each R$^2$ and R$^3$ is independently H or C$_1$–C$_6$ alkyl except that neither R$^2$ nor R$^3$ can be H when R$^1$ is —CH$_2$CH$_3$; and each R$^4$ is independently C$_6$–C$_{10}$ aryl or 5 to 10 membered heterocycle, wherein said aryl and heterocyllC groups are optionally replaced by 1 to 3 substituents independently selected from the group consisting of —C(O)O(C$_1$–C$_{10}$ alkyl), C$_1$–C$_{10}$ alkoxy, C$_1$–C$_{10}$ alkanoyl, halo, nitro, cyano, 5 to 10 membered heterocycle, C$_6$–C$_{10}$ aryl, C$_1$–C$_{10}$ alkyl, —NR$^2$R$^3$, —S(O)n(C$_1$–C$_{10}$ alkyl) wherein n is an integer ranging from 0 to 2, and SO$_2$NR$^2$R$^3$; and $R^6$ is H, —C(O)R$^4$, or C$_1$–C$_{18}$ alkanoyl, wherein one or two carbons in the alkyl portion of said alkanoyl may be optionally replaced by a heteroatom selected from O, S, and NR$^2$; and $R^7$ is a radical of formula

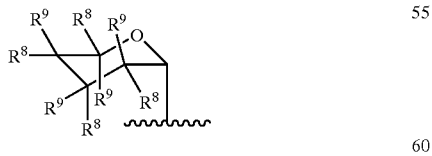

wherein each R$^8$ and R$^9$ are independently hydrogen, hydroxy, C$_1$–C$_6$ alkoxy, —OC(O)R$^4$, —OC(O)NHNH$_2$, —OSi(R$^{10}$)$_3$, or C$_1$–C$_{18}$-alkanoyl, wherein one or two carbons in the alkyl portion of said alkanoyl may be optionally replaced by a heteroatom selected from O, S, and NR$^2$; and $R^8$ & $R^9$ may be taken together to form

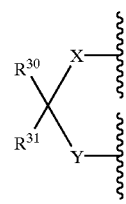

wherein:

X=O or S

Y=O or S

R$^{30}$, and R$^{31}$=H, C$_1$–C$_6$ alkyl, C$_6$–C$_{10}$ aryl, or R$^{30}$ and R$^{31}$ taken together form =O or =S or R$^8$ & R$^9$ can be taken together to form

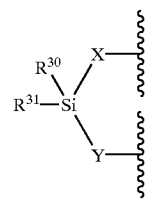

and each R$^{10}$ is independently C$_1$–C$_{10}$ alkyl or C$_6$–C$_{10}$ aryl.

The invention also includes a compound of formula

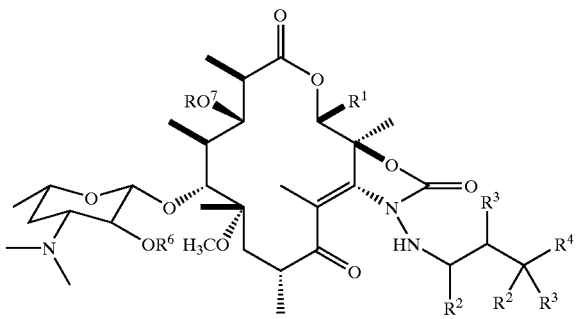

wherein:

$R^1$ is an alpha-branched C$_3$–C$_8$ alkyl, alkenyl, alkynyl, alkoxyalkyl or alkylthioalkyl group any of which may optionally be substituted by one to three hydroxyl groups; a C$_5$–C$_8$ cycloalkylalkyl group wherein the alkyl group is an alpha-branched C$_2$–C$_5$ alkyl group; a C$_3$–C$_8$ cycloalkyl or C$_5$–C$_8$ cycloalkenyl group, either of which may optionally be substituted by methyl or one to three groups independently selected from hydroxy, C$_1$–C$_4$ alkyl, and halo; or a 3 to 6 membered oxygen or sulphur containing heterocyclic ring which may be saturated, or fully or partially unsaturated and which may optionally be substituted by one to three C$_1$–C$_4$ alkyl groups or halo atoms; or $R^1$ is phenyl which may be optionally replaced with one to three groups independently selected from C$_1$–C$_4$ alkyl, C$_1$–C$_4$ alkoxy and C$_1$–C$_4$ alkylthio groups, halogen atoms, hydroxyl groups, trifluoromethyl, and cyano; or $R^1$ may be a formula (a) as shown below

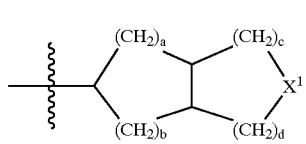

(a)

wherein $X^1$ is O, S or —CH$_2$—, a, b, c, and d are each independently selected from an integer ranging from 0 to 2 and a+b+c+d≦5; or $R^1$ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either or which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and each $R^2$ and $R^3$ is independently H or $C_1$–$C_6$ alkyl; except that neither $R^2$ or $R^3$ can be H when $R^1$ is $CH_2CH_3$ and each $R^4$ is independently $C_6$–$C_{10}$ aryl or 5 to 10 membered heterocycle, wherein said aryl and heterocyclic groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —NR$^2$R$^3$, —S(O)$_n$($C_1$–$C_{10}$ alkyl) wherein n is an integer ranging from 0 to 2, and SO$_2$NR$^2$R$^3$; and $R^6$ is H, —C(O)R$^4$, or $C_1$–$C_{18}$ alkanoyl, wherein one or two carbons in the alkyl portion of said alkanoyl may be optionally replaced by a heteroatom selected from O, S, and NR$^2$; and $R^7$ is a radical of formula

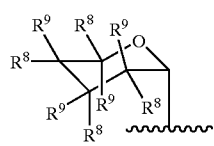

wherein each $R^8$ and $R^9$ are independently hydrogen, hydroxy, $C_1$–$C_6$ alkoxy, —OC(O)R$^4$, —OC(O)NHNH$_2$, —OSi(R$^{10}$)$_3$, or $C_1$–$C_{18}$ O-alkanoyl, wherein one or two carbons in the alkyl portion of said alkanoyl may be optionally replaced by a heteroatom selected from O, S, and NR$^2$; and $R^8$ & $R^9$ may be taken together to form

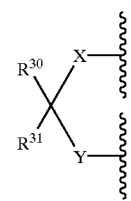

wherein:
X=O or S
Y=O or S
$R^{30}$, and $R^{31}$=H, $C_1$–$C_6$ alkyl, $C_6$–$C_{10}$ aryl,
or $R^{30}$ and $R^{31}$ taken together form =O or =S
or $R^8$ & $R^9$ can be taken together to form

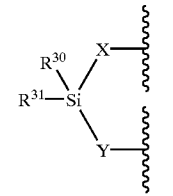

and each $R^{10}$ is independently $C_1$–$C_{10}$ alkyl or $C_6$–$C_{10}$ aryl;
with the proviso that when $R^1$ is —CH$_2$CH$_3$ and $R^7$ is a radical of the formula

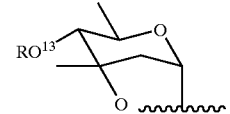

wherein $R^{13}$ is hydrogen, C(O)R$^4$, —Si(R$^{10}$)$_3$, $C_1$–$C_{10}$ alkyl, or $C_1$–$C_{18}$ alkanoyl, wherein one or two carbons in the alkyl portion of said alkyl or alkanoyl may be optionally replaced by a heteroatom selected from O, S, and NR$^2$, than one of $R^2$ and $R^3$ must be other than H, The invention also includes a compound of the formula

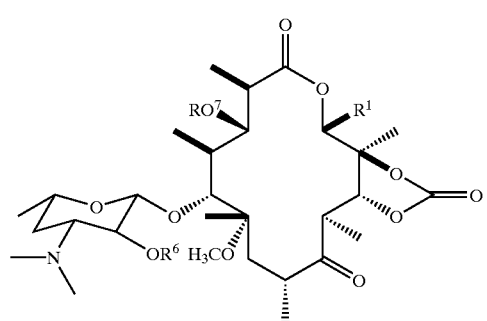

(3)

wherein:
$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from $C_1$–$C_4$ alkyl, $C_1$–$C_4$ alkoxy and $C_1$–$C_4$ alkylthio groups, halogen atoms, hydroxyl groups, trifluoromethyl, and cyano;

$R^3$ is a formula (a) as shown below

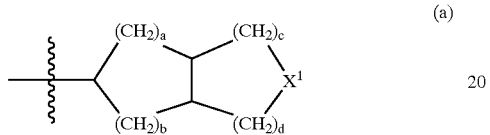

(a)

wherein $X^1$ is O, S or —$CH_2$—, a, b, c, and d are each independently selected from an integer ranging from 0 to 2 and a+b+c+d$\leq$5; or $R^3$ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either or which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkeny, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and each $R^4$ is independently $C_6$–$C_{10}$ aryl or 5 to 10 membered heterocycle, wherein said aryl and heterocyclic groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —S(O)$_n$($C_1$–$C_{10}$ alkyl) wherein n is an integer ranging from 0 to 2, and $SO_2NR^2R^3$; and $R^6$ is H, —C(O)$R^4$, or $C_1$–$C_{18}$ alkanoyl, wherein one or two carbons in the alkyl portion of said alkanoyl may be optionally replaced by a heteroatom selected from O, S, and $NR^2$; and $R^7$ is a radical of formula

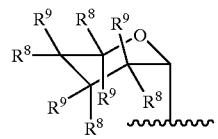

wherein each $R^8$ and $R^9$ are independently hydrogen, hydroxy, $C_1$–$C_6$ alkoxy, —OC(O)$R^4$, —OC(O)NHNH$_2$, —OSi($R^{10}$)$_3$, or $C_1$–$C_{18}$ O-alkanoyl, wherein one or two carbons in the alkyl portion of said alkanoyl may be optionally replaced by a heteroatom selected from O, S, and $NR^2$; and $R^8$ & $R^9$ may be taken together to form

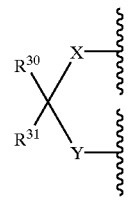

wherein:

X=O or S

Y=O or S $R^{30}$, and $R^{31}$=H, $C_1$–$C_6$ alkyl, $C_6$–$C_{10}$ aryl, or $R^{30}$ and $R^{31}$ taken together form =O or =S or $R^8$ & $R^9$ can be taken together to form

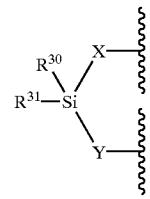

and each $R^{10}$ is independently $C_1$–$C_{10}$ alkyl or $C_6$–$C_{10}$ aryl;

with the proviso that when $R^1$ is —$CH_2CH_3$ and $R^2$ and $R^3$ are each independently H, than $R^7$ can not be a radical of the formula

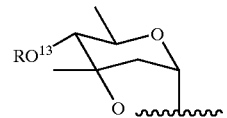

wherein $R^{13}$ is hydrogen, C(O)$R^4$, —Si($R^{10}$)$_3$, $C_1$–$C_{10}$ alkyl, or $C_1$–$C_{18}$ alkanoyl, wherein one or two carbons in the alkyl portion of said alkyl or alkanoyl may be optionally replaced by a heteroatom selected from O, S, and $NR^2$ The invention also includes to a compound of the formula (4)

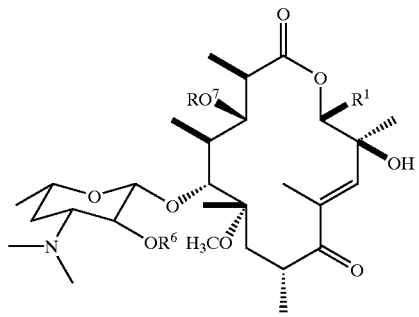

wherein:
- $R^1$ is an alpha-branched $C_3-C_8$ alkyl, alkenyl, alkynyl, alkoxyalkyl or alkylthioalkyl group any of which may optionally be substituted by one to three hydroxyl groups; a $C_5-C_8$ cycloalkylalkyl group wherein the alkyl group is an alpha-branched $C_2-C_5$ alkyl group; a $C_3-C_8$ cycloalkyl or $C_5-C_8$ cycloalkenyl group, either of which may optionally be substituted by methyl or one to three groups independently selected from hydroxy, $C_1-C_4$ alkyl, and halo; or a 3 to 6 membered oxygen or sulphur containing heterocyclic ring which may be saturated, or fully or partially unsaturated and which may optionally be substituted by one to three $C_1-C_4$ alkyl groups or halo atoms; or
- $R^1$ is phenyl which may be optionally replaced with one to three groups independently selected from $C_1-C_4$ alkyl, $C_1-C_4$ alkoxy and $C_1-C_4$ alkylthio groups, halogen atoms, hydroxyl groups, trifluoromethyl, and cyano; or
- $R^1$ can be a formula (a) as shown below

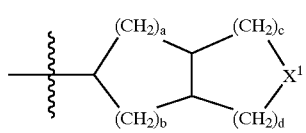

(a)

wherein $X^1$ is O, S or $-CH_2-$, a, b, c, and d are each independently selected from an integer ranging from 0 to 2 and $a+b+c+d \leq 5$; or
- $R^1$ is $CH_2R^{24}$, wherein $R^{24}$ is H, $C_1-C_8$ alkyl, $C_2-C_8$ alkenyl, $C_2-C_8$ alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3-C_8$ cycloalkyl or $C_5-C_8$ cycloalkenyl either of which may be optionally replaced by methyl or one to three $C_1-C_4$ alkyl groups or halo atoms; or a 3 to 6 membered oxygen or sulphur containing heterocyclic ring which may be saturated or fully or partially unsaturated and which may optionally be substituted by one to three $C_1-C_4$ alkyl groups or halo atoms; or a group of the formula $SR^{23}$ wherein $R^{23}$ is $C_1-C_8$ alkyl, $C_2-C_8$ alkenyl, $C_2-C_8$ alkynyl, $C_3-C_8$ cycloalkyl, $C_5-C_8$ cycloalkenyl, phenyl or substituted phenyl wherein the substituent is $C_1-C_4$ alkyl, $C_1-C_4$ alkoxy or halo, or a 3 to 6 membered oxygen or sulphur-containing heterocyclic ring which may be saturated, or fully or partially unsaturated and which may optionally be substituted by one to three $C_1-C_4$ alkyl groups or halo atoms; and
- each $R^4$ is independently $C_6-C_{10}$ aryl or 5 to 10 membered heterocycle, wherein said aryl and heterocyclic groups are optionally replaced by 1 to 3 substituents independently selected from the group consisting of $-C(O)O(C_1-C_{10}$ alkyl), $C_1-C_{10}$ alkoxy, $C_1-C_{10}$ alkanoyl, halo, nitro, cyano, 5 to 10 membered heterocycle, $C_6-C_{10}$ aryl, $C_1-C_{10}$ alkyl, $-NR^2R^3$, $-S(O)_n(C_1-C_{10}$ alkyl) wherein n is an integer ranging from 0 to 2, and $SO_2NR^2R^3$; and
- $R^6$ is H, $-C(O)R^4$, or $C_1-C_{18}$ alkanoyl, wherein one or two carbons in the alkyl portion of said alkanoyl may be optionally replaced by a heteroatom selected from O, S, and $NR^2$, and
- $R^7$ is a radical of formula

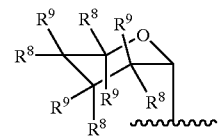

wherein each $R^8$ and $R^9$ are independently hydrogen, hydroxy, $C_1-C_6$ alkoxy, $-OC(O)R^4$, $-OC(O)NHNH_2$, $-OSi(R^{10})_3$, or $C_1-C_{18}$ O-alkanoyl, wherein one or two carbons in the alkyl portion of said alkanoyl may be optionally replaced by a heteroatom selected from O, S, and $NR^2$; and, $R^8$ & $R^9$ may be taken together to form

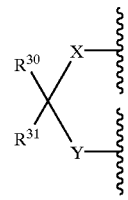

wherein:

X=O or S

Y=O or S $R^{30}$, and $R^{31}$=H, $C_1-C_6$ alkyl, $C_6-C_{10}$ aryl, or $R^{30}$ and $R^{31}$ taken together form =O or =S or $R^8$ & $R^9$ can be taken together to form

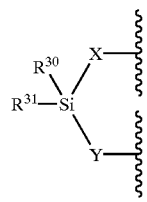

each $R^{10}$ is independently $C_1-C_{10}$ alkyl or $C_6-C_{10}$ aryl;

with the proviso that when $R^1$ is $-CH_2CH_3$, $R^7$ can not be a radical of the formula

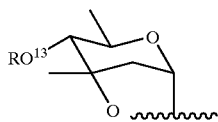

wherein $R^3$ is hydrogen, $C(O)R^4$, —$Si(R^{10})_3$, $C_1$–$C_{10}$ alkyl, or $C_1$–$C_{18}$ alkanoyl, wherein one or two carbons in the alkyl portion of said alkyl or alkanoyl may be optionally replaced by a heteroatom selected from O, S, and $NR^2$.

The invention also includes a compound of the formula

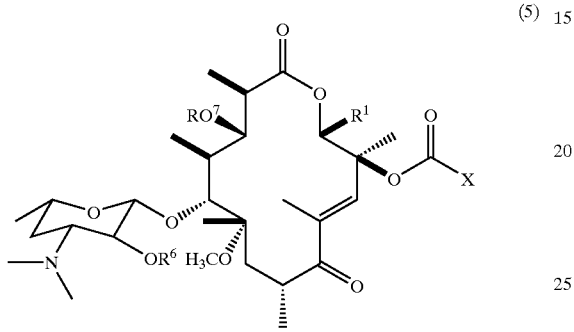

(5)

wherein:

$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from $C_1$–$C_4$ alkyl, $C_1$–$C_4$ alkoxy and $C_1$–$C_4$ alkylthio groups, halogen atoms, hydroxyl groups, trifluoromethyl, and cyano; or $R^1$ may be a formula (a) as shown below

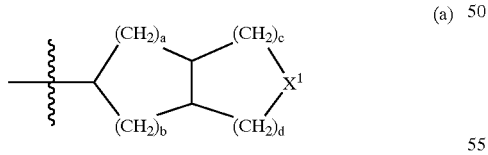

(a)

wherein $X^1$ is O, S or —$CH_2$—, a, b, c, and d are each independently selected from an integer ranging from 0 to 2 and $a+b+c+d \leq 5$; or $R^1$ is $CH_2R^{24}$, wherein $R^{24}$ is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$ cycloalkyl or $C_5$–$C_8$ cycloalkenyl either of which may be optionally replaced by methyl or one to three $C_1$–$C_4$ alkyl groups or halo atoms; or a 3 to 6 membered oxygen or sulphur containing heterocyclic ring which may be saturated or fully or partially unsaturated and which may optionally be substituted by one to three $C_1$–$C_4$ alkyl groups or halo atoms; or a group of the formula $SR^{23}$ wherein $R^{23}$ is $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo, or a 3 to 6 membered oxygen or sulphur-containing heterocyclic ring which may be saturated, or fully or partially unsaturated and which may optionally be substituted by one to three $C_1$–$C_4$ alkyl groups or halo atoms; and each $R^4$ is independently $C_6$–$C_{10}$ aryl or 5 to 10 membered heterocycle, wherein said aryl and heterocyclic groups are optionally replaced by 1 to 3 substituents independently selected from the group consisting of —$C(O)O(C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n(C_1$–$C_{10}$ alkyl) wherein n is an integer ranging from 0 to 2, and $SO_2NR^2R^3$; and $R^6$ is H, —$C(O)R^4$, or $C_1$–$C_{18}$ alkanoyl, wherein one or two carbons in the alkyl portion of said alkanoyl may be optionally replaced by a heteroatom selected from O, S, and $NR^2$; and $R^7$ is a radical of formula

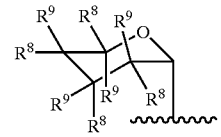

wherein each $R^8$ and $R^9$ are independently hydrogen, hydroxy, $C_1$–$C_6$ alkoxy, —$OC(O)R^4$, —$OC(O)NHNH_2$, —$OSi(R^{10})_3$, or $C_1$–$C_{18}$ O-alkanoyl, wherein one or two carbons in the alkyl portion of said alkanoyl may be optionally replaced by a heteroatom selected from O, S, and $NR^2$; and $R^8$ & $R^9$ may be taken together to form

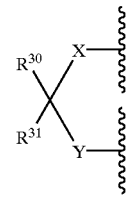

wherein:

X=O or S

Y=O or S $R^{30}$, and $R^{31}$=H, $C_1$–$C_6$ alkyl, $C_6$–$C_{10}$ aryl, or $R^{30}$ and $R^{31}$ taken together form =O or =S $R^8$ & $R^9$ can be taken together to form

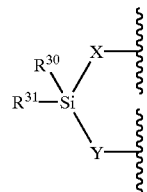

each $R^{10}$ is independently $C_1$–$C_{10}$ alkyl or $C_6$–$C_{10}$ aryl, and

X is imidazole, 1,2,4-triazole, hydroxybenzotriazole, or benzotriazole.

with the proviso that when $R^1$ is —$CH_2CH_3$ and $R^7$ is a radical of the formula

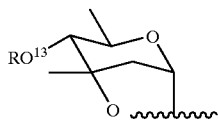

wherein $R^{13}$ is hydrogen, $C(O)R^4$, —$Si(R^{10})_3$, $C_1$–$C_{10}$ alkyl, or $C_1$–$C_{18}$ alkanoyl, wherein one or two carbons in the alkyl portion of said alkyl or alkanoyl may be optionally replaced by a heteroatom selected from O, S, and $NR^2$, than X must be other than imidazole.

The invention also includes a compound of the formula (6)

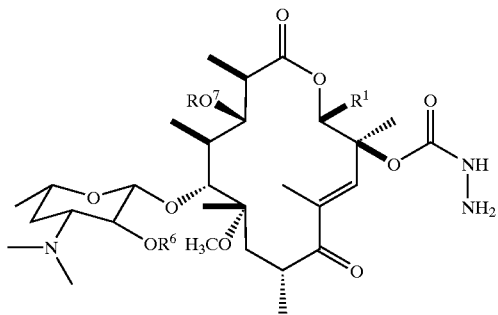

wherein:

$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from $C_1$–$C_4$ alkyl, $C_1$–$C_4$ alkoxy and $C_1$–$C_4$ alkylthio groups, halogen atoms, hydroxyl groups, trifluoromethyl, and cyano; or $R^1$ may be a formula (a) as shown below (a)

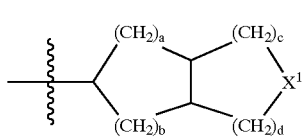

wherein $X^1$ is O, S or —$CH_2$—, a, b, c, and d are each independently selected from an integer ranging from 0 to 2 and a+b+c+d$\leq$5; or $R^3$ is $CH_2R^{24}$, wherein $R^{24}$ is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$ cycloalkyl or $C_5$–$C_8$ cycloalkenyl either of which may be optionally replaced by methyl or one to three $C_1$–$C_4$ alkyl groups or halo atoms; or a 3 to 6 membered oxygen or sulphur containing heterocyclic ring which may be saturated or fully or partially unsaturated and which may optionally be substituted by one to three $C_1$–$C_4$ alkyl groups or halo atoms; or a group of the formula $SR^{23}$ wherein $R^{23}$ is $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo, or a 3 to 6 membered oxygen or sulphur-containing heterocyclic ring which may be saturated, or fully or partially unsaturated and which may optionally be substituted by one to three $C_1$–$C_4$ alkyl groups or halo atoms; and each $R^4$ is independently $C_6$–$C_{10}$ aryl or 5 to 10 membered heterocycle, wherein said aryl and heterocyclic groups are optionally replaced by 1 to 3 substituents independently selected from the group consisting of —$C(O)O(C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n(C_1$–$C_{10}$ alkyl) wherein n is an integer ranging from 0 to 2, and $SO_2NR^2R^3$; and $R^6$ is H, —$C(O)R^4$, or $C_1$–$C_8$ alkanoyl, wherein one or two carbons in the alkyl portion of said alkanoyl may be optionally replaced by a heteroatom selected from O, S, and $NR^2$; and $R^7$ is a radical of formula

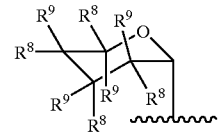

wherein each $R^8$ and $R^9$ are independently hydrogen, hydroxy, $C_1$–$C_6$ alkoxy, —$OC(O)R^4$, —$OC(O)NHNH_2$, —$OSi(R^{10})_3$, or $C_1$–$C_{18}$ O-alkanoyl, wherein one or two carbons in the alkyl portion of said alkanoyl may be optionally replaced by a heteroatom selected from O, S, and $NR^2$; and $R^8$ & $R^9$ may be taken together to form

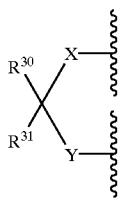

wherein:
X=O or S
Y=O or S
$R^{30}$, and $R^{31}$=H, $C_1$–$C_6$ alkyl, $C_6$–$C_{10}$ aryl, or $R^{30}$ and $R^{31}$ taken together form =O or =S or $R^8$ & $R^9$ can be taken together to form

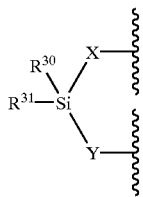

each $R^{10}$ is independently $C_1$–$C_{10}$ alkyl or $C_6$–$C_{10}$ aryl;
with the proviso that when $R^3$ is —CH$_2$CH$_3$, $R^7$ can not be a radical of the formula

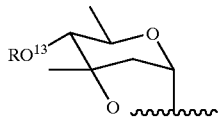

wherein $R^3$ is hydrogen, C(O)$R^4$, —Si($R^{10}$)$_3$, $C_1$–$C_{10}$ alkyl, or $C_1$–$C_8$ alkanoyl, wherein one or two carbons in the alkyl portion of said alkyl or alkanoyl may be optionally replaced by a heteroatom selected from O, S, and NR$^2$.

The invention also includes a compound of formula (16)

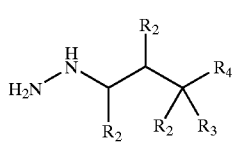

wherein:
each $R^2$ and $R^3$ is independently H or $C_1$–$C_6$ alkyl; and,
each $R^4$ is independently $C_6$–$C_{10}$ aryl or 5 to 10 membered heterocycle, wherein said aryl and heterocyclic groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —NR$^2$R$^3$, —S(O)$_n$($C_1$–$C_{10}$ alkyl) wherein n is an integer ranging from 0 to 2, and SO$_2$NR$^2$R$^3$.

The invention also includes a compound of formula (32)

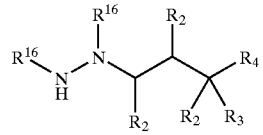

wherein:
each $R^2$ and $R^3$ is independently H or $C_1$–$C_6$ alkyl; and
each $R^4$ is independently $C_6$–$C_{10}$ aryl or 5 to 10 membered heterocycle, wherein said aryl and heterocyclic groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —NR$^2$R$^3$, —S(O)$_n$($C_1$–$C_{10}$ alkyl) wherein n is an integer ranging from 0 to 2, and SO$_2$NR$^2$R$^3$; and
each $R^{16}$ is independently H or —C(O)OR$^5$.

Certain compounds of formula 15 may have asymmetric centers and therefore exist in different enantiomeric forms. This invention relates to the use of all optical isomers and stereoisomers of the compounds of formula 15 and mixtures thereof. In particular, the invention includes both the $R^2$ and S configurations of the methyl group at C-10 of the macrolide ring of formula 15, and both the E and Z isomers of the —OR$^1$ group connected to the nitrogen of the oxime moiety at C-9 of the macrolide ring of formula 15.

The subject invention also includes isotopically-labelled compounds, and the pharmaceutically acceptable salts thereof, which are identical to those recited in Formula 15, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as 2H, 3H, 13C, 14C, 15N, 18O, 17O, 35S, 18F, and 36Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as 3H and 14C are incorporated, are useful in drug and/or substrate tissue distribution assays. Tritiated, i.e., 3H, and carbon-14, i.e., 14C, isotopes are particularly preferred for their ease of preparation and detectability. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of Formula 15 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating bacterial infections through administering prodrugs of compounds of the formula 15. Compounds of formula 15 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 15. The amino acid residues include but are not limited to the naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

Selective introduction of prodrug side chains can be carried out on the hydroxy groups of the hygromycin A core molecule. For instance, exhaustive silylation of the six hydroxy groups of hygromycin A can be carried out, for instance with tert-butyl dimethylsilyl chloride. Subjection of the hexasilyl derivative to the action of potassium carbonate in methanol at room temperature selectively removes the phenolic silyl group, allowing further selective modification at that position. In another example, incomplete silylation of hygromycin A (see PC 10186, R. Linde, 2"-deoxy hygromycin A derivatives, U.S. provisional patent application no. 60/084,058, filed May 4, 1998) provides the pentasilyl derivative in which the C-2" hydroxy group is free. Selective acylation, alkylation, etc. can be carried out on this derivative to provide prodrug attachment at C-2".

DETAILED DESCRIPTION OF THE INVENTION

The process of the present invention and the preparation of the compounds of the present invention are illustrated in the Schemes 1-4 that follow. In the following Schemes and discussion that follows, unless otherwise indicated, $R^1$ to $R^{17}$, $R^{24}$, X, $X^1$, C, D, Y, Z are as defined above. The following Schemes and the discussion that follows describe the preparation of the Compounds of Formulas 1–26.

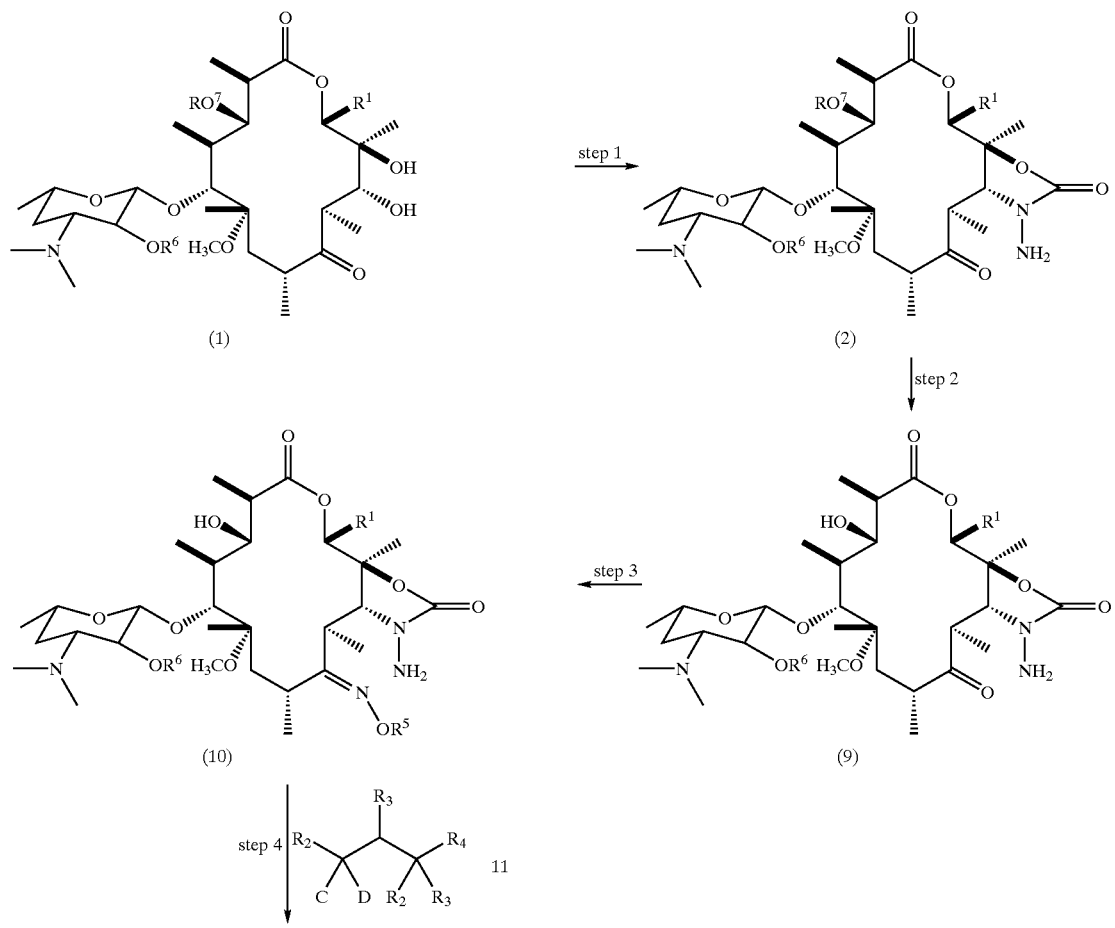

-continued
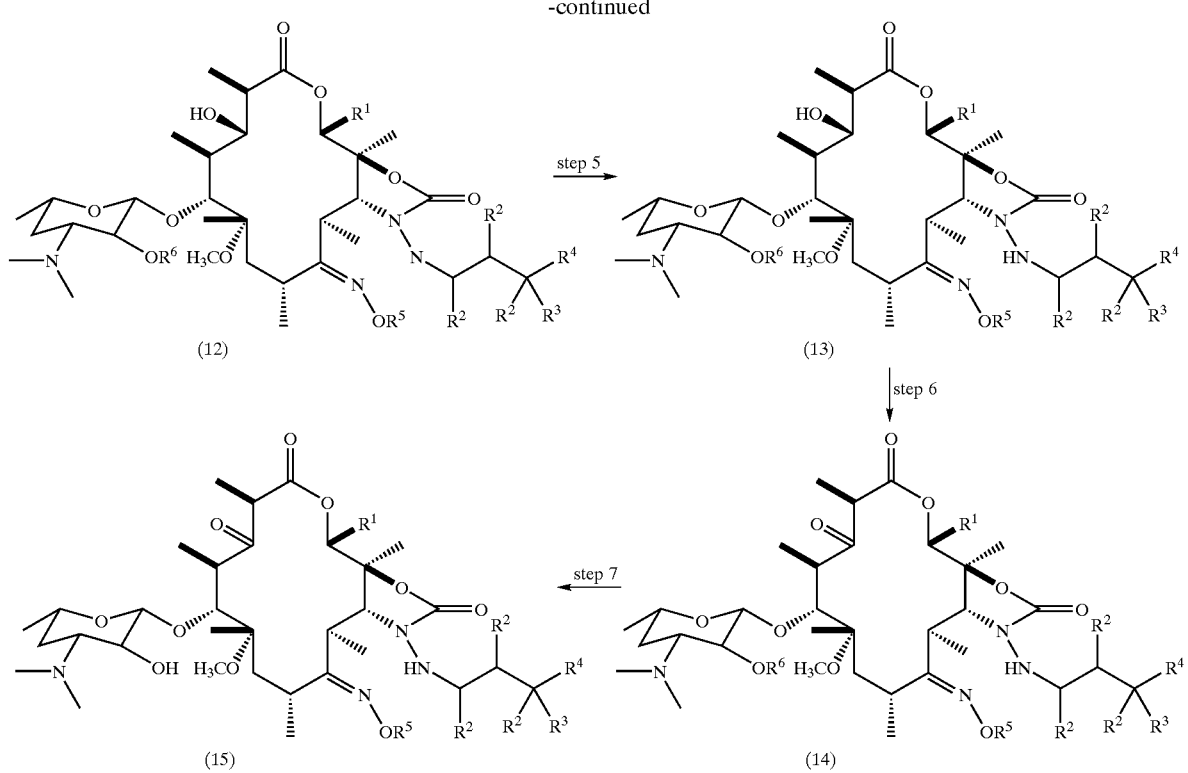

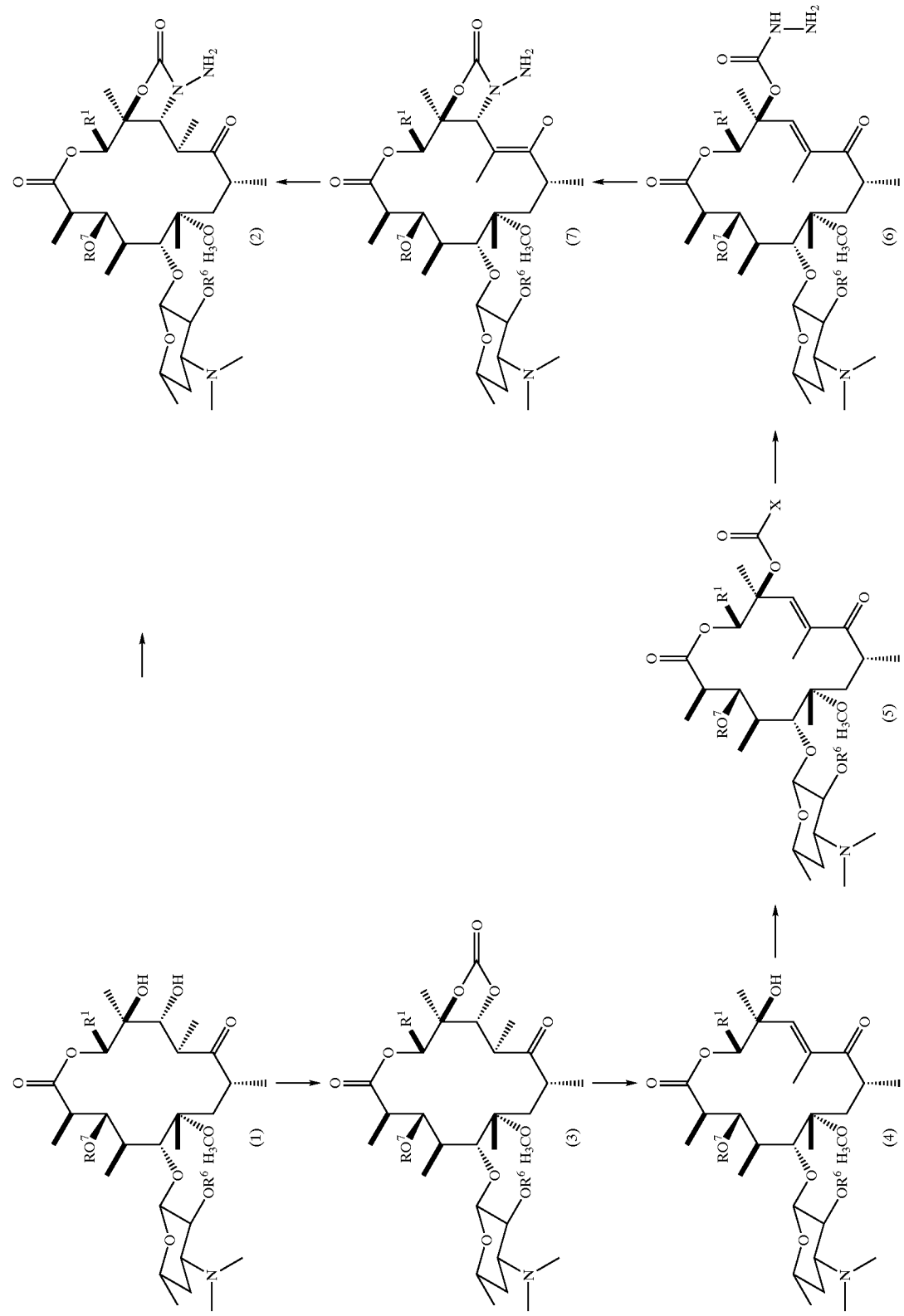

In step 1 of Scheme 1, compound 1 is treated with a carbonyl source including but not limited to carbonyl duimidazole (CDI), phosgene, triphosgene, carbonyl bisbenzotriazole, carbonyl bishydroxybenzotriazole, or carbonyl bis-1,2,4-triazole and a base including but not limited to 1,8-diazabicyclo[5.4.0]undec-7-ene (DBU), 1,2-dimethyl-1,4,5,6-tetrahydro-pyrimidine, sodium hexamethyldisilazane, lithium diisopropylamide, potassium hexamethyldisilazane, or tetramethyl guanidine in a range of inert solvents including, but not limited to, isopropylether, dimethylformamide, N-methylpyrrolidinone, acetonitrile, dimethylacetamide, tetrahydrofuran, dimethylsulfoxide, dioxane, dimethoxyethane, dichioromethane, tetrachloroethane, and dichloroethane. The reaction is monitored for the formation of intermediate of formula 5. Preferably, the reaction is run with CDI and DBU in ether solvent, preferably tetrahydrofuran with or without isopropylether. Once conversion to compound 5 is complete, hydrazine or hydrazine hydrate is added to the reaction between −78° C. and 50° C. Preferably, hydrazine hydrate is added between −10° C. and 10° C. The reaction proceeds through intermediates (3) and (4) and stops at intermediate (5) prior to hydrazine addition (shown in Scheme 2). The second stage of this reaction (after the addition of hydrazine) involves an intermediate of formula (6). No isomerization of the initially formed stereocenter at carbon 10 can take place at the temperature that the hydrazine addition takes place, and so the stereochemistry at $C_{10}$ is a result of the initial quench of the intermediate enol(ate).

In step 2 of Scheme 1, compound 2 can be converted to compound 9 with acids including, but not limited to, hydrochloric, hydrobromic, hydroiodic, sulfuric, nitric, alkylsulfonic acids, tosic acid, triflic acid, or trifluoroacetic acid, with or without water. The reaction can be run in a variety of polar solvents including, but not limited to, water, methanol, ethanol, isopropanol, tertbutanol, dimethylformamide, N-methylpyrrolidinone, acetonitrile, dimethylacetamide, tetrahydrofuran, dimethylsulfoxide, acetic acid, and formic acid over a range of temperatures for −25° C. to 100° C. Preferably, the reaction is run in methanol with 12N hydrochloric acid at 35° C.

In step 3 of Scheme 1, compound 9 can be converted to compound 10 by treating it with a compound of formula $H_2NOR^5$, as its free base or in acid addition salt form such as $R^5ONH_3Cl$. The reaction can be run with or without added base including, but not limited to, pyridine, 2,6-lutidine, imidazole, amine bases, or dimethylaminopyridine. The reaction can be run in a variety of polar solvents including, but not limited to, methanol, ethanol, isopropanol, tertbutanol, dimethylformamide, N-methylpyrrolidinone, acetonitrile, dimethylacetamide, and dimethylsulfoxide at elevated temperature between 40° C. and 150° C. Preferably, the reaction is run with an excess of methoxylaminehydrochloride in isopropanol at 83° C.

In step 4 of Scheme 1, compound 10 can be converted to compound 12 by reacting it with compound 11 in a variety of solvents under neutral or acidic conditions. Some representative acids that can be used as additives, solvent, or co-solvent include, but are not limited to, acetic and formic acid, and usable solvents include, but are not limited to, water, methanol, ethanol, isopropanol, tertbutanol, dimethylformamide, N-methylpyrrolidinone, acetonitrile, dimethylacetamide, tetrahydrofuran, dimethylsulfoxide, dioxane, dimethoxyethane, dichloromethane, tetrachloroethane, dichloroethane, ethylacetate and toluene. Examples of neutral conditions would be heating the reaction in one of the above solvents without acid additive between 50° C. and 150° C. Preferably, the reaction is run in acetic acid or ethanol with acetic acid at room temperature.

In step 5 of Scheme 1, compound 12 can be converted to compound 13 by treating it with a metal hydride reducing agent such as sodium triacetoxyborohydride or sodium cyanoborohydride under acidic conditions. The solvent includes acetic acid, or alcoholic solvent with an acid additive such as acetic acid. The alcoholic solvent includes, but is not limited to, ethanol, methanol, isopropanol, and tert-butanol. Preferably, the reaction is run at room temperature in acetic acid with an excess of sodium triacetoxyborohydride.

In step 6 of Scheme 1, compound 13 can be converted to compound 14 by treating it under Swern conditions. Preferably, the Swern conditions are selected from the following:

(a) In an inert solvent including, but not limited to dichloromethane, dichloroethane, and tetrachloroethane; dimethylsulfoxide is preactivated with activating agents including, but not limited to oxalyl chloride, trifluoroacetic anhydride, sulfuryl chloride, and thionyl chloride; followed by the addition of the compound 13. Trialkylamine base is added after a time period of about 5 minutes to 24 hours at a temperature range from −80° C. to 50° C.;

(b) Compound 13 and dimethylsulfoxide are premixed in one of said inert solvents, followed by addition of said activating agent and then followed by the addition of trialkylamine base at a time period of about 5 minutes to 24 hours. This occurs at a temperature range from about −80° C. to 50° C. Preferably the reaction is run in methylene chloride at 0° C., where the compound of the formula 13 and dimethylsulfoxide are premixed and activated by trifluoroacetic anhydride. This is followed by triethylamine two hours later. The reaction is then warmed to room temperature.

In step 7 of Scheme 1, compound 14 can be converted to compound 15 by treating it with a nucleophile to cleave the $R^6$ protecting group.

In one embodiment the $R^6$ protecting group is removed by solvolysis in an alcoholic or aqueous solvent with the optional addition of base to accelerate the reaction. In the process of preparing compound 15, examples of suitable alcoholic solvents include, but are not limited to, methanol, ethanol, isopropanol and tert-butanol. Examples of bases includes, but are not limited to, sodium carbonate, sodium bicarbonate, potassium carbonate, potassium hydroxide, sodium hydroxide, potassium fluoride and barium hydroxide.

In addition the $R^6$ protecting group can be removed with a nucleophile, including but not limited to, ammonium hydroxide, monoalkyl amine, dialkyl-amine, alkane thiol or hydroxide. Useable solvents include, but are not limited to, water, methanol, ethanol, isopropanol, tertbutanol, dimethylformamide, N-methyl pyrrolidinone, acetonitrile, dimethyl acetamide, tetrahydrofuran, N-methylpyrrolidinone, acetonitrile, dimethylacetamide, tetrahydrofuran ethylacetate, and toluene. Preferably the deprotection is run in methanol with the addition of potassium carbonate at room temperature.

In another embodiment, compound 13, wherein $R^6$ is H, is converted to compound 15 by treating it under Swern conditions. Preferably, the Swern conditions are selected from the following:

(a) In an inert solvent including, but not limited to, dichloromethane, dichloroethane, and tetrachloroethane; dimethylsulfoxide is preactivated with activating agents including, but not limited to, oxalyl chloride, trifluoroacetic anhydride, sulfuryl chloride, and thionyl chloride; followed by addition of the compound 13. Trialkylamine base is added after a time period of about 5 minutes to 24 hours at a temperature range from −80° C. to 50° C.;

(b) Compound 13 and dimethylsulfoxide are premixed in one of the inert solvents, followed by addition of the activating agent and then followed by the addition of trialkylamine base at a time period of about 5 minutes to 24 hours. This occurs at a temperature range from about −80° C. to 50° C. Preferably the reaction is run in methylene chloride at 0° C., where the compound of the formula 13 and dimethylsulfoxide are premixed and activated by trifluoroacetic anhydride. This is followed by triethylamine two hours later. The reaction is then warmed to room temperature.

Alternatively, isolated compound 2 is converted to compound 10 by treating it with a reagent of the formula $H_2NOR^5$ as its acid addition salt, with or without an added base. The base includes, but is not limited to, pyridine, 2,6-lutidine, imidazole, amine bases, or dimethylaminopyridine in polar solvent including, but not limited to, methanol, ethanol, isopropanol, tert-butanol, dimethylformamide, N-methylpyrrolidinone, acetonitrile, dimethylacetamide, and dimethylsulfoxide. The reaction is run at elevated temperatures between about 40° C. and 150° C. Preferably, the reaction is run with an excess of methoxylamine hydrochloride and one equivalent of 2,6-lutidine in tert-butanol at about 80° C.

Alternatively, a compound of formula 13 is produced by reaction of a compound of formula 10 with a compound of formula 11 in a variety of solvents under acidic conditions. Acetic acid is used as an additive, solvent, or co-solvent, and usable solvents include, but are not limited to, methanol, ethanol, isopropanol, tertbutanol, dimethylformamide, N-methylpyrrolidinone, acetonitrile, dimethylacetamide, tetrahydrofuran, dimethylsulfoxide, dioxane, dimethoxyethane, dichloromethane, tetrachloroethane, and dichloroethane. Preferably, the reaction is run in acetic acid or ethanol with acetic acid at room temperature. The reaction is monitored for conversion to an intermediate of formula 12, at which point it is treated with a metal hydride reducing agent such as sodium triacetoxyborohydride or sodium cyanoborohydride. Preferably, the reaction is run at room temperature with an excess of sodium triacetoxyborohydride.

Alternatively, a compound of formula 12 may be prepared by reaction of a compound of formula 20 with a compound of formula

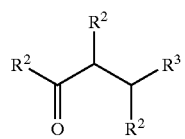

in a variety of alcoholic solvents under acidic conditions. Some representative acids that can be used as additives, or co-solvent are acetic and formic acid, and usable solvents are alcohols including but not limited to, methanol, ethanol, isopropanol, or tert-butanol. The reaction is monitored for the formation of an intermediate of formula 11, at which point a compound of formula 10 is added. Preferably, the reaction is run in ethanol with acetic acid at room temperature.

Alternatively, a compound of formula 13 may be prepared by reaction of a compound of formula 20 as its free base or acid addition salt with a compound of formula

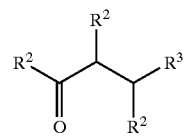

and a compound of formula 10 under acidic conditions. Some representative acids that can be used as additives or co-solvent are acetic and formic acid, and usable solvents include, but are not limited to, acetic acid, formic acid, dichloromethane, dichloroethane, tetrachloroethane, or tetrahydrofuran. This reaction may involve an intermediate of a compound of formula 34. The reaction is monitored for the formation of intermediate 12, at which point it is treated with a metal hydride reducing agent such as sodium triacetoxyborohydride or sodium cyanoborohydride. Preferably, the reaction is run at room temperature in acetic acid with or without dichloromethane as a cosolvent, using an excess of a compound of formula 20 as its bishydrochloric acid salt, and is followed by an excess of sodium triacetoxyborohydride after formation of a compound of formula 12.

Alternatively, a compound of formula 12 may be prepared by reaction of a compound of formula 20 as its free base or acid addition salt with a compound of formula

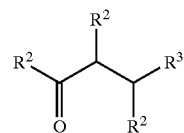

and a compound of formula 10 under acidic conditions. Some representative acids that can be used as additives or co-solvent are acetic and formic acid, and usable solvents include, but are not limited to, acetic acid, formic acid, dichloromethane, dichloroethane, tetrachloroethane, or tetrahydrofuran. This reaction involves an intermediate compound of formula 34. Preferably, the reaction is run at room temperature in acetic acid with or without dichloromethane as a co-solvent, using an excess of a compound of formula 20 as its bishydrochloric acid salt.

Alternatively, a compound of formula 12 is produced by reaction of a compound of formula 20 with a compound of formula

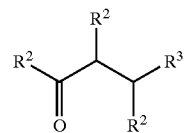

in a variety of alcoholic solvents under acidic conditions. Some representative acids that are used as additives, or co-solvents are acetic and formic acid, and usable solvents are alcohols including but not limited to, methanol, ethanol, isopropanol, or tert-butanol. The reaction is monitored for the formation of an intermediate of formula 11, at which point a compound of formula 10 is added. Preferably, the reaction is run in ethanol with acetic acid at room temperature.

Scheme 3
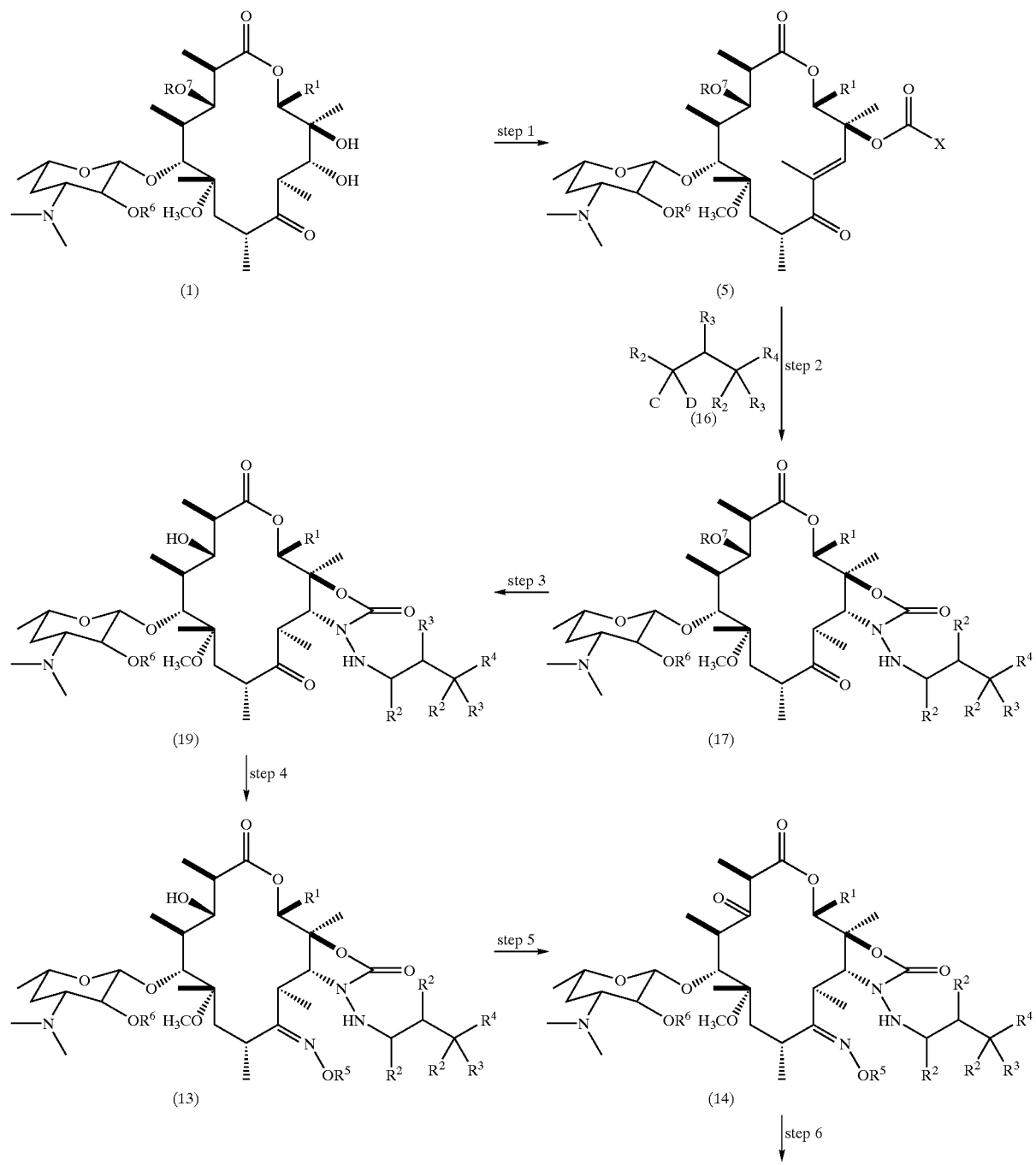

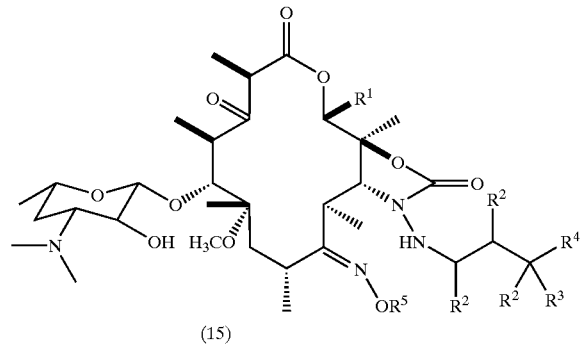
(15)

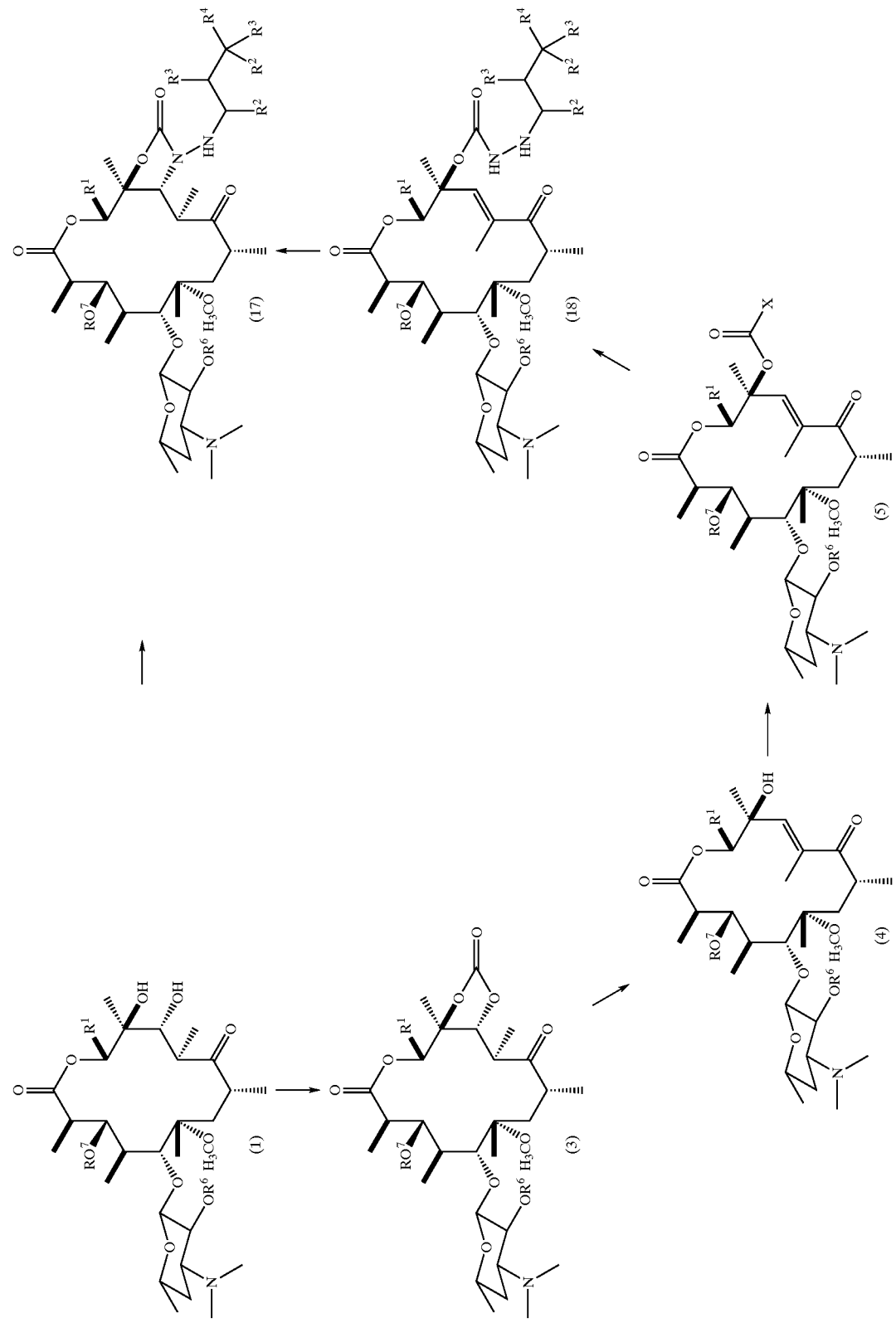

In Scheme 3 step 1, a compound of formula (5) is prepared by the reaction of a compound of formula 2 with a carbonyl source including, but not limited to, carbonyl diimidazole (CDI), phosgene, triphosgene, carbonyl bisbenzotriazole, carbonyl bishydroxybenzotriazole, or carbonyl bis-1,2,4-triazole and base including, but not limited to, 1,8-diazabicyclo[5.4.0]undec-7-ene (DBU), 1,2-dimethyl-1,4,5,6-tetrahydro-pyrimidine, sodium hexamethyldisilazane, lithium diisopropylamide, potassium hexamethyldisilazane, or tetramethyl guanidine in inert solvents including, but not limited to, isopropylether, dimethylformamide, N-methylpyrrolidinone, acetonitrile, dimethylacetamide, tetrahydrofuran, dimethylsulfoxide, dioxane, dimethoxyethane, dichloromethane, tetrachloroethane, and dichloroethane This reaction involves the imtermediates of compounds of the formula (3) and (4). [See scheme 4]

In step 2 of Scheme 3 a compound of formula 17 is prepared by the reaction of a compound of the formula (16) with a compound of formula 5 in a range of inert solvents including, but not, limited to, isopropylether, dimethylformamide, N-methylpyrrolidinone, acetonitrile, dimethylacetamide, tetrahydrofuran, dimethylsulfoxide, dioxane, dimethoxyethane, dichloromethane, tetrachloroethane, and dichloroethane. The reaction is run at a temperature between 0° C. to 150° C. Preferably, the reaction is run in acetonitrile at reflux. This reaction involves an intermediate of a compound of the formula (18). [See scheme 4]

In step 3 of Scheme 3, a compound of formula 19 is prepared by the reaction of a compound of the formula (17) with acids such as hydrochloric, hydrobromic, hydroiodic, sulfuric, nitric, alkylsulfonic acids, tosic acid, triflic acid, or trifluoroacetic acid, with or without water. The reaction is run in a variety of polar solvents including, but not limited to, water, methanol, ethanol, isopropanol, tertbutanol, dimethylformamide, N-methylpyrrolidinone, acetonitrile, dimethylacetamide, tetrahydrofuran, dimethylsulfoxide, acetic acid, and formic acid over a range of temperatures for −25° C. to 100° C. Preferably, the reaction is run in methanol with 12N HCl at 35° C.

In step 4 of Scheme 3, a compound of formula 13 can be prepared by the reaction of a compound of the formula H$_2$NOR$^5$, as its free base or in acid addition salt form such as R$^5$ONH$_3$Cl. The reaction can be run with or without added base including, but not limited to, pyridine, 2,6-lutidine, imidazole, amine bases, or dimethylaminopyridine. The reaction is run in a variety of polar solvents including, but not limited to, methanol, ethanol, isopropanol, tertbutanol, dimethylformamide, N-methylpyrrolidinone, acetonitrile, dimethylacetamide, and dimethylsulfoxide at elevated temperature between 40° C. and 150° C. Preferably, the reaction is run with an excess of methoxylaminehydrochloride in isopropanol at about 83° C.

Alternatively, compound 17 can be converted to compound 13 by treating it with a reagent of the formula H$_2$NOR$^5$ as its acid addition salt, with or without added base. The base includes, but is not limited to, pyridine, 2,6-lutidine, imidazole, amine bases, or dimethylaminopyridine in polar solvent including, but not limited to, methanol, ethanol, isopropanol, tert-butanol, dimethylformamide, N-methylpyrrolidinone, acetonitrile, dimethylacetamide, and dimethylsulfoxide. The reaction is run at elevated temperatures between about 40° C. and 150° C. Preferably, the reaction is run with an excess of methoxylamine hydrochloride and one equivalent of 2,6-lutidine in tert-butanol at about 80° C.

Alternatively, a compound of formula 17 can be prepared by the reaction of compound 1 with a carbonyl source including, but not limited to, carbonyl diimidazole (CDI), phosgene, triphosgene, carbonyl bisbenzotriazole, carbonyl bishydroxybenzotriazole, or carbonyl bis-1,2,4-triazole and a base including, but not limited to, 1,8-diazabicyclo[5.4.0]undec-7-ene (DBU), 1,2-dimethyl-1,4,5,6-tetrahydro-pyrimidine, sodium hexamethyldisilazane, lithium diisopropylamide, potassium hexamethyldisilazane, or tetramethyl guanidine in a range of inert solvents including, but not limited to, isopropylether, dimethylformamide, N-methylpyrrolidinone, acetonitrile, dimethylacetamide, tetrahydrofuran, dimethylsulfoxide, dioxane, dimethoxyethane, dichloromethane, tetrachloroethane, and dichloroethane. The reaction is monitored for the formation of an intermediate of formula 5. Preferably, the reaction is run with CDI and DBU in acetonitrile. Once conversion to formula 5 is complete, a compound of formula 16 is added to the reaction between 0° C. and 150° C. Preferably the addition is done between 25° C. and 75° C.

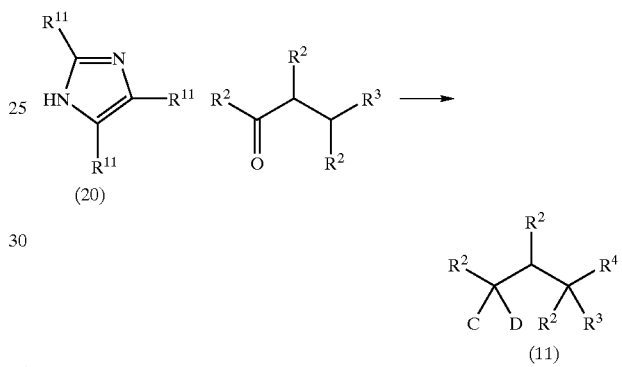

According to the invention, a compound of formula 11 is produced by the reaction of a compound of formula 20 with a compound of formula

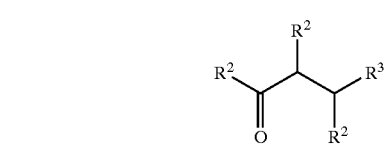

in a variety of alcoholic solvents under acidic conditions. Some representative acids that can be used as additives or co-solvent are acetic and formic acid, and usable solvents such as alcohols including, but not limited to, methanol, ethanol, isopropanol, or tert-butanol. Preferably, the reaction is run in ethanol with acetic acid at room temperature.

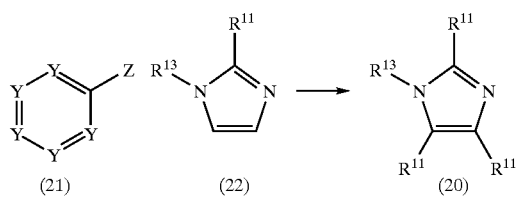

According to the invention, a compound of formula 20 can be prepared by the reaction of a compound of formula 21 with a compound of formula 22. The reaction is run in the presence of a palladium catalyst including, but not limited to, palladium (II) acetate and a trialkyl or triarylphosphine including but not limited to triphenylphosphine, tri-t-butyl-phosphine, or tri-o-tolylphosphine. In the reaction the base includes, but is not limited to, cessium carbonate or potassium carbonate and the solvent includes, but is not limited to, dimethylformamide or N-methylpyrrlidinone at a temperature of about 25° C. to 200° C. Preferably the reaction is run with benzylimidazole and 3-bromopyridine in dimethylformamide at reflux with palladium (II) acetate, triphenyl phosphine and cessium carbonate.

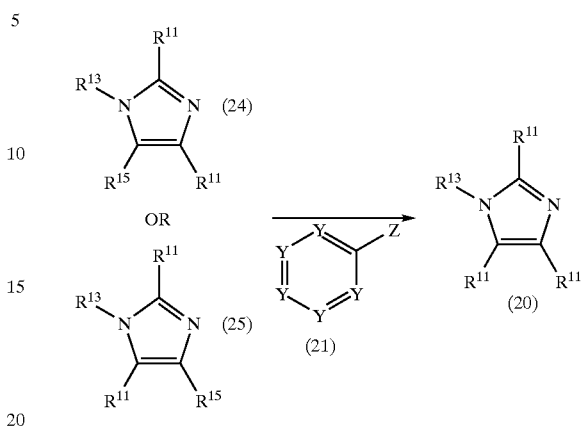

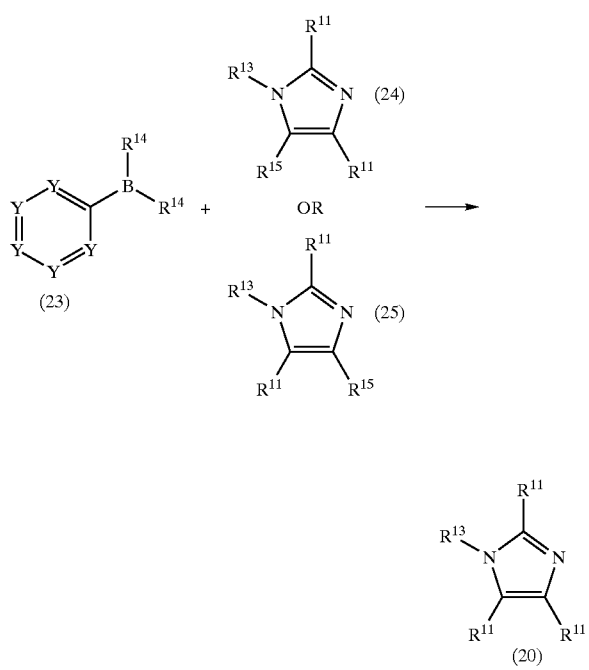

Alternatively, a compound of formula 20 can prepared by the reaction of a compound of formula 23 with a compound of formula 24 or 25. The reaction is run in the presence of an inert solvent, base and a palladium catalyst at a temperature at about 25° C. to 125° C. for about 30 minutes to 48 hours. The base includes, but is not limited to, sodium carbonate, sodium bicarbonate, potassium carbonate, potassium hydroxide, sodium hydroxide, potassium fluoride, and barium hydroxide. Suitable palladium catalysts include, but are not limited to, tetrakis(triphenylphosphine)palladium(0), dichlorobis(triphenylphosphine)palladium(II), palladium(II) acetate, allyllpalladium chloride dimer, and tris(dibenezylideneacetone)dipalladium(0). Optionally the reaction medium could also contain a triarylphosphine or trialkylphosphine, examples of which include, but are not limited to, triphenylphosphine, tri(o-tolyl)phosphine and trit-butylphosphine and could also contain tetrabutylammonium iodide. The inert solvent includes, but is not limited to, tetrahydrofuran, dioxane, and dimethoxyethane. Preferably, the reaction is run in dimethylformamide with potassium hydroxide, tetrakis(triphenylphosphine)palladium(0), and tetrabutylammonium iodide at reflux.

Alternatively, a compound of formula 20 can be prepared by reaction of a compound of formula 24 or 25 with reagents including, but not limited to, a) alkylmagnesium chloride, bromide or iodide, where the alkyl includes but is not limited to methyl, ethyl, isopropyl, or t-butyl, or magnesium(0), followed by treatment with zinc chloride, zinc bromide, or zinc iodide, or, b) with reagents such as alkylzinc chloride, alkyl zinc bromide or alkylzinc iodide, where the alkyl includes but is not limited to, methyl, ethyl, isopropyl, or t-butyl or zinc(0) and zinc chloride, zinc bromide, or zinc iodide followed by reaction with a compound of formula 21 in the presence of a palladium catalyst including , but not limited to, tetrakis(triphenylphosphine)palladium(0), dichlorobis(triphenylphosphine)palladium(II), palladium(II) acetate, allylpalladium chloride dimer, and tris(dibenzylideneacetone)dipalladium(0). The reaction medium may optionally also contain a triarylphosphine or trialkylphosphine, examples of which include but are not limited to triphenyiphosphine, tri(o-tolyl)phosphine and trit-butylphosphine. The inert solvent includes, but is not limited to, tetrahydrofuran, dioxane, and dimethoxyethane. Preferably, the reaction is run in tetrahydrofuran, with ethylmagnesium bromide followed by zinc chloride, followed by the compound of formula 21 and tetrakis(triphenylphosphine)palladium(0), and the reaction is heated from room temperature to 70° C.

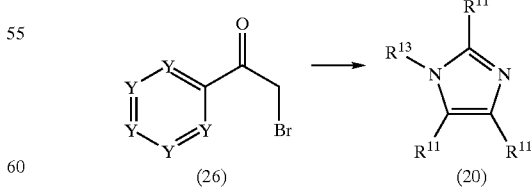

Alternatively, a compound of formula 20 can be prepared by the reaction of a compound of formula 26 as its free base or acid addition salt with formamide at the elevated temperature of about 120° C. to 220° C. Preferably the reaction is run in formamide at 160° C.

Alternatively, a compound of formula 20 can be prepared by the reaction of a compound of formula 26 as its free base or acid addition salt with formamidine acetate in a polar solvent with or without added base at temperatures between 25° C. and 200° C. Examples of polar solvents include, but are not limited to, dimethylformamide, dimethylacetamide, acetonitrile, formamide, and dimethylsulfoxide. Examples of bases include, but are not limited to, potassium acetate and sodium acetate. Preferably, the reaction is run in dimethylformamide with potassium acetate at 65° C.

formula 30 under conditions appropriate to remove the alcohol protecting group $R^{17}$.

a) When $R^{17}$ is trisubstitutedsilyl, disubstitutedketal, or monosubstitutedacetal, the reaction is with acids such as hydrochloric, hydrobromic, hydroiodic, sulfuric, nitric, alkylsulfonic acids, tosic acid, triflic acid, or trifluoroacetic acid; or b) If $R^{17}$ is trisubsubtitutedsilyl, the reaction with flouride sources includes but not limited to, tetrabutylammo-

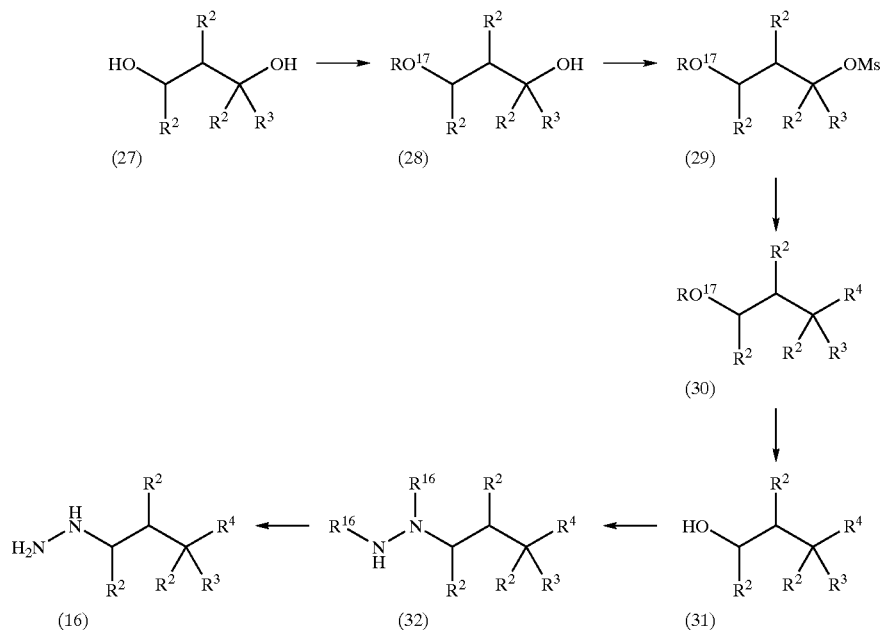

According to the invention, a compound of formula 16 can be prepared by reacting a compound of formula 32 under conditions appropriate to remove the $R^{16}$ protecting group. Where $R^{16}$ is tert-butylcarbamate (BOC), the reaction can be run with acids such as hydrochloric, hydrobromic, hydroiodic, sulfuric, nitric, alkylsulfonic acids, tosic acid, triflic acid, or trifluoroacetic acid, with or without water. The reaction can be run in a variety of polar or nonpolar solvents including, but not limited to water, methanol, ethanol, isopropanol, tertbutanol, dimethylformamide, N-methylpyrrolidinone, acetonitrile, dimethylacetamide, tetrahydrofuran, dimethylsulfoxide, acetic acid, formic acid, toluene, dichloroethane, tetrachloroethane, dioxane, and dichloromethane over a range of temperatures from 25° C. to 200° C. Preferably, the reaction is run in methanol with 6N HCl at 50° C.

According to the invention, a compound of formula 32 is prepared by the reaction of a compound of formula 31 with a trialkyl or triaryl phosphine and a reagent of formula $R^5OC(O)N=NC(O)OR^5$ in an inert solvent. Examples of phosphines include, but are not limited to, triphenylphosphine, trimethylphosphine, tritbutylphosphine, or tributylphosphine. Examples of inert solvents include, but are not limited to, dichloromethane, dichloroethane, tetrachloroethane, dioxane, acetonitrile, or tetrahydrofuran. Preferably, the reaction is run with triphenylphosphine and ditert-butylazadicarboxylate in tetrahydrofuran from 0° C. to room temperature.

According to the invention, a compound of formula 31 can be prepared by the deprotection of a compound of nium flouride, hydroflouric acid, HF-pyridine, potassium flouride, cesium flouride, and sodium flouride, with or without water, in a variety of polar or nonpolar solvents including, but not limited to, water, methanol, ethanol, isopropanol, tert-butanol, dimethylformamide, N-methylpyrrolidinone, acetonitrile, dimethylacetamide, tetrahydrofuran, dimethylsulfoxide, acetic acid, formic acid, toluene, dichloroethane, tetrachloroethane, dioxane, and dichloromethane over a range of temperatures from 25° C. to 200° C. This should suffice to remove $R^7$.Preferably, if $R^7$ is tert-butyidimethylsilyl, the reaction is run in tetrahydrofuran with tetrabutylammonium flouride.

When $R^{17}$ is —C(O)OR$^5$ or $R^6$, the protecting group can be cleaved with a nucleophile. This involves:

a) solvolysis in alcoholic or aqueous solvent, with the addition of base optional to accelerate the reaction. Examples of alcoholic solvents include, but are not limited to, methanol, ethanol, isopropanol, and tertbutanol. Examples of useable bases include, but are not limited to, sodium carbonate, sodium bicarbonate, potassium carbonate, potassium hydroxide, sodium hydroxide, potassium flouride, and barium hydroxide; or b) with a nucleophile including, but not limited to, ammonium hydroxide, monoalky amine, dialkylamine, alkanethiol, or hydroxide in a solvent including but not limited to, water, methanol, ethanol, isopropanol, tertbutanol, dimethylformamide, N-methylpyrrolidinone, acetonitrile, dimethylacetamide, tetrahydrofuran, dimethylsulfoxide, dioxane, dimethoxyethane, dichloromethane, tetrachloroethane, dichloroethane, ethylacetate and toluene.

Preferably, this deprotection is run in methanol with the addition of potassium carbonate at room temperature.

According to the invention, a compound of formula 30 can be prepared by the reaction of a compound of formula 29 with a compound of formula 20 and base in a polar solvent. Examples of bases that that can be used include, but are not limited to, sodium hydride, potassium tert-butoxide, sodium tert-butoxide, potassium hexamethyldisilazide, sodium hexamethyldisilazide, and lithium diisopropylamide. Examples of solvents that can be used include, but are not limited to, dimethylformamide, N-methylpyrrolidinone, acetonitrile, dimethylacetamide, tetrahydrofuran, and dimethylsulfoxide. Preferably, the reaction is run with sodium hydride in dimethylformamide.

According to the invention, a compound of formula 29 can be prepared by the reaction of a compound of formula 28 with a mesylating agent and a base in inert solvent. Mesylating agents include, but are not limited to, mesic anyhydride, mesyl chloride, and mesyl bromide. Useable bases include, but are not limited to, trialkylamines such as triethylamine or diisopropylethylamine, pyridine, lutidine, and dimethylaminopyridine. Examples of inert solvents include, but are not limited to, tetrahydrofuran, dichloroethane, tetrachloroethane, dioxane, and dichloromethane. Preferably, the reaction is run with mesyl chloride and triethylamine in dichloromethane.

According to the invention, a compound of formula 28 can be prepared by the selective protection of a compound of formula 27 with reagents including, but not limited to, trisubstitutedsilyl chloride, trisubsubtitutedsilyl imidazole, trisubsubtitutedsilyl triflate, acid chlorides, acid anhydrides, chloroformates, carbonate anhydrides, mixed anhydrides, and isocyanates and a base including but not limited to, imidazole, trialkylamines, triethylamine or diisopropylethylamine, pyridine, lutidine, and dimethylaminopyridine in aprotic solvents including, but not limited to, dimethylformamide, N-methylpyrrolidinone, acetonitrile, dimethylacetamide, tetrahydrofuran, dimethylsulfoxide, toluene, dichloroethane, tetrachloroethane, dioxane, and dichloromethane. Preferably, the reaction is run with tert-butdidimethylsilyl chloride and imidazole in dichloromethane at 0° C.

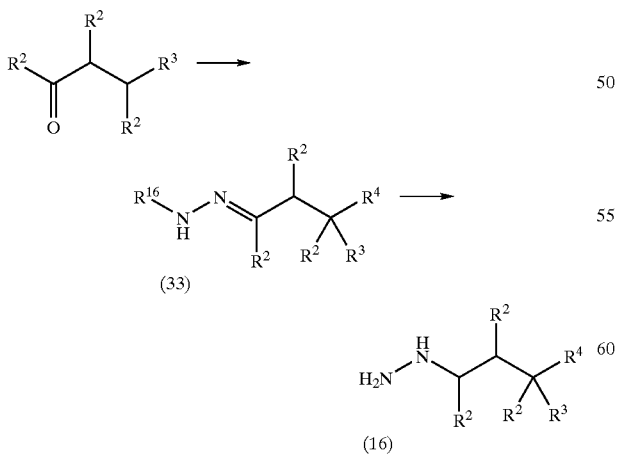

In another embodiment, a compound of formula 16 can be prepared by the reduction of a compound of formula 33 with a metal hydride reducing agent such as sodium triacetoxyborohydride or sodium cyanoborohydride under acidic conditions. The solvent includes, but is not limited to, acetic acid, acetonitrile, or alcoholic solvent with an acid additive such as acetic acid. The alcoholic solvent includes, but is not limited to, ethanol, methanol, isopropanol, and tert-butanol. Preferably, the reaction is run at room temperature in acetic acid with an excess of sodium triacetoxyborohydride.

According to the invention, a compound of formula (33) can be prepared by the reaction of a compound of formula

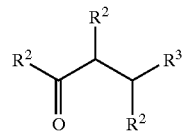

with a reagent of formula $R^{16}NHNH_2$ under neutral or acidic conditions. Some representative acids that can be used as additives, solvent, or co-solvent are acetic and formic acid, and usable solvents include, but are not limited to, water, methanol, ethanol, isopropanol, tertbutanol, dimethylformamide, N-methylpyrrolidinone, acetonitrile, dimethylacetamide, tetrahydrofuran, dimethylsulfoxide, dioxane, dimethoxyethane, dichloromethane, tetrachloroethane, dichloroethane, ethylacetate and touene. Examples of neutral conditions would be heating the reaction in solvent without acid additive between 80° C. and 110° C. Preferably, the reaction is run in acetic acid or ethanol with acetic acid at room temperature.

In another embodiment, a compound of formula 16 includes prepared by the reaction of a compound of formula

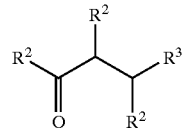

with reagent of formula $R^{16}NHNH_2$ in a variety of solvents under acidic conditions, followed by reduction with a metal hydride reducing agent such as sodium triacetoxyborohydride or sodium cyanoborohydride under acidic conditions. Some representative acids that can be used as additives, solvent, or co-solvent include but are not limited to, acetic and formic acid, and usable solvents include, but are not limited to acetonitrile, dichloromethane, tetrachloroethane, and dichloroethane. Preferably, the reaction is run in acetic acid at room temperature, followed by reduction with sodium triacetoxyborohydride.

The present invention is illustrated by the following examples, but it is not limited to the details thereof.

EXAMPLE 1

2',4"-Bis-O-acetyl-11-deoxy-11-hydrazo-6-O-methylerythromycin A,11,12-carbamate (2)

To a dried 200L vessel under nitrogen atmosphere was charged 26 gallons IPE and 11 gallons THF. 11.92 kg of 2',4"-bis-O-acetyl-6-O -methylerythromycin A (1) (14.33 mol) was added followed by 11.62 kg CDl (71.65 mol) and 6.54 kg DBU (43 mol). The white slurry was heated to 45–50° C. for 2.5 hours. The reaction was assayed for complete conversion to 10,11-anhydro-2',4"-bis—O-acetyl-12O-imidazoylcarbonyl-6O-methylerythromycin A (5). Upon completion, the reaction was cooled to 0° C. and 5.6 L hydrazine hydrate (114.64 mol) was slowly added. The reaction was stirred for 1 h and assayed for completeness. The IPE and THF was removed in vacuo and 23L of water was added. The solids were granulated for 2.5 hours at 15° C., then filtered and rinsed with 10L water. The solids were air dried at 55° C. A total of 10.8 kg of 2',4"-Bis-O-acetyl-11-deoxy-11-hydrazo-6-O-methylerythromycin A,11,12-carbamate (2) was obtained (12.4 mol, 83%).

EXAMPLE 2

2',4"-Bis-O-acetyl-11-deoxy-11-hydrazo-5-O-desosaminyl-6-O-methylerythronolide A,11,12-carbamate (9)

To a 200L reactor was charged 24L methanol and 0.94L 12N HCl (10.6 mol). The solution was set at 30° C. and 4.7 kg 2',4"-Bis-O-acetyl-11-deoxy-11-hydrazo-6-O-methylerythromycin A, 11,12-carbamate (2) (5.3 mol) was added. The reaction was stirred 10 min to dissolve the solids, then it was heated to 45° C. for 5 hr. Once the reaction was complete, the methanol was removed in vacuo, and the internal temperature was set at 20° C. The reaction was extracted between sodium carbonate (1.7 kg, 16 mol) in 24L water and 47L EtOAc. The aqueous layer was separated, and the organic layer was concentrated to low volume. 3.5L IPE was added and the solids were granulated at 20° C. for 12 h. The solids were filtered, rinsed with 3L IPE, and dried in vacuo to yield 2.55 kg (3.80 mol, 67%) 2',4"-Bis-O-acetyl-11-deoxy-11-hydrazo-5-O-desosaminyl-6-O-methylerythronolide A, 11,12-carbamate (9).

EXAMPLE 3

2',4"-Bis-O-acetyl-9-deoxo-9-methoxyimino-11-deoxy-11-hydrazo-5-O-desosaminyl-6-O-methylerythronolide A, 11,12-carbamate (10)

To a dried reactor under nitrogen atmosphere was charged 32L of isopropanol (IPO), 6.83 kg 2',4"-Bis-O-acetyl-11-deoxy-11-hydrazo-5-O-desosaminyl-6-O-methylerythronolide A, 11,12-carbamate (9) (10.2 mol), and 13.6 kg MeONH$_3$Cl (162.6 mol) at room temperature. The reaction was heated to 83° C. for 32 hours. Once the reaction was complete (by HPLC assay), the reaction was cooled to 25° C. and 65L EtOAc was charged. A solution of 17 kg Na$_2$CO$_3$ (162.6 mol) in 54L water was slowly added. The pH of the aqueous layer was >9 after the addition was complete. The layers were allowed to settle for 30 min, then separated. The jacket temperature was set to 45° C. and the organics were removed in vacuo to the lowest stirrable volume. The jacket was cooled to 15° C., and 30L of EtOAc was added to the slurry. The solids were granulated for 2.5 h, then filtered, rinsed with 6L EtOAc, and dried in vacuo to yield 4.55 kg 2',4"-Bis-O-acetyl-9-deoxo-9-methoxyimino-11-deoxy-11-hydrazo-5-O-desosaminyl-6-O-methylerythronolide A, 11,12-carbamate (10) (6.49 mol, 64%).

EXAMPLE 4

2',4"-Bis-0-acetyl-9-deoxo-9-methoxyimino-11-deoxy-11-hydrazo-5-0-desosaminyl-6-O-methylerythronolide A, 11, 12-carbamate (10)

2',4"-Bis-0-acetyl-11-deoxy-11-hydrazo-6-O-methylerythromycin A, 11,12-carbamate (2) (0.936 g, 1.07 mmol) was suspended in 10 mL IPO and 0.45 g MeONH$_3$Cl (5.4 mmol) was added. The reaction was heated at 80° C. for 18 h. The reaction was cooled to 25° C., and 0.27 g MeONH$_3$Cl (3.2 mmol) was added. The reaction was heated at 90° C. for 18 h. EtOAc was added, and the mixture was extracted with water twice and brine once. The organics were dried over Na$_2$SO$_4$ and concentrated to give 1.01 g 2',4"-Bis-0-acetyl-9-deoxo-9-methoxyimino-11-deoxy-11-hydrazo-5-0-desosaminyl-6-O-methylerythronolide A, 11,12 -carbamate (10). The product could be purified by crystallization from EtOAc.

EXAMPLE 5 a(3aS,4R,7R,8S,9S,10R,11R,13R,15R,15aR)-10-[[2-O-Acetyl-3,4,6-trideoxy-3(dimethylamino)-β-D-xylo-hexopyranosyl]oxy]-2H-Oxacyclotetradecino [4,3-d]oxazole-2, 6,14(1H,7H)-trione 4-ethyldecahydro-8-hydroxy-11-methoxy-3a,7,9,11,13, 15-hexamethyl-1 [[(3R)-3-[4-(3-pyridinyl)-1H-imidazol-1-yl]butylidine]amino]-14-O-methyloxime (12)

(R/S)-3-(4-pyridin-3-yl-imidazol-1-yl)-butan-1-al (11) (8.19, 24.2 mmol) was dissolved in 120 mL HOAc and 2',4"-Bis-O-acetyl-9-deoxo-9-methoxyimino-11-deoxy-11-hydrazo-5-O-desosaminyl-6-O-methylerythronolide A, 11,12-carbamate (10) (11.3 g, 16.1 mmol) was added. All solids dissolved after 15 min. After 1 h, the reaction was poured into 250 g sodium carbonate in 1.25L water and 400 mL EtOAc. The water layer was removed, the organics were washed with brine, and dried over sodium sulfate. The solvent was removed in vacuo to leave 15.1 g of (12).

EXAMPLE 6

(3aS,4R,7R,8S,9S,10R,11R,13R,15R,15aR)-10-[[2-O-Acetyl (dimethylamino)-β-D-xylo-hexopyranosyl]oxal-2H-Oxacyclotetradecino[4,3-d] oxazole-2,6,14(1H,7H)-trione 4-ethyldecahydro-8-hydroxy-11-methoxy-3a,7,9,11,13,15-hexamethyl-1 [[(3R)-3-[4-(3-pyridinyl)-1H-imidazol-1-yl] butylidine]amino]-14-O-methyloxime (12)

To a stirred solution of crotonaldehyde (2 mmol) in ethanol is added (6 mmol) acetic acid and (6 mmol) 3-(1 (3)H-imidazole-4-yl)-pyridine. The reaction is stirred for 48 hours, and is assayed for the formation of (R/S)-3-(4-pyridin-3-yl-imidazol-1-yl)-butan-1-al (11). After complete formation of (11), a compound of formula 10 is added and the reaction is stirred for 1 hour. The reaction is poured into sodium carbonate, and extracted with ethyl acetate. The organic layer is dried over sodium sulfate and concentrated in-vacuo to yield (12).

EXAMPLE 7

(3aS,4R,7R,8S,9S,10R,11R,13R,15R,15aR)-10-[[2-O-Acetyl-3,4,6-trideoxy-3-(dimethylamino)-62 -D-xylo-hexopyranosyl]oxy]-2H-Oxacyclotetradecino [4,3-d]oxazole-2,6,14(1H,7H)-trione 4-ethyldecahydro-8-hydroxy-11-methoxy-3a,7,9,11,13, 15-hexamethyl-1-[[(3R)-3-[4-(3-pyridinyl)-1H-imidazol-1-yl]butyl]amino]-14-O-methyloxime (13)

To 13.5 g (3aS,4R,7R,8S,9S,10R,11R,13R,15R,15aR)-10-[[2-O-Acetyl-3,4,6-tridoxy-3-3-(dimethylamino)-β-D-xylo-hexopyranosyl]oxy]-2H-Oxacyclotetradecino[4,3-d] oxazole-2,6,14(1H,7H)-trione 4-ethyldecahydro-8-hydroxy- 11-methoxy-3a,7,9,11,13,15-hexamethyl-1-[[(3R)-3-[4-(3-pyridinyl)-1H-imidazol-1-yl]butylidine]amino]-14-O-methyloxime in 60 mL HOAc was added NaHB(OAc)$_3$ (11.1 g, 52.5 mmol) at 25° C. After 2 h, the reaction was poured into 130 g sodium carbonate in 700 mL water and 400 mL EtOAc. The water layer was removed, the organics were washed with brine, and dried over sodium sulfate. The solvent was removed in vacuo to leave 13.3 g of (13).

EXAMPLE 8

(3aS,4R,7R,8S,9S,10R,11R,13R,15R,15aR)-10-[[2-O-Acetyl-3,4,6-trideoxy-3-(dimethylamino)-β-D-xylo-hexopyranosyl]oxy]-2H-Oxacyclotetradecino[4,3-d]oxazole-2,6,14(1H,7H)-trione 4-ethyldecahydro-8-hydroxy-11-methoxy-3a,7,9,11,13,15-hexamethyl-1-[[(3R)-3-[4-(3-pyridinyl)-1H-imidazol-1-yl]butyl]amino]-14-O-methyloxime (13)

(R/S)-3-(4-pyridin-3-yl-imidazol-1-yl)-butan-1-al (1.5 mmol) is dissolved in 15 mL HOAc and 2',4"-Bis-O-acetyl-9-deoxo-9-methoxyimino-11-deoxy-11-hydrazo-5-O-desosaminyl-6-O-methylerythronolide A, 11,12-carbamate (10) (1 mmol) is added. After 1 h, NaHB(OAc)$_3$ (10 mmol) is added at 25° C. After 2 h, the reaction is poured into sodium carbonate in water and EtOAc. The water layer is removed, the organics are washed with brine, and dried over sodium sulfate. The solvent is removed in vacuo to leave (13).

EXAMPLE 9

(3aS,4R,7R,9S,10R,11R,13R,15R,15aR)-10-[[2-O-Acetyl-3,4,6-trideoxy-3-(dimethylamino)-D-xylo-hexopyranosyl]oxy]-2H-Oxacyclotetradecino[4,3-d]oxazole-2,6,8,14(1H,7H,9H)-tetraone 4-ethyldecahydro-11-methoxy-3a,7,9,11,13,15-hexamethyl-1-[[(3R)-3-[4-(3-pyridinyl)-1H-imidazol-1-yl]butyl]amino]-14-O-methyloxime (14)

To (3aS,4R,7R,8S,9S,10R,11R,13R,15R,15aR)-10-[[2-O-Acetyl-3,4,6-trideoxy-3-(dimethylamino)-β-D-xylo-hexopyranosyl]oxy]-2H-Oxacyclotetradecino[4,3-d]oxazole-2,6,14(1H,7H)-trione 4-ethyldecahydro-8-hydroxy-[]11-methoxy-3a,7,9,11,13,15-hexamethyl-1-[[(3R)-3-[4-(3-pyridinyl)-1H-imidazol-1-yl]butyl]amino]-14-O-methyloxime (13) (3.65 g, 4.06 mmol) in 40 mL methylene chloride and 8 mL DMSO at −7° C. was added TFAA (1.13 mL, 8.11 mmol). The reaction was stirred for 45 min and triethylamine (2.3 mL, 16.2 mmol) was added. 3The reaction was warmed to 25° C. and stirred 1 h. 200 mL EtOAc was added and the solution was washed with brine three times, satd. sodium carbonate once, and brine once, then dried over sodium sulfate. The organics were concenrated in vacuo to provide 3.71 g of (14).

EXAMPLE 10

(3aS,4R,7R,9S,10R,11R,13R,15R,15aR)-10-[[3,4,6-trideoxy-3-(dimethylamino)-β-D-xylo-hexopyranosyl]oxy]-2H-Oxacyclotetradecino[4,3-d]oxazole-2,6,8,14(1H,7H,9H)-tetraone 4-ethyldecahydro-11-methoxy-3a,7,9,11,13,15-hexamethyl-1-[[(3R)-3-[4-(3-pyridinyl)-1H-imidazol-1-yl]butyl]amino]-14-O-methyloxime (15)

1.0 g (3aS,4R,7R,9S,10R,11R,13R,15R,15aR)-10-[[2-O-Acetyl-3,4,6-trideoxy-3-(dimethylamino)-β-D-xylo-hexopyranosyl]oxy]-2H-Oxacyclotetradecino[4,3-d]oxazole-2,6,8,14(1H,7H,9H)-tetraone 4-ethyldecahydro-11-methoxy-3a,7,9,11,13,15-hexamethyl-1-[[(3R)-3-[4-(3-pyridinyl)-1H-imidazol-1-yl]butyl]amino]-14-O-methyloxime (14-O-methyloxime (14) was dissolved in 8 mL methanol and catalytic potassium carbonate was added. The reaction was stirred for 18 h, then concentrated to provide 0.97 g material.

EXAMPLE 11

(3aS,4R,7R,9S,10R,11R,13R,15R,15aR)-10-[[3,4,6-trideoxy-3-(dimethylamino)-β-D-xylo-hexopyranosyl]oxy]-2H-Oxacyclotetradecino[4,3-d]oxazole-2,6,8,14(1H,7H,9H)-tetraone 4-ethyldecahydro-11-methoxy-3a,7,9,11,13,15-hexamethyl-1-[[(3R)-3-[4-(3-pyridinyl)-1H-imidazol-1-yl]butyl]amino]-14-O-methyloxime (15)

To (3aS,4R,7R,8S,9S,10R,11R,13R,15R,15aR)-10-[[2-O-Acetyl-3,4,6-trideoxy-3-(dimethylamino)-β-D-xylo-hexopyranosyl]oxy]-2H-Oxacyclotetradecino[4,3-d]oxazole-2,6,14(1H,7H)-trione 4-ethyldecahydro-8-hydroxy-11-methoxy-3a,7,9,11,13,15-hexamethyl-1-[[(3R)-3-[4-(3-pyridinyl)-1H-imidazol-1-yl]butyl]amino]-14-O-methyloxime (13) (1 mmol) in methylene chloride and DMSO at −7° C. will be added TFAA (4 mmol). The reaction will be stirred for 45 min and triethylamine (8 mmol) will be added. The reaction will be warmed to 25° C. and stirred 1 h. EtOAc will be added and the solution will be washed with brine three times, satd. sodium carbonate once, and brine once, then dried over sodium sulfate. The organics will be concenrated in vacuo to provide (15).

EXAMPLE 12

(3aS,4R,7R,8S,9S,10R,11R,13R,15R,15aR)-10-[[2-O-Acetyl-3,4,6-teideoxy-3-(dimethylamino)-β-D-xylo-hexopyranosyl]oxy]-2H-Oxacyclotetradecino[4,3-d]oxazole-2,6,14(1H,7H)-trione 4-ethyldecahydro-8-hydroxy-11-methoxy-3a,7,9,11,13,15-hexamethyl-1-[[(3R)-3-[4-(3-pyridinyl)-1H-imidazol-1-yl]butyl]amino]-14-O-methyloxime (13)

To 0.555 g (3aS,4R,7R,8S,9S,10R,11R,13R,15R,15aR)-10-[[3,4,6-trideoxy-3-(dimethylamino)-β-D-xylo-hexopyranosyl]oxy]-2H-Oxacyclotetradecino[4,3-d]oxazole-2,6,14(1H,7H)-trione 4-ethyldecahydro-8-hydroxy-11-methoxy-3a,7,9,11,13,15-hexamethyl-1-[[(3R)-3-[4-(3-pyridinyl)-1H-imidazol-1-yl]butyl]amino]-14-O-methyloxime (13) (0.62 mmol) in 4 mL methylene chloride was added 0.2 mL Ac$_2$O (2.1 mmol). After 10 min, the reaction was poured into satd. sodium carbonate and extracted twice with methylene chloride. The organics were dried over sodium sulfate and concentrated in vacuo to provide 0.51 g of material.

EXAMPLE 13

10,11-anhydro-2',4"-bis-O-acetyl-12-O-imidazoylcarbonyl-6-O-methylerythromycin A To a dried vessel under nitrogen atmosphere is charged THF. 2',4"-bis-O-acetyl-6-O-methylerythromycin A (1) (1 mol) is added followed by CDI (5 mol) and DBU (3 mol). The reaction is heated to 45–50° C. for 2.5 hours. The reaction is assayed for complete conversion to 10,11-anhydro-2',4"-bis-O-acetyl-12-O-imidazoylcarbonyl-6-O-methylerythromycin A (5). Upon completion, the reaction is cooled to 25° C. and water is added. The aqueous layer is separated, and the organic solvents is removed in vacuo. The products 5 is then isolated.

EXAMPLE 14

(3aS,4R,7R,8S,9S,10R,11R,13R,15R,15aR)-8-[[4-O-Acetyl-2,6-dideoxy-3-C-methyl-3-O-methyl-α-L-ribo-hexopyranosyl]oxy]-4-ethyldecahydro-11-methoxy-3a,7,9,11,13,15-hexamethyl-1-[[(3R)-3-[4-(3-pyridinyl)-1H-imidazol-1-yl]butyl]amino]-10-[[2-O-acetyl-3,4,6-trideoLxy-3-(dimethylamino)-β-D-xylo-hexopyranosyl]oxy]-2H-Oxacyclotetradecino[4,3-d]oxazole-2,6,14(1H,7H)-trione (17)

To a solution of 10,11-anhydro-2',4"-bis-O-acetyl-12-O-imidazoylcarbonyl-6-O-methylerythromycin A (5) in THF is added 1.0 equivalents of 3-[1-[(1R)-3-hydrazino-1-methylpropyl]-1H-imidazol-4-ylpyridine (16) in THF. The reaction is stirred at room temperature and assayed for completeness. If the reaction is producing 18 and not 17, a base such as KOtBu is added. Upon completion, the reaction is quenched with water, EtOAc is added, and the water layer is separated. The EtOAc and THF is removed in vacuo and the product (17) is isolated.

EXAMPLE 15

(3aS,4R,7R,8S,9S,10R,11R,13R,15R,15aR)-8-[[4-O-Acetyl-2,6-dideoxy-3-C-methyl-3-O-methyl-α-L-ribo-hexopyranosyl]oxy]-4-ethyldecahydro-11-methoxy-3a,7,9,11,13,15-hexamethyl-1-[[(3R)-3-[4-(3-pyridinyl)-1H-imidazol-1-yl]butyl]amino]-10-[[-O-acetyl-3,4,6-trideoxy-3-(dimethylamino)-β-D-xylo-hexopyranosyl]oxy]-2H-Oxapyclotetradecino]4,3-d]oxazole-2,6,14(1H,7H)-trione (17)

To a dried vessel under nitrogen atmosphere is charged THF. 2',4"-Bis-O-acetyl-6-O-methylerythromycin A (1) (1 mol) is added followed by CDI (5 mol) and DBU (3 mol). The reaction is heated to 45–50° C. for 2.5 hours. The reaction is assayed for complete conversion to acylimidazole 5. Upon completion, the reaction is cooled to 25° C. and water is added. After the reaction is finished, 3-[1-[(1R)-3-hydrazino-1-methylpropyl]-1H-imidazol-4-ylpyridine (16) (1 mol) is added. The reaction is stirred and assayed for completeness. EtOAc and water is added, and the layers separated and the water layer removed. The EtOAc and THF is removed in vacuo and the product (17) is isolated.

EXAMPLE 16

(3aS,4R,7R,8S,9S,10R,11R,13R,15R,15aR)-10-[[2-O-Acetyl-3,4,6-trideoxy-3-(dimethylamino)-β-D-xylo-hexopyranosyl]oxy]-4-ethyldecahydro-8-hydroxy-11-methoxy-3a,7,9,11,13,15-hexamethyl-1-[[(3R)-3-[4-(3-pyridinyl)-1H-imidazol-1-yl]butyl]amino]-2H-Oxacyclotetradecino[4,3-d]oxazole-2,6,14(1H,7H)-trione (19)

To a reactor is charged methanol and 12N HCl (5 mol). The temperature is set at 30° C. and (3aS,4R,7R,8S,9S,10R,11R,13R,15R,15aR)-8-[[4-O-Acetyl-2,6-dideoxy-3-C-methyl-3-O-methyl-α-L-ribo-hexopyranosyl]oxy]-4-ethyldecahydro-11-methoxy-3a,7,9,11,13,15-hexamethyl-1-[[(3R)-3-[4-(3-pyridinyl)-1H-imidazol-1-yl]butyl]amino]-10-[[2-O-acetyl-3,4,6-trideoxy-3-(dimethylamino)-β-D-xylo-hexopyranosyl]oxy]-2H-Oxacyclotetradecino[4,3-d]oxazole-2,6,14(1H,7H)-trione (17) (1 mol) is added. The reaction is stirred to dissolve the solids, then it is heated to 45° C. until complete. Once the reaction is complete, the methanol is removed in vacuo, and the internal temperature is set at 20° C. The reaction is extracted between sodium carbonate (6 mol) in water and EtOAc. The aqueous layer is separated, and the organic layer is concentrated to low volume. The product (19) is then isolated.

EXAMPLE 17

(3aS,4R,7R,8S,9S,10R,11R,13R,15R,15aR)-10-[[2-O-Acetyl-3,4,6-trideoxy-3-(dimethylamino)-β-D-xylo-hexopyranosyl]oxyl-2H-Oxacyclotetradecino[4,3-d]oxazole-2,6,14(1H,7H)-trione 4-ethyldecahydro-8-hydroxy-11-methoxy-3a,7,9,11,13,15-hexamethyl-1-[[(3R)-3-[4-(3-pyridinyl)-1H-imidazol-1-yl]butyl]amino]-14-O-methyloxime (13)

To a dried reactor under nitrogen atmosphere is charged isopropanol, (3aS,4R,7R,8S,9S,10R,11R,13R,15R,15aR)-10-[[2-O-Acetyl-3,4,6-tridoxy-3-(dimethylamino)-β-D-xylo-hexopyranosyl]oxy]-4-ethyldecahydro-8-hydroxy-11-methoxy-3a,7,9,11,13,15-hexamethyl-1-[[(3R)-3-[4-(3-pyridinyl)-1H-imidazol-1-yl]butyl]amino]-2H-Oxacyclotetradecino[4,3-d]oxazole-2,6,14(1H,7H)-trione (19) (1 mol), and MeONH$_3$Cl (10 mol) at room temperature. The reaction is heated to 83° C. until the reaction is complete. The reaction is cooled to 25° C. and EtOAc is charged. A solution of Na$_2$CO$_3$ (10 mol) in water is slowly added. The pH of the aqueous layer is >9 after the addition is complete. The layers are allowed to settle for 30 min, then separated. The organics is removed in vacuo and the product (13) is isolated.

EXAMPLE 18

(3aS,4R,7R,8S,9S,10R,11R,13R,15R,15aR)-10-[[2-O-Acetyl-3,4,6-trideoxy-3-(dimethylamino)-β-D-xylo-hexopyranosyl]oxy]-2H-Oxacyclotetradecino[4,3-d]oxazole-2,6,14(1H,7H)-trione 4-ethyldecahydro-8-hydroxy-11-methoxy-3a,7,9,11,13,15-hexamethyl-1-[[(3R)-3-[4-(3-pyridinyl)-1H-imidazol-1-yl]butyl]amino]-14-O-methyloxime (13)

To a dried reactor under nitrogen atmosphere is charged isopropanol, (3aS,4R,7R,8S,9S,10R,11R,13R,15R,15aR)-8-[[4-O-Acetyl-2,6-dideoxy-3-C-methyl-3-O-methyl-α-L-ribo-hexopyranosyl]oxy]-4-ethyldecahydro-11-methoxy-3a,7,9,11,13,15-hexamethyl-1-[[(3R)-3-[4-(3-pyridinyl)-1H-imidazol-1-yl]butyl]amino]-10-[[2-O-acetyl-3,4,6-trideoxy-3-(dimethylamino)-β-D-xylo-hexopyranosyl]oxy]-2H-Oxacyclotetradecino[4,3-d]oxazole-2,6,14(1H,7H)-trione (17) (1 mol), and MeONH$_3$Cl (10 mol) at room temperature. The reaction is heated to 83° C. until the reaction is complete. The reaction is cooled to 25° C. and EtOAc is charged. A solution of Na$_2$CO$_3$ (10 mol) in water is slowly added. The pH of the aqueous layer is >9 after the addition is complete. The layers are allowed to settle for 30 min, then separated. The organics is removed in vacuo and the product is isolated.

EXAMPLE 19

(R/S)-3-(4-Pyridin-3-yl-imidazol-1-yl)-butan-1-al (11)

To a stirred solution of 1.55 mL crotonaldehyde (17.1 mmol) in 9 mL of ethanol was added 2.1 mL (36 mmol) acetic acid and 2.61 g (18 mmol) 3-(1(3)H-imidazole-4-yl)-pyridine. The reaction was stirred for 48 hours, then extracted between ethyl acetate and 1/1 satd. sodium carbonate/brine. The organic layer was dried over sodium sulfate and concentrated in-vacuo to yield 3.49 g of the aldehyde as a mixture of aldehyde and its ethyl hemiacetal, and its hemihydrate.

EXAMPLE 20

3-(1(3)H-Imidazole-4-yl)-pyridine (20)

A slurry of 5 g (18 mmol) 3-(α-bromoacetyl)-pyridine hydrobromide in 50 mL formamide was heated to 180° C. for 8 hours. The reaction was cooled to room temperature, diluted with sodium bicarbonate, saturated with sodium chloride, and extracted with ethyl acetate. The ethyl acetate layer was dried over magnesium sulfate, conventrated in-vacuo, and the product was taken up in acetone and hydrochloric acid in dioxane was added. The product 20 was filtered and isolated as its bis-hydrochloric acid salt in 88% (3.4 g).

EXAMPLE 21

3-(1(3)H-Imidazole-4-yl)-pyridine (20)

1-trityl-4-iodoimidazole (7.4 kg, 17 mol) was dissolved in 55L tetrahydrofuran, and ethylmagnesium bromide (20L, 0.95M in methylt-butylether) was added over 20 min at 25° C. and the reaction was stirred for 1.5 hours. Zinc chloride (2.75 kg, 20.3 mol) was added and the reaction was again stirred for 1.5 hours. 3-bromopyridine (1.7L, 17.2 mol) was added, followed by tetrakistriphenylphosphinpalladium(0) (84 g). The reaction was heated to 70° C. for 12 hours, then cooled to 0° C. and the solids were filtered. The solids were suspended in dichloromethane and ethylenediaminetetraacetic acid (EDTA) and 30% sodium hydroxide in water was added to adjust the pH to 8. The layers were separated, more EDTA was added, and the procedure was repeated twice more. The organic layer was then washed with water, and concentrated to 5L. The solids were filtered to give 3.3 kg of 1-trityl-4-(3-pyridino)imidazole. This solid was dissolved in ethanol (33L), heated to 50° C., and 3.5L concentrated hydrochloric acid was added over 15 minutes. The reaction was stirred for 1.5 hours, then cooled to 0° C. and the solids were filtered. The filter cake was slurried in methyt-butylether and filtered to provide 1.77 kg of product (20) as its bis hydrochloric acid salt (8.2 mol, 48%).

EXAMPLE 22

3-(1(3)H-Imidazole-4-yl)-pyridine (20)

To potassium acetate (370 mg) and formamidine acetate (720 mg) in 5 mL dimethylformamide was added 3-(α-bromoacetyl)-pyridine hydrobromide (270 mg) and the reaction was heated to 65° C. The reaction was stirred for 24 hours, then cooled to room temperature.

EXAMPLE 23

3-(1 (3)H-Imidazole-4-yl)-pyridine (20)

To a degassed solution of KOH (4 mmol) and tetrabutylammonium iodide in DMF is added tetrakis(triphenylphosphine)palladium(0) (0.05 mmol), 1-trityl-4-iodoimidazole (1.5 mmol), and diethyl-3-pyridylborane, and the reaction is refluxed for 24 hours. The reaction is concentrated, and the residue is partitioned between sodium hydroxide basified brine and ethyl acetate. The organic layer is dried over sodium sulfate, and concentrated. The residue is dissolved in ethanol, heated to 50° C., and concentrated hydrochloric acid is added. The reaction is stirred for 1.5 hours, then cooled to 0° C. and the solids are filtered. The filter cake is slurried in methyt-butylether and filtered to provide the product (20) as its bis hydrochloric acid salt.

EXAMPLE 24

3(R)-1-Tertbutyldimethylsiloxy-3-butanol (28)

To a solution of 3(R)-1,3-butandiol (27) (29.3 g, 325 mmol) and imidazole (14.4 g, 211 mmol) in 150 mL dichloromethane was added a solution of tertbutyldimethylsilyl chloride (24.5 g, 162 mmol) in 50 mL dichloromethane at 0° C. over 1 h. The reaction was stirred for an additional 15 min, then washed 3 times with water, the organic layer was dried over sodium sulfate and concentrated in vacuo to provide 32.5 g of material.

EXAMPLE 25

3(R)-1-Tertbutyidimethylsiloxy-3-mesyloxybutane (29)

To a solution of 3(R)-1-tertbutyidimethylsiloxy-3-butanol (28) (20.5 g, 100 mmol) and triethylamine (16.7 mL, 120 mmol) in 200 mL dichloromethane was added mesyl chloride (8.5 mL, 110 mmol) at 0° C. The reaction was warmed to 25° C. and stirred for 1 hour. The reaction was rinsed 3 times with water, then dried over sodium sulfate and concentrated in vacuo to provide 27.7 g of material.

EXAMPLE 26

3-[1-[(1R)-3-tertbutyldimethylsiloxy-1-methylpropyl]-1H-imidazol-4-yl]-pyridine (30)

To a solution of 3(R)-1-tertbutyldimethylsiloxy-3-mesyloxybutane (29) (4.14 g, 14.7 mmol) and 3-(1(3)H-imidazole-4-yl)-pyridine bishydrochloride (20) (3.52 g, 16 mmol) in 40 mL of dimethylformamide was added 2.0 g sodium hydride (51 mmol). The reaction was heated to 80° C. for 18 h. To the reaction was added tertbutyldimethylsilyl chloride (4.0 g, 26.4 mmol) and imidazole (1.9 g, 27.9 mmol). The reaction was stirred an additional 1 h, then quenched with water and partitioned between ethyl acetate and brine. The organic layer was dried over sodium sulfate, and concentrated in vacuo to provide 2.39 g of material.

EXAMPLE 27

3-[1-[(1R)-3-hydroxy-1-methylpropyl]-1H-imidazol-4-yl]-pyridine (31)

To a solution of 3-[1-[(1R)-3-tertbutyldimethylsiloxy-1-methylpropyl]-1H-imidazol-4-yl]-pyridine (30) (1.12 g, 3.24 mmol) in 4 mL tetrahydrofuran was added 4 mL of 1M tetrabutylammonium flouride, and the reaction was stirred for 10 min. Hydrochloric acid in ethanol was added, followed by isopropyl ether. The solids were collected by filtration and recrystallized from acetonitrile to provide 0.51 g of product.

EXAMPLE 28

Bis(1 1-Dimethylethyl) 1-[(3R)-3-[4-(3-pyridinyl)-1H-imidazol-1-yl]butyl]-1,2-hydrazinedicarboxylate (32)

To a solution of 3-[1-[(1R)-3-tertbutyldimethylsiloxy-1-methylpropyl]-1H-imidazol-4-yl]-pyridine (31) (0.42 g, 1.7 mmol) in 6 mL tetrahydrofuran was added triphenylphosphine (0.49 g, 1.9 mmol). The solution was cooled to 0° C., and dit-butylazadicarboxylate (0.43 g, 1.9 mmol) was added. The reaction was warmed to 25° C. and stirred for 18 h. The reaction was partitioned between ethyl acetate and water, the organic layer was dried over sodium sulfate, and the solvent was evaporated in vacuo to yield 1.89 g of material.

EXAMPLE 29

3-[1-[(1R)-3-Hydrazino-1-methylpropyl]-1H-imidazol-4-yl]-pyridine (16)

To a solution of bis(1,1-dimethylethyl) 1-[(3R)-3-[4-(3-pyridinyl)-1H-imidazol-1-yl]butyl]-1,2-hydrazinedicarboxylate (32) in methanol was added 6N hydrochloric acid. The reaction was heated to 50° C. and stirred 18 h.

EXAMPLE 30

(1,1-Dimethylethyl)1-[(3R)-3-[4-(3-pyridinyl)-1H-imidazol-1-yl]butyl]hydrazone-(33)

(R/S)-3-(4-pyridin-3-yl-imidazol-1-yl)-butan-1-al (11) (1 mmol) is dissolved in 10 mL HOAc and t-butyl hydrazinecarboxylate (1.1 mmol) is added. After 1 h, the reaction is poured into 25 g sodium carbonate in 25 mL water and 30 mL EtOAc. The water layer is removed, the organics are washed with brine, and dried over sodium sulfate. The solvent is removed in vacuo to leave product (33).

EXAMPLE 31

(1,1-Dimethylethyl)1-[(3R)-3-[4-(3-pyridinyl)-1H-imidazol-1-yl]butyl]-2-hydrazinecarboxylate (32)

(1,1-Dimethylethyl)1-[(3R)-3-[4-(3-pyridinyl)-1H-imidazol-1-yl]butyl]hydrazone-2-carboxylate (33) (1 mmol) is dissolved in 10 mL HOAc and NaHB(OAc)$_3$ (5 mmol) is added at 25° C. After 2 h, the reaction is poured into sodium carbonate in water and EtOAc. The water layer is removed, the organics are washed with brine, and dried over sodium sulfate. The solvent is removed in vacuo to leave the product (32).

EXAMPLE 32

3-[1-[(1R)-3-hydrazino-1-methylpropyl]-1H-imidazol-4-yl]-pyridine (16)

To a solution of (1,1-dimethylethyl)1-[(3R)-3-[4-(3-pyridinyl)-1H-imidazol-1-yl]butyl]-2-hydrazinecarboxylate (32) in methanol is added 6N hydrochloric acid. The reaction is heated to 50° C. and stirred 18 h.

EXAMPLE 33

(1,1-Dimethylethyl)1-[(3R)-3-[4-(3-pyridinyl)-1H-imidazol-1-yl]butyl]-2-hydrazinecarboxylate (32)

(R/S)-3-(4-pyridin-3-yl-imidazol-1-yl)-butan-1-al (11) (1 mmol) is dissolved in 10 mL HOAc and t-butyl hydrazinecarboxylate (1.1 mmol) is added. After 1 h, NaHB(OAc)$_3$ (5 mmol) is added at 25° C. After 2 h, the reaction is poured into sodium carbonate in water and EtOAc. The water layer is removed, the organics are washed with brine, and dried over sodium sulfate. The solvent is removed in vacuo to leave the product (32).

EXAMPLE 34

(3aS,4R,7R,8S,9S,10R,11R,13R, 15R,15aR)-10-[[2-O-Acetyl-3,4,6-trideoxy-3-(dimethylamino)-β-D-xylo-hexopyranosyl]oxy]-2H-Oxacyclotetradecino[4,3-d]oxazole-2,6,14(1H,7H)-trione 4-ethyldecahydro-8-hydroxy-11-methoxy-3a, 7,9,11, 13,15-hexamethyl-1-[[(3R)-3-[4-(3-pyridinyl)-1H-imidazol-1-yl]butyl]amino]-14-O-methyloxime (13)

A 3- necked 12L round bottomed flask equipped with overhead stirrer, temperature probe, and nitrogen inlet was charged with 314 g (0.447 mol) of 01 g 2',4"-Bis-O-acetyl-9-deoxo-9-methoxyimino-11-deoxy-11-hydrazo-5-O-desosaminyl-6-O-methylerythronolide A, 11,12-carbamate (10) and 2.5L of methylene chloride, 0.628L acetic acid. To the clear solution was charged 292 g (1.342 mol, 3.0 equivalents) 3-(1(3)H-imidazole-4-yl)-pyridine bishydrochloride. This yellow suspension was stirred at room temperature for 5–10 minutes, then 42 mL (0.505 mol, 1.13 equivalents) of crotonaldehyde (99%) was added in one charge. The reaction slurry stirred over night at room temperature or greater than 25 hrs. The reaction was assayed for conversion to (3aS,4R,7R,8S,9S,10R,11R,13R,15R,15aR)-10-[[2-O-Acetyl-3,4,6-trideoxy-3-(dimethylamino)-β-D-xylo-hexopyranosyl]oxy]-2H-Oxacyclotetradecino[4,3-d]oxazole-2,6,14(1H,7H)-trione 4-ethyldecahydro-8-hydroxy-11-methoxy-3a,7,9,11,13,15-hexamethyl-1-[[(3R)-3-[4-(3-pyridinyl)-1H-imidazol-1-yl]butylidene]amino]-14-O-methyloxime (12). To the reaction was added 758 g (3.58 mol, 8.0 equivalents) sodium triacetoxiborohydride, temperature maintained 20–25° C. The reaction stirred 2–2.5 hrs. The reaction was cooled to less than 100° C. and quenched with 2500 mL city water, mild foaming and temperature increase occurred. The internal temperature was cooled to 5–100° C. and the solution was basified to 8.5–9.0 using 600 g sodium hydroxide pellets, internal temperature exothermed to 28° C. The layers were separated and the organic layer was washed with brine. The oranic layer was vac. concentrated to an amber foamy solid. Weight recovery of the title compound was 91%, (367.3 g).

EXAMPLE 35

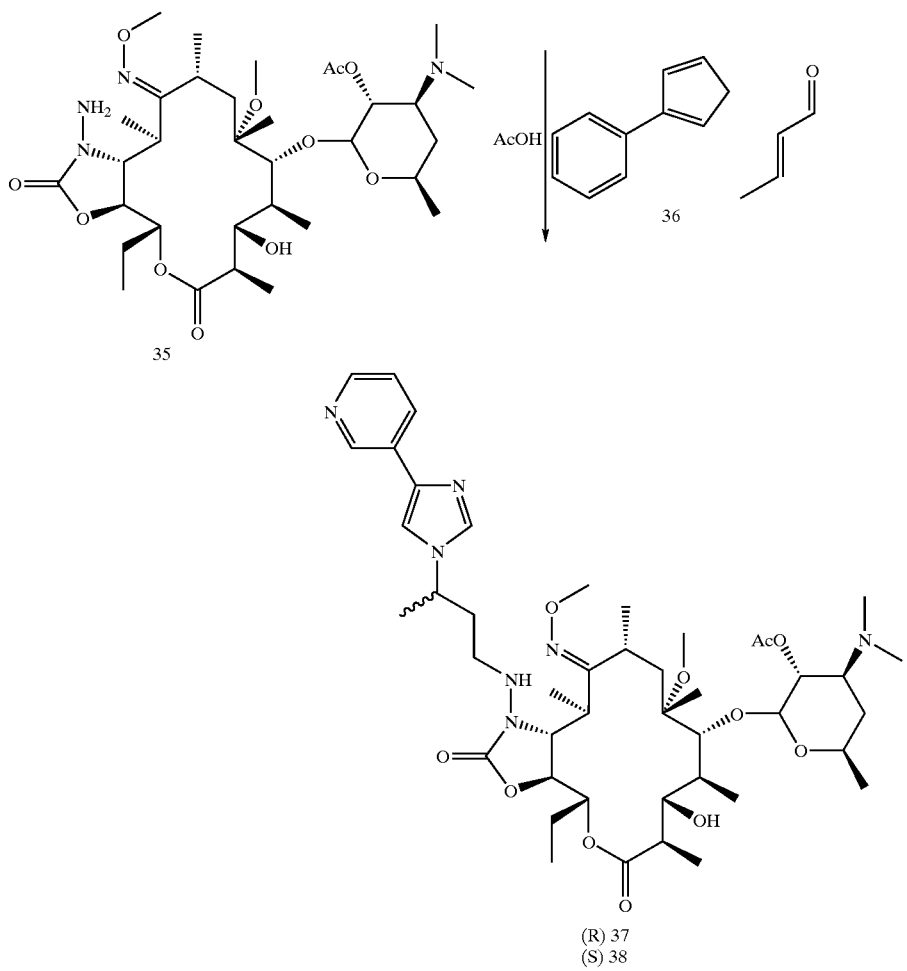

To a 50 ml flask contianing 14 ml of acetic acid was added a solid mixture of 1.24 g (26) and 2 g (25). The mixture was stirred for 15 minutes before all solids were dissolved. Then 260 ml of crotonaldehyde was added in one portion. No temperature change were observed during addition or during the deration of the condensation. After 3 hours when tests showed no crotonaldehyde imine, 4.8 g of sodium triacetoxyborohydride was added to the reaction. The mixture was then stirred at room temperature for 2.5 hours. The mixture was diluted with 50 ml of water and stirred for 30 minutes. The pH was measured at ~2. The pH was adjusted to 9 with ~19 ml of 40% aqueous NaOH (Internal temperature went up to 35° C. shortly after first addition of NaOH, The mixture was cooled in an ice water bath and the temperature was maintained below 30° C. for the remainder of the pH adjustment).

The aqueous layer was then extracted twice with methylene chloride. Then an additional extraction with methylene chloride was done but the organic layer collected separately. TLC analysis of the first two extractions versus the third showed no products extracted in the third extraction. The first two extractions were washed with brine, dried over sodium sulfate, filtered and evaporated to give 2.53 g of a crude mixture of 37 and 38 as a pale yellow solid.

What is claimed is:
1. A process of preparing a compound of the formula

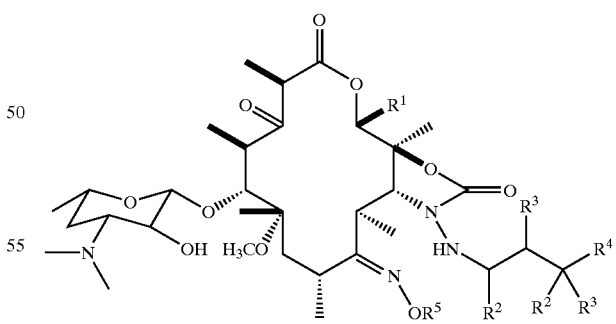

(15)

wherein:
$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from the group consisting of hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from the group consisting of $C_1$–$C_4$ alkyl, $C_1$–$C_4$ alkoxy and $C_1$–$C_4$ alkylthio groups, halogen atoms, hydroxyl groups, trifluoromethyl, and cyano; or $R^1$ is a formula (2) as shown below

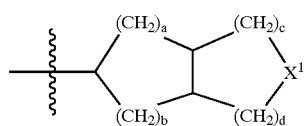

(a)

wherein $X^1$ is O, S or —$CH_2$—, a, b, c, and d are each independently selected from an integer ranging from 0 to 2 and a+b+c+d≦5; or $R^1$ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either or which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and each $R^2$ and $R^3$ is independently H or $C_1$–$C_6$ alkyl; and each $R^4$ is independently $C_6$–$C_{10}$ aryl or 5 to 10 membered heterocycle, wherein said aryl and heterocycle groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —S(O)$_n$($C_1$–$C_{10}$ alkyl) wherein n is an integer ranging from 0 to 2, and $SO_2NR^2R^3$; and $R^5$ is H or $C_1$–$C_{10}$ alkyl, wherein 1 to 3 carbons of said alkyl are optionally replaced by a heteroatom selected from the group consisting of O, S, and $NR^2$, and said alkyl group is optionally replaced by 1 to 3 substituents independently selected from the group consisting or —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —S(O)$_n$($C_1$–$C_{10}$ alkyl) wherein n is an integer ranging from 0 to 2, and $SO_2NR^2R^3$;

which comprises treating a compound of the formula

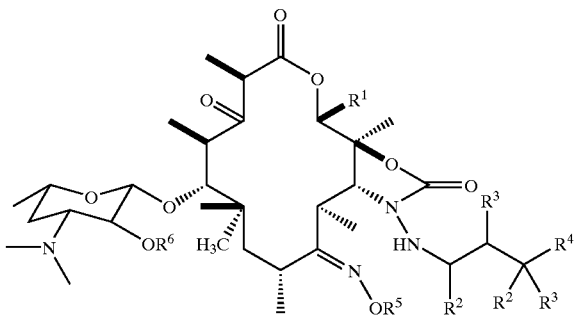

(14)

wherein
$R^1$–$R^5$ are as defined above; and
$R^6$ is —C(O)$R^4$, or $C_1$–$C_{18}$ alkanoyl, wherein one or two carbons in the alkyl portion of said alkanoyl may be optionally replaced by a heteroatom selected from the group consisting of O, S, and $NR^2$;
with a nucleophile to cleave the $R^6$ protecting group.

2. The reaction of claim 1 wherein the nucleophile is selected from the group consisting of ammonium hydroxide, monoalkyl amine, dialkylamine, alkanethiol, and hydroxide in a solvent selected from the group consisting of water, methanol, ethanol, isopropanol, tertbutanol, dimethylformamide, N-methylpyrrolidinone, acetonitrile, dimethylacetamide, tetrahydrofuran, dimethyl sulfoxide, dioxane dimethoxyethane, dichloromethane, tetrachloroethane, dichloroethane, ethylacetate and toluene.

3. The reaction of claim 1 wherein cleavage of $R^6$ takes place during solvolysis in alcoholic solvents selected from the group consisting of water, methanol, ethanol, isopropanol, and tert-butanol with the addition of base, to accelerate the reaction, selected from the group consisting of sodium carbonate, sodium bicarbonate, potassium carbonate, potassium hydroxide, sodiumhydroxide, potassium fluoride and barium hydroxide.

4. The reaction of claim 1 wherein cleavage of $R^6$ takes place in methanol with potassium carbonate.

5. The process according to claim 1, wherein said compound of formula (14) is prepared by oxidizing a compound of formula

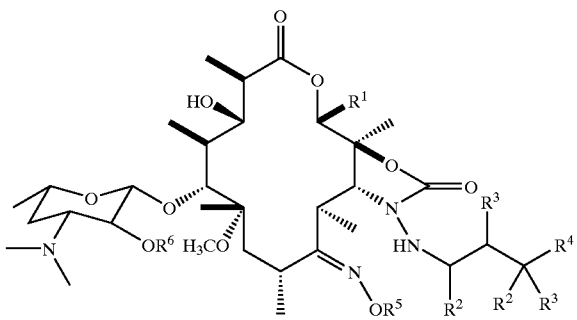

(13)

under Swern conditions
wherein:
$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5-C_8$ cycloalkylalkyl group wherein the alkyl group is an alpha-branched $C_2-C_5$ alkyl group; a $C_3-C_8$ cycloalkyl or $C_5-C_8$ cycloalkenyl group, either of which may optionally be substituted by methyl or one to three groups independently selected from the group consisting of hydroxy, $C_1-C_4$ alkyl, and halo; or a 3 to 6 membered oxygen or sulphur containing heterocyclic ring which may be saturated, or fully or partially unsaturated and which may optionally be substituted by one to three $C_1-C_4$ alkyl groups or halo atoms; or $R^1$ is phenyl which may be optionally replaced with one to three groups independently selected from the group consisting of $C_1-C_4$ alkyl, $C_1-C_4$ alkoxy $C_1-C_4$ alkylthio groups, halogen atoms, hydroxyl groups, trifluoromethyl, and cyano; or $R^1$ is a formula (a) as shown below

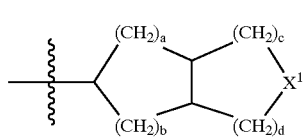
(a)

wherein $X^1$ is O, S or —$CH_2$—, a, b, c, and d are each independently selected from an integer ranging from 0 to 2 and a+b+c+d≦5; or $R^1$ is $CH_2R^{24}$, wherein $R^{24}$ is H, $C_1-C_8$alkyl, $C_2-C_8$alkenyl, $C_2-C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3-C_8$cycloalkyl or $C_5-C_8$cycloalkenyl either of which may be optionally replaced by methyl or one to three $C_1-C_4$alkyl groups or halo atoms; or a 3 to 6 membered oxygen or sulphur containing heterocyclic ring which may be saturated or fully or partially unsaturated and which may optionally be substituted by one to three $C_1-C_4$alkyl groups or halo atoms; or a group of the formula $SR^{23}$ wherein $R^{23}$ is $C_1-C_8$alkyl, $C_2-C_8$alkenyl, $C_2-C_8$alkynyl, $C_3-C_8$cycloalkyl, $C_5-C_8$cycloalkenyl, phenyl or substituted phenyl wherein the substituent is $C_1-C_4$alkyl, $C_1-C_4$alkoxy or halo, or a 3 to 6 membered oxygen or sulphur-containing heterocyclic ring which may be saturated, or fully or partially unsaturated and which may optionally be substituted by one to three $C_1-C_4$alkyl groups or halo atoms; and each $R^2$ and $R^3$ is independently H or $C_1-C_6$ alkyl; and each $R^4$ is independently $C_6-C_{10}$ aryl or 5 to 10 membered heterocycle, wherein said aryl and heterocycle groups are optionally replaced by 1 to 3 substituents independently selected from the group consisting of —C(O)O($C_1-C_{10}$ alkyl), $C_1-C_{10}$ alkoxy, $C_1-C_{10}$ alkanoyl, halo, nitro, cyano, 5 to 10 membered heterocycle, $C_6-C_{10}$ aryl, $C_1-C_{10}$ alkyl, —$NR^2R^3$, —$S(O)_n(C_1-C_{10}$ alkyl) wherein n is an integer ranging from 0 to 2, and $SO_2NR^2R^3$; and $R^5$ is H or $C_1-C_{10}$ alkyl, wherein 1 to 3 carbons of said alkyl are optionally replaced by a heteroatom selected from O, S, and $NR^2$, and said alkyl group is optionally replaced by 1 to 3 substituents independently selected from the group consisting of —C(O)O($C_1-C_{10}$ alkyl), $C_1-C_{10}$ alkoxy, $C_1-C_{10}$ alkanoyl, halo, nitro, cyano, 5 to 10 membered heterocycle, $C_6-C_{10}$ aryl, $C_1-C_{10}$ alkyl, —$NR^2R^3$, —$S(O)_n(C_1-C_{10}$ alkyl) wherein n is an integer ranging from 0 to 2, and $SO_2NR^2R^3$; and $R^6$ is H, —$C(O)R^4$, or $C_1-C_{18}$ alkanoyl, wherein one or two carbons in the alkyl portion of said alkanoyl may be optionally replaced by a heteroatom selected from the group consisting of O, S, and $NR^2$.

6. The process according to claim 5, wherein (a) dimethylsulfoxide is activated with an activating agent selected from the group consisting of oxalyl chloride, trifluoroacetic anhydride, sulfuryl chloride and thionyl chloride followed by addition of compound 13 in an inert solvent selected from the group consisting of dichloromethane, dichloroethane and tetrachloroethane; and (b) trialkylamine base is added after a time interval between about 5 minutes and 24 hours at a temperature range of about –80° C. to 50° C.

7. The process according to claim 5 wherein compound of formula 13 and dimethyl sulfoxide are premixed in an inert solvent followed by the addition of an activating agent and followed later with trialkylamine base.

8. The process according to claim 7 wherein a compound of formula (13) and dimethylsulfoxide are premixed at about 0° C. followed by the addition of trifluoroacetic anhydride.

9. The process according to claim 8 wherein triethylamine is added about 1½ to 2½ hours later and the reaction is then warmed to room temperature.

10. The process according to claim 5 wherein a compound of formula 13 is prepared by the reduction of a compound of formula

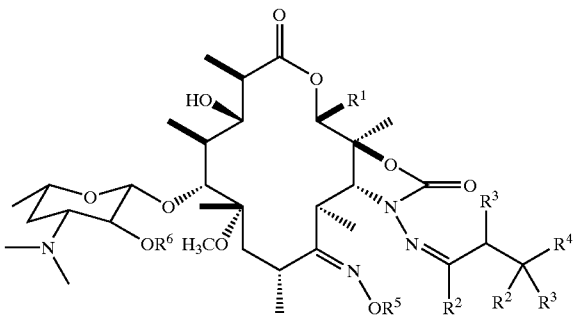
(12)

with a metal hydride reducing agent selected from sodium triacetoxyborohydride or sodium cyanoborohydride under acidic conditions, Wherein in formula (12):

$R^1$ is an alpha-branched $C_3-C_8$ alkyl, alkenyl, alkynyl, alkoxyalkyl or alkylthioalkyl group any of which may optionally be substituted by one to three hydroxyl groups; a $C_5-C_8$ cycloalkylalkyl group wherein the alkyl group is an alpha-branched $C_2-C_5$ alkyl group; a $C_3-C_8$ cycloalkyl or $C_5-C_8$ cycloalkenyl group, either of which may optionally be substituted by methyl or one to three groups independently selected from the group consisting of hydroxy, $C_1-C_4$ alkyl, and halo; or a 3 to 6 membered oxygen or sulphur containing heterocyclic ring which may be saturated, or fully or partially unsaturated and which may optionally be substituted by one to three $C_1-C_4$ alkyl groups or halo atoms; or $R^1$ is phenyl which may be optionally replaced with one to three groups independently selected from the group consisting of $C_1-C_4$ alkyl, $C_1-C_4$ alkoxy $C_1-C_4$ alkylthio groups, halogen atoms, hydroxyl groups, trifluoromethyl, and cyano; or $R^1$ is a formula (a) as shown below

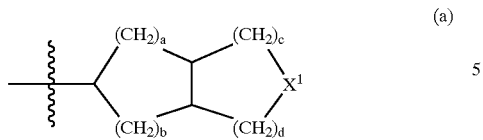

(a)

wherein $X^1$ is O, S or —CH$_2$—, a, b, c, and d are each independently selected from an integer ranging from 0 to 2 and $a+b+c+d \leq 5$; or $R^1$ is CH$_2$R$^{24}$, wherein R$^{24}$ is H, C$_1$–C$_8$alkyl, C$_2$–C$_8$alkenyl, C$_2$–C$_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a C$_3$–C$_8$cycloalkyl or C$_5$–C$_8$cycloalkenyl either or which may be optionally replaced by methyl or one to three C$_1$–C$_4$alkyl groups or halo atoms; or a 3 to 6 membered oxygen or sulphur containing heterocyclic ring which may be saturated or fully or partially unsaturated and which may optionally be substituted by one to three C$_1$–C$_4$alkyl groups or halo atoms; or a group of the formula SR$^{23}$ wherein R$^{23}$ is C$_1$–C$_8$alkyl, C$_2$–C$_8$alkenyl, C$_2$–C$_8$alkynyl, C$_3$–C$_8$cycloalkyl, C$_5$–C$_8$cycloalkenyl, phenyl or substituted phenyl wherein the substituent is C$_1$–C$_4$alkyl, C$_1$–C$_4$alkoxy or halo, or a 3 to 6 membered oxygen or sulphur-containing heterocyclic ring which may be saturated, or fully or partially unsaturated and which may optionally be substituted by one to three C$_1$–C$_4$alkyl groups or halo atoms; and each R$^2$ and R$^3$ is independently H or C$_1$–C$_6$ alkyl; and each R$^4$ is independently C$_6$–C$_{10}$ aryl or 5 to 10 membered heterocycle, wherein said aryl and heterocyclic groups are optionally replaced by 1 to 3 substituents independently selected from the group consisting or —C(O)O(C$_1$–C$_{10}$ alkyl), C$_1$–C$_{10}$ alkoxy, C$_1$–C$_{10}$ alkanoyl, halo, nitro, cyano, 5 to 10 membered heterocycle, C$_6$–C$_{10}$ aryl, C$_1$–C$_{10}$ alkyl, —NR$^2$R$^3$, —S(O)$_n$(C$_1$–C$_{10}$ alkyl) wherein n is an integer ranging from 0 to 2, and SO$_2$NR$^2$R$^3$; and R$^5$ is H or C$_1$–C$_{10}$ alkyl, wherein 1 to 3 carbons of said alkyl are optionally replaced by a heteroatom selected from the group consisting of O, S, and NR$^2$, and said alkyl group is optionally replaced by 1 to 3 substituents independently selected from the group consisting of —C(O)O (C$_1$–C$_{10}$ alkyl), C$_1$–C$_{10}$ alkoxy, C$_1$–C$_{10}$ alkanoyl, halo, nitro, cyano, 5 to 10 membered heterocycle, C$_6$–C$_{10}$ aryl, C$_1$–C$_{10}$ alkyl, —NR$^2$R$^3$, —S(O)$_n$(C$_1$–C$_{10}$ alkyl) wherein n is an integer ranging from 0 to 2, and SO$_2$NR$^2$R$^3$; and R$^6$ is H, —C(O)R$^4$, or C$_1$–C$_{18}$ alkanoyl, wherein one or two carbons in the alkyl portion of said alkanoyl may be optionally replaced by a heteroatom selected from the group consisting of O, S, and NR$^2$.

11. The process according to claim 10 wherein the reaction is run in acetic acid or an alcoholic solvent selected from ethanol, methanol, isopropanol and tert-butanol with an acidic additive selected from acetic and formic acid.

12. The process according to claim 11 wherein the reducing agent is sodium triacetoxyborohydride and the solvent is acetic acid.

13. The process according to claim 10 wherein said compound of Formula 12 is prepared by the reaction of a compound of the formula

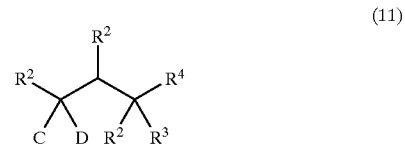

(11)

wherein:
R$^2$ to R$^4$ are defined above; and,
C and D together form oxo, or where C and D are independently hydroxy, C$_1$–C$_{10}$ alkoxy or C$_1$–C$_{10}$ acyloxy, with a compound of formula

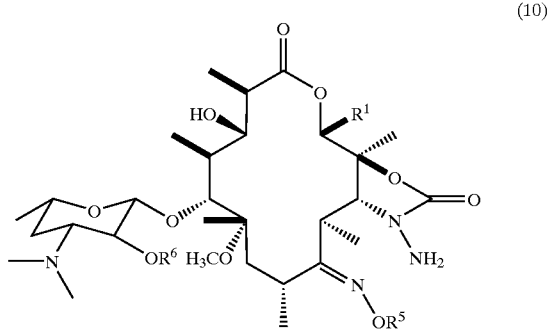

(10)

in a solvent under neutral or acidic conditions,

Wherein in formula (10):

R$^1$ is an alpha-branched C$_3$–C$_8$ alkyl, alkenyl, alkynyl, alkoxyalkyl or alkylthioalkyl group any of which may optionally be substituted by one to three hydroxyl groups; a C$_5$–C$_8$ cycloalkylalkyl group wherein the alkyl group is an alpha-branched C$_2$–C$_5$ alkyl group; a C$_3$–C$_8$ cycloalkyl or C$_5$–C$_8$cycloalkenyl group, either of which may optionally be substituted by methyl or one to three groups independently selected from the group consisting of hydroxy, C$_1$–C$_4$ alkyl, and halo; or a 3 to 6 membered oxygen or sulphur containing heterocyclic ring which may be saturated, or fully or partially unsaturated and which may optionally be substituted by one to three C$_1$–C$_4$ alkyl groups or halo atoms; or R$^1$ is phenyl which may be optionally replaced with one to three groups independently selected from the group consisting of C$_1$–C$_4$ alkyl, C$_1$–C$_4$ alkoxy, C$_1$–C$_4$ alkylthio groups, halogen atoms, hydroxyl groups, trifluoromethyl, and cyano; or R$^1$ is a formula (a) as shown below

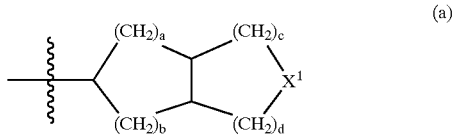

(a)

wherein $X^1$ is O, S or —CH$_2$—, a, b, c, and d are each independently selected from an integer ranging from 0 to 2 and $a+b+c+d \leq 5$; or R$^1$ is CH$_2$R$^{24}$, wherein R$^{24}$ is H, C$_1$–C$_8$alkyl, C$_2$–C$_8$alkenyl, C$_2$–C$_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups of by one to three halo atoms; or a $C_3$–$C_8$cycloalkyl or $C_5$–$C_8$cycloalkenyl either of which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$ . $C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and each $R^2$ and $R^3$ is independently H or $C_1$–$C_6$ alkyl; and each $R^4$ is independently $C_6$–$C_{10}$ aryl or 5 to 10 membered heterocycle, wherein said aryl and heterocyclic groups are optionally replaced by 1 to 3 substituents independently selected from the group consisting or —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n$($C_1$–$C_{10}$ alkyl) wherein n is an integer ranging from 0 to 2, and $SO_2NR^2R^3$; and $R^5$ is H or $C_1$–$C_{10}$ alkyl, wherein 1 to 3 carbons of said alkyl are optionally replaced by a heteroatom selected from O, S, and $NR^2$, and said alkyl group is optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n$($C_1$–$C_{10}$ alkyl) wherein n is an integer ranging from 0 to 2, and $SO_2NR^2R^3$; and $R^6$ is H, —C(O)$R^4$, or $C_1$–$C_{18}$ alkanoyl, wherein one or two carbons in the alkyl portion of said alkanoyl may be optionally replaced by a heteroatom selected from the group consisting of O, S, and $NR^2$.

14. The process according to claim 13 wherein the acidic conditions are acetic or formic acid as a solvent, or in a solvent selected from the group consisting of water, methanol ethanol, isopropanol, terbutanol, dimethylformamide, N-methylpyrrolidnone, acetonitrile, dimethylacetamide, tetrahydrofuran, dimethylsulfoxide, dioxane, dimethoxy ethane, dichloromethane, ethylacetate and toluene.

15. The process according to claim 13 wherein the neutral conditions are heating said reaction in said solvent without said acidic additive between about 80° C. to 110° C.

16. The process according to claim 13 wherein the reaction is run in acetic acid.

17. The process according to claim 13 wherein compound 10 is prepared by the reaction of a compound of formula

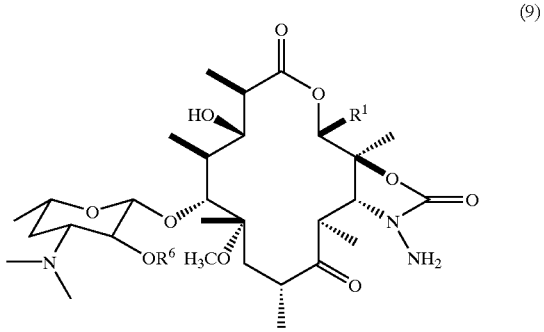

wherein:
$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_8$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from the group consisting of $C_1$–$C_4$ alkyl, $C_1$–$C_4$ alkoxy, $C_1$–$C_4$ alkylthio groups, halogen atoms, hydroxyl groups, trifluoromethyl, and cyano; or $R^1$ is a formula (a) as shown below

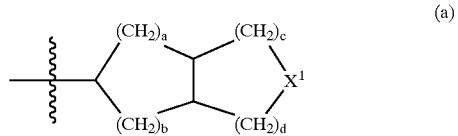

wherein $X^1$ is O, S or —$CH_2$—, a, b, c, and d are each independently selected from an integer ranging from 0 to 2 and a+b+c+d≦5; or $R^1$ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either of which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and each $R^4$ is independently $C_6$–$C_{10}$ aryl or 5 to 10 membered heterocycle, wherein said aryl and heterocycle groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —S(O)$_n$($C_1$–$C_{10}$ alkyl) wherein n is an integer ranging from 0 to 2, and SO$_2$NR$^2$R$^3$; and $R^6$ is H, —C(O)$R^4$, or $C_1$–$C_{18}$ alkanoyl, wherein one or two carbons in the alkyl portion of said alkanoyl may be optionally replaced by a heteroatom selected from O, S, and $NR^2$ with a reagent of the formula

H$_2$NOR$^5$ wherein $R^5$ is defined above, as its free base or acid addition salt in polar solvents with or without added base at a temperature between about 40° C. to 150° C.

18. The process according to claim 17 wherein said polar solvents are selected from the group consisting of methanol, ethanol, isopropanol, tert-butanol, dimethylformamide, N-methylpyrrolidinone, acetonitrile, dimethylacetamide, and dimethylsulfoxide and said base is chosen from pyridine, 2,6-lutidine, imidazole, amine bases, or dimethylaminopyridine.

19. The process according to claim 18 wherein the compound of formula H$_2$NOR$^5$ is methoxylamine hydrochloride.

20. The process according to claim 19 wherein the reaction is run in isopropanol.

21. The process according to claim 17 wherein Compound 9 is prepared by the reaction of a compound of formula

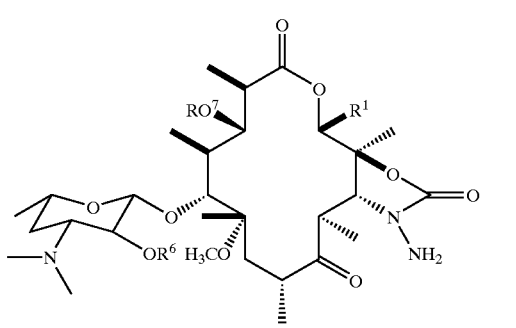

(2)

with an acid in a polar solvent, at a temperature of about −25° C. to 100° C.,
wherein in formula (2):

$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from the group consisting of $C_1$–$C_4$ alkyl, $C_1$–$C_4$ alkoxy, $C_1$–$C_4$ alkylthio groups, halogen atoms, hydroxyl groups, trifluoromethyl, and cyano; or $R^1$ is a formula (a) as shown below

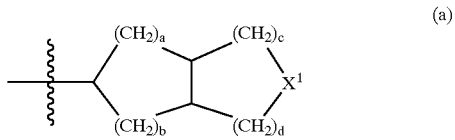

(a)

wherein $X^1$ is O, S or —CH$_2$—, a, b, c, and d are each independently selected from an integer ranging from 0 to 2 and a+b+c+d≦5; or $R^1$ is CH$_2$R$^{24}$, wherein R$^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either of which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula SR$^{23}$ wherein R$^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and each $R^4$ is independently $C_6$–$C_{10}$ aryl or 5 to 10 membered heterocycle, wherein said aryl and heterocycle groups are optionally replaced by 1 to 3 substituents independently selected from the group consisting or —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —NR$^2$R$^3$, —S(O)$_n$($C_1$–$C_{10}$ alkyl) wherein n is an integer ranging from 0 to 2, and SO$_2$NR$^2$R$^3$; and $R^6$ is H, —C(O)$R^4$, or $C_1$–$C_{18}$ alkanoyl, wherein one or two carbons in the alkyl portion of said alkanoyl may be optionally replaced by a heteroatom selected from O, S, and NR$^2$; and $R^7$ is a radical of formula

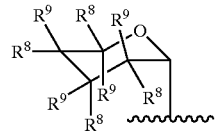

wherein each $R^8$ and $R^9$ are independently hydrogen, hydroxy, $C_1$–$C_6$ alkoxy, —OC(O)R$^4$, —OC(O)

NHNH$_2$, —OSi(R$^{10}$)$_3$, or C$_1$–C$_{18}$ O-alkanoyl, wherein one or two carbons in the alkyl portion of said alkanoyl may be optionally replaced by a heteroatom selected from O, S, and NR$^2$; and R$^8$ & R$^9$ may be taken together to form

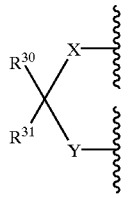

wherein:
X=O or S
Y=O or S
R$^{30}$, and R$^{31}$=H, C$_1$–C$_6$ alkyl, C$_6$–C$_{10}$ aryl, or R$^{30}$ and R$^{31}$ taken together form =O or =S
or R$^8$ & R$^9$ can be taken together to form

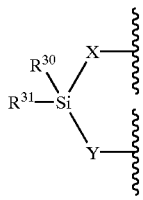

and each R$^{10}$ is independently C$_1$–C$_{10}$ alkyl or C$_6$–C$_{10}$ aryl.

22. The process according to claim 21, wherein the acids are selected from the group consisting of hydrochloric, hydrobromic, hydriodic, sulfuric, nitric, alkylsulfonic, tosic, triflic and trifluoroacetic acid and the polar solvent is chosen from water, methanol, ethanol, isopropanol, tert-butanol, dimethylformamide, N-methylacetamide, tetrahydrofuran, dimethlsulfoxide, acetic acid and formic acid.

23. The process according to claim 21 wherein the acid is hydrochloric acid.

24. The process according to claim 23 wherein the solvent is methanol.

25. The process according to claim 21, wherein compound 2 is prepared by the reaction of a compound of the formula

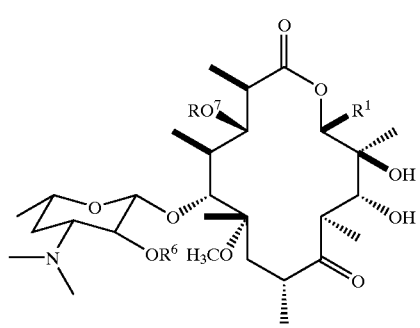

(1)

with a carbonyl source and base in an inert solvent, followed by treatment with hydrazine
Wherein in formula (1):
R$^1$ is an alpha-branched C$_3$–C$_8$ alkyl, alkenyl, alkynyl, alkoxyalkyl or alkylthioalkyl group any of which may optionally be substituted by one to three hydroxyl groups; a C$_5$–C$_8$ cycloalkylalkyl group wherein the alkyl group is an alpha-branched C$_2$–C$_5$ alkyl group; a C$_3$–C$_8$ cycloalkyl or C$_5$–C$_8$ cycloalkenyl group, either of which may optionally be substituted by methyl or one to three groups independently selected from hydroxy, C$_1$–C$_4$ alkyl, and halo; or a 3 to 6 membered oxygen or sulphur containing heterocyclic ring which may be saturated, or fully or partially unsaturated and which may optionally be substituted by one to three C$_1$–C$_4$ alkyl groups or halo atoms; or R$^1$ is phenyl which may be optionally replaced with one to three groups independently selected from the group consisting of C$_1$–C$_4$ alkyl, C$_1$–C$_4$ alkoxy, C$_1$–C$_4$ alkylthio groups, halogen atoms, hydroxyl groups, trifluoromethyl, and cyano; or R$^1$ is a formula (a) as shown below

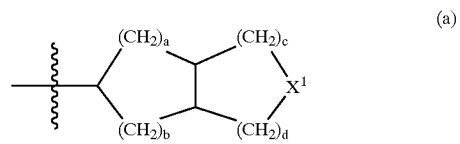

(a)

wherein X$^1$ is O, S or —CH$_2$—, a, b, c, and d are each independently selected from an integer ranging from 0 to 2 and a+b+c+d≦5; or R$^1$ is CH$_2$R$^{24}$, wherein R$^{24}$ is H, C$_1$–C$_8$alkyl, C$_2$–C$_8$alkenyl, C$_2$–C$_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a C$_3$–C$_8$cycloalkyl or C$_5$–C$_8$cycloalkenyl either or which may be optionally replaced by methyl or one to three C$_1$–C$_4$alkyl groups or halo atoms; or a 3 to 6 membered oxygen or sulphur containing heterocyclic ring which may be saturated or fully or partially unsaturated and which may optionally be substituted by one to three C$_1$–C$_4$alkyl groups or halo atoms; or a group of the formula SR$^{23}$ wherein R$^{23}$ is C$_1$–C$_8$alkyl, C$_2$–C$_8$alkenyl, C$_2$–C$_8$alkynyl, C$_3$–C$_8$cycloalkyl, C$_5$–C$_8$cycloalkenyl, phenyl or substituted phenyl wherein the substituent is C$_1$–C$_4$alkyl, C$_1$–C$_4$alkoxy or halo, or a 3 to 6 membered oxygen or sulphur-containing heterocyclic ring which may be saturated, or fully or partially unsaturated and which may optionally be substituted by one to three C$_1$–C$_4$alkyl groups or halo atoms; and each R$^4$ is independently C$_6$–C$_{10}$ aryl or 5 to 10 membered heterocycle, wherein said aryl and heterocyclic groups are optionally replaced by 1 to 3 substituents independently selected from the group consisting or —C(O)O(C$_1$–C$_{10}$ alkyl), C$_1$–C$_{10}$ alkoxy, C$_1$–C$_{10}$ alkanoyl, halo, nitro, cyano, 5 to 10 membered heterocycle, C$_6$–C$_{10}$ aryl, C$_1$–C$_{10}$ alkyl, —NR$^2$R$^3$, —S(O)$_n$(C$_1$–C$_{10}$ alkyl) wherein n is an integer ranging from 0 to 2, and SO$_2$NR$^2$R$^3$; and R$^6$ is H, —C(O)R$^4$, or C$_1$–C$_{18}$ alkanoyl, wherein one or two carbons in the alkyl portion of said alkanoyl may be optionally replaced by a heteroatom selected from O, S, and NR$^2$; and $R^7$ is a radical of formula

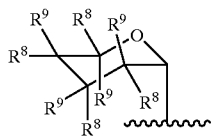

wherein each $R^8$ and $R^9$ are independently hydrogen, hydroxy, $C_1$–$C_6$ alkoxy, —OC(O)$R^4$, —OC(O)NHNH$_2$, —OSi($R^{10}$)$_3$, or $C_1$–$C_{18}$ O-alkanoyl, wherein one or two carbons in the alkyl portion of said alkanoyl may be optionally replaced by a heteroatom selected from O, S, and N$R^2$; and, $R^8$ & $R^9$ may be taken together to form

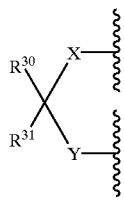

wherein:

X=O or S

Y=O or S $R^{30}$, and $R^{31}$=H, $C_1$–$C_6$ alkyl, $C_6$–$C_{10}$ aryl, or $R^{30}$ and $R^{31}$ taken together form =O or =S or $R^8$ & $R^9$ can be taken together to form

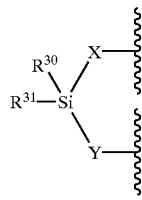

and each $R^{10}$ is independently $C_1$–$C_{10}$ alkyl or $C_6$–$C_{10}$ aryl.

26. The process according to claim 25 wherein the carbonyl source is selected from the group consisting of carbonyldiimidazole (CDI), phosgene, triphosgene, carbonyl bisbenzotriazole, carbonyl bishydroxybenzotriazole, and carbonyl bis-1,2,4-triazole.

27. The process according to claim 25 wherein the base is selected from the group consisting of 1,8-diazabicylco [5.4.0] undec-7-ene (DBU), 1,2-dimethyl-1,4,5,6-tetrahydropyrimidine, sodium hexamethyl disilazane, lithium diisopropylamide, potassium hexamethyl diisilazane, or tetramethyl guanidine in an inert solvent, selected from isopropylether, dimethylformamide, N-methylpyrrolidinone, acetonitrile, dimethylacetamide, tetrahydrofuran, dimethylsulfoxide, dioxane, dimethoxyethane, dichloromethane, tetrachloroethane, and dichloroethane.

28. The process according to claim 25 wherein said reaction is monitored for the formation of an intermediate of formula

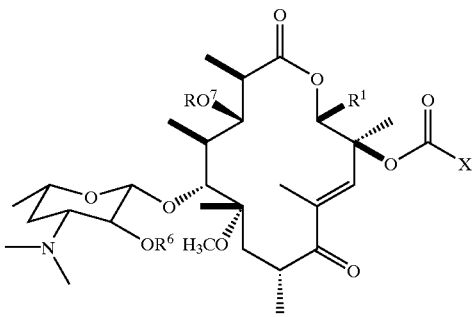

wherein:

$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from $C_1$–$C_4$ alkyl, $C_1$–$C_4$ alkoxy and $C_1$–$C_4$ alkylthio groups, halogen atoms, hydroxyl groups, trifluoromethyl, and cyano; or $R^1$ is a formula (a) as shown below

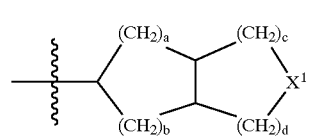

wherein $X^1$ is O, S or —CH$_2$—, a, b, c, and d are each independently selected from an integer ranging from 0 to 2 and a+b+c+d≦5; or $R^1$ is CH$_2$$R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either of which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula S$R^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and each R⁴ is independently $C_6$-$C_{10}$ aryl or 5 to 10 membered heterocycle, wherein said aryl and heterocyclic groups are optionally replaced by 1 to 3 substituents independently selected from the group consisting of —C(O)O($C_1$-$C_{10}$ alkyl), $C_1$-$C_{10}$ alkoxy, $C_1$-$C_{10}$ alkanoyl, halo, nitro, cyano, 5 to 10 membered heterocycle, $C_6$-$C_{10}$ aryl, $C_1$-$C_{10}$ alkyl, —NR²R³, —S(O)$_n$($C_1$-$C_{10}$ alkyl) wherein n is an integer ranging from 0 to 2, and SO₂NR²R³; and R⁶ is H, —C(O)R⁴, or $C_1$-$C_{18}$ alkanoyl, wherein one or two carbons in the alkyl portion of said alkanoyl may be optionally replaced by a heteroatom selected from O, S, and NR²; and R⁷ is a radical of formula

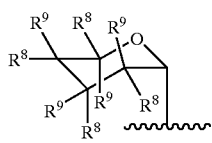

wherein each R⁸ and R⁹ are independently hydrogen, hydroxy, $C_1$-$C_6$ alkoxy, —OC(O)R⁴, —OC(O)NHNH₂, —OSi(R¹⁰)₃, or $C_1$-$C_{18}$ O-alkanoyl, wherein one or two carbons in the alkyl portion of said alkanoyl may be optionally replaced by a heteroatom selected from O, S, and NR²; and R⁸ & R⁹ may be taken together to form

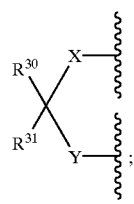

wherein:
X=O or S
Y=O or S
R³⁰, and R³¹=H, $C_1$-$C_6$ alkyl, $C_6$-$C_{10}$ aryl, or R³⁰ and R³¹ taken together form =O or =S
or R⁸ & R⁹ can be taken together to form

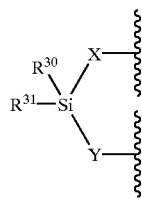

each R¹⁰ is independently $C_1$-$C_{10}$ alkyl or $C_6$-$C_{10}$ aryl, and

X is imidazole, 1,2,4-triazole, hydroxybenzotriazole, or benzotriazole.

29. The process according to claim 25 wherein when intermediate compound (5) is formed, hydrazine or hydrazine hydrate is added to the reaction between about −78° C. and 50° C.

30. The process according to claim 25 wherein the base is 1,8-diazabicylco[5.4.0] undec-7-ene (DBU) or 1,2-dimethyl-1,4,5,6-tetrahydro-pyrimidine.

31. The process according to claim 25 wherein the carbonyl source is CDI.

32. The process according to claim 5 wherein a compound of formula 13 is produced by the reaction of a compound of formula

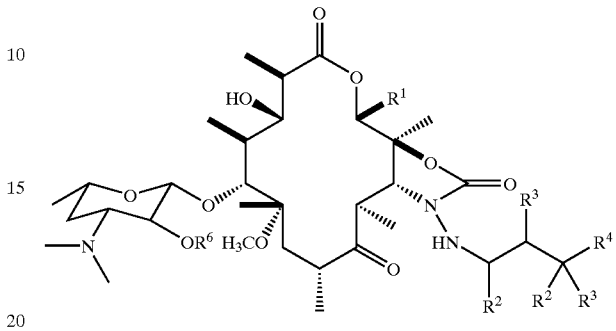

(19)

wherein:
R¹ is an alpha-branched $C_3$-$C_8$ alkyl, alkenyl, alkynyl, alkoxyalkyl or alkylthioalkyl group any of which may optionally be substituted by one to three hydroxyl groups; a $C_5$-$C_8$ cycloalkylalkyl group wherein the alkyl group is an alpha-branched $C_2$-$C_5$ alkyl group; a $C_3$-$C_8$ cycloalkyl or $C_5$-$C_8$ cycloalkenyl group, either of which may optionally be substituted by methyl or one to three groups independently selected from hydroxy, $C_1$-$C_4$ alkyl, and halo; or a 3 to 6 membered oxygen or sulphur containing heterocyclic ring which may be saturated, or fully or partially unsaturated and which may optionally be substituted by one to three $C_1$-$C_4$ alkyl groups or halo atoms; or R¹ is phenyl which may be optionally replaced with one to three groups independently selected from $C_1$-$C_4$ alkyl, $C_1$-$C_4$ alkoxy and $C_1$-$C_4$ alkylthio groups, halogen atoms, hydroxyl groups, trifluoromethyl, and cyano; or R¹ is a formula (a) as shown below

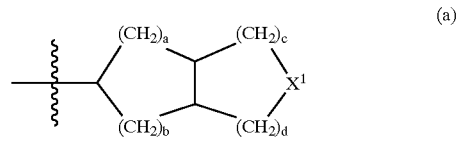

(a)

wherein X¹ is O, S or —CH₂—, a, b, c, and d are each independently selected from an integer ranging from 0 to 2 and a+b+c+d≦5; or R¹ is CH₂R²⁴, wherein R²⁴ is H, $C_1$-$C_8$alkyl, $C_2$-$C_8$alkenyl, $C_2$-$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$-$C_8$cycloalkyl or $C_5$-$C_8$cycloalkenyl either or which may be optionally replaced by methyl or one to three $C_1$-$C_4$alkyl groups or halo atoms; or a 3 to 6 membered oxygen or sulphur containing heterocyclic ring which may be saturated or fully or partially unsaturated and which may optionally be substituted by one to three $C_1$-$C_4$alkyl groups or halo atoms; or a group of the formula SR²³ wherein R²³ is $C_1$-$C_8$alkyl, $C_2$-$C_8$alkenyl, $C_2$-$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and each $R^2$ and $R^3$ is independently H or $C_1$–$C_6$ alkyl; and each $R^4$ is independently $C_6$–$C_{10}$ aryl or 5 to 10 membered heterocycle, wherein said aryl and heterocyclic groups are optionally replaced by 1 to 3 substituents independently selected from the group consisting or —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n$($C_1$–$C_{10}$ alkyl) wherein n is an integer ranging from 0 to 2, and $SO_2NR^2R^3$; and $R^6$ is H, —C(O)$R^4$, or $C_1$–$C_{18}$ alkanoyl, wherein one or two carbons in the alkyl portion of said alkanoyl may be optionally replaced by a heteroatom selected from O, S, and $NR^2$, with a reagent of the formula $H_2NOR^5$ wherein $R^5$ is defined above, as its free base or in acid addition salt form, with or without a base in a polar solvent at a temperature between about 40° C. to 150° C.

33. The process according to claim 32 wherein the base is selected from the group consisting of pyridine, 2,6-lutidine, imidazole, trialkylamine base, and dimethylaminopyridine in said polar solvent selected from the group consisting of methanol, ethanol, isopropanol, tert-butanol, dimethylformamide, N-methylpyrrolidinone, acetonitrile, dimethylacetamide, and dimethylformamide.

34. The process according to claim 32 wherein the compound of formula 19 is reacted with methoxylamine hydrochloride.

35. The process according to claim 32 wherein a compound of 19 is prepared by the reaction of a compound of formula (17)

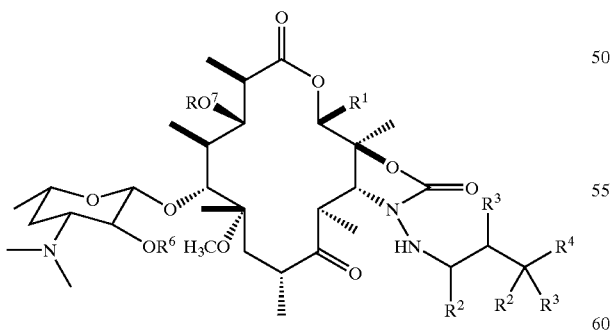

wherein:

$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from $C_1$–$C_4$ alkyl, $C_1$–$C_4$ alkoxy and $C_1$–$C_4$ alkylthio groups, halogen atoms, hydroxyl groups, trifluoromethyl, and cyano;

or $R^1$ is a formula (a) as shown below

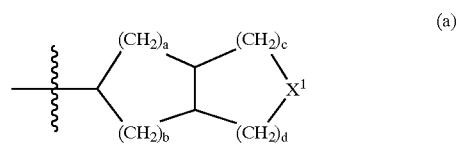

(a)

wherein $X^1$ is O, S or —$CH_2$—, a, b, c, and d are each independently selected from an integer ranging from 0 to 2 and $a+b+c+d \leq 5$; or $R^1$ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either of which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and each $R^2$ and $R^3$ is independently H or $C_1$–$C_6$ alkyl; and each $R^4$ is independently $C_6$–$C_{10}$ aryl or 5 to 10 membered heterocycle, wherein said aryl and heterocycle groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n$($C_1$–$C_{10}$ alkyl) wherein n is an integer ranging from 0 to 2, and $SO_2NR^2R^3$; and $R^6$ is H, —C(O)$R^4$, or $C_1$–$C_{18}$ alkanoyl, wherein one or two carbons in the alkyl portion of said alkanoyl may be optionally replaced by a heteroatom selected from O, S, and $NR^2$; and $R^7$ is a radical of formula

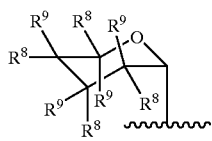

wherein each $R^8$ and $R^9$ are independently hydrogen, hydroxy, $C_1$–$C_6$ alkoxy, —OC(O)$R^4$, —OC(O)NHNH$_2$, —OSi($R^{10}$)$_3$, or $C_1$–$C_{18}$ O-alkanoyl, wherein one or two carbons in the alkyl portion of said alkanoyl may be optionally replaced by a heteroatom selected from O, S, and $NR^2$; and $R^8$ & $R^9$ may be taken together to form

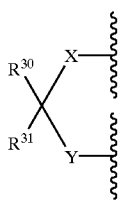

wherein:

X=O or S

Y=O or S $R^{30}$, and $R^{31}$=H, $C_1$–$C_6$ alkyl, $C_6$–$C_{10}$ aryl, or $R^{30}$ and $R^{31}$ taken together form =O or =S or $R^8$ & $R^9$ can be taken together to form

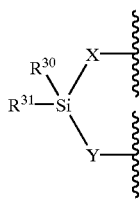

and each $R^{10}$ is independently $C_1$–$C_{10}$ alkyl or $C_6$–$C_{10}$ aryl, with acid in a polar solvent at a temperature of about −25° C. to 100° C.

36. The process according claim 35 wherein the acid with or without water is selected from the group consisting of hydrochloric, hydrobromic, hydriodic, sulfuric, nitric, alkylsulfonic, tosic, triflic and trifluoroacetic acid.

37. The process according to claim 36 wherein the polar solvents are selected from the group consisting of water, methanol, ethanol, isopropanol, tert-butanol, dimethylformamide, N-methylpyrrolidinone, acetonitrile, dimethylacetamide, tetrahydrofuran, dimethylsulfoxide, acetic acid and formic acid.

38. The process according to claim 36 wherein the acid is hydrochloric.

39. The process according to claim 38 wherein the solvent is methanol.

40. The process according to claim 36 wherein the compound of formula 17 is prepared by the reaction of compound

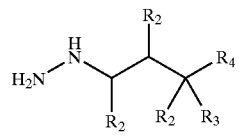

(16)

in an inert solvent at a temperature of about 0° C. to 150° C., with a compound of the formula

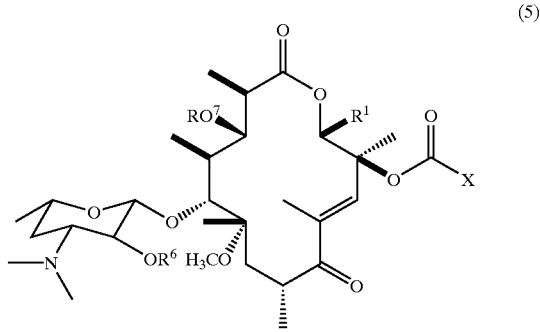

(5)

in an inert solvent at a temperature of about 0° C. to 150° C.

wherein in the formula (5):

$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from the group consisting of $C_1$–$C_4$ alkyl, $C_1$–$C_4$ alkoxy, $C_1$–$C_4$ alkylthio groups, halogen atoms, hydroxyl groups, trifluoromethyl, and cyano;

$R^1$ is a formula (a) as shown below

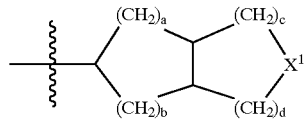

(a)

wherein $X^1$ is O, S or —CH$_2$—, a, b, c, and d are each independently selected from an integer ranging from 0 to 2 and a+b+c+d≦5; or $R^1$ is CH$_2R^{24}$, wherein $R^{24}$ is H, $C_1$–$C_8$ aalkyl, $C_2$–$C_8$ alkenyl, $C_2$–$C_8$ alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$ cycloalkyl or $C_5$–$C_8$cycloalkenyl either of which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and each $R^2$ and $R^3$ is independently H or $C_1$–$C_6$ alkyl; and each $R^4$ is independently $C_6$–$C_{10}$ aryl or 5 to 10 membered heterocycle, wherein said aryl and heterocycle groups are optionally replaced by 1 to 3 substituents independently selected from the group consisting or —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$alkyl, —$NR^2R^3$, —S(O)$_n$($C_1$–$C_{10}$ alkyl) wherein n is an integer ranging from 0 to 2, and $SO_2NR^2R^3$ each $R^4$ is independently $C_6$–$C_{10}$ aryl or 5 to 10 membered heterocycle, wherein said aryl and heterocyclic groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —S(O)$_n$($C_1$–$C_{10}$ alkyl) wherein n is an integer ranging from 0 to 2, and $SO_2NR^2R^3$; and $R^6$ is H, —C(O)$R^4$, or $C_1$–$C_{18}$ alkanoyl, wherein one or two carbons in the alkyl portion of said alkanoyl may be optionally replaced by a heteroatom selected from O, S, and $NR^2$; and $R^7$ is a radical of formula

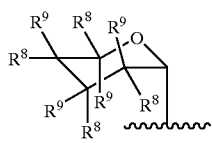

wherein each $R^8$ and $R^9$ are independently hydrogen, hydroxy, $C_1$–$C_6$ alkoxy, —OC(O)$R^4$, —OC(O)NHNH$_2$, —OSi($R^{10}$)$_3$, or $C_1$–$C_{18}$ O-alkanoyl, wherein one or two carbons in the alkyl portion of said alkanoyl may be optionally replaced by a heteroatom selected from O, S, and $NR^2$; and $R^8$ & $R^9$ may be taken together to form

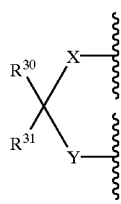

wherein:
X=O or S
Y=O or S $R^{30}$, and $R^{31}$=H, $C_1$–$C_6$ alkyl, $C_6$–$C_{10}$ aryl, or $R^{30}$ and $R^{31}$ taken together form =O or =S or $R^8$ & $R^9$ can be taken together to form

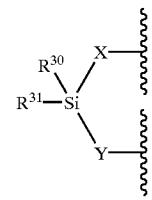

and each $R^{10}$ is independently $C_1$–$C_{10}$ alkyl or $C_6$–$C_{10}$ aryl, and X is imidazole, 1,2,4-triazole, hydroxybenzotriazole, or benzotriazole.

41. The process of claim 40 wherein the inert solvent is selected from isopropylether, dimethylforamide, N-methylpyrrolidinone, acetonitrile, dimethylacetamide, tetrahydrofuran, dimethylsulfoxide, dioxane, dimethoxyethane, dichloromethane, tetrachloroethane, and dichloroethane.

42. The process of claim 40 wherein the inert solvent is acetonitrile.

43. The process according to claim 13 wherein compound 10 is prepared by the reaction of a compound of formula

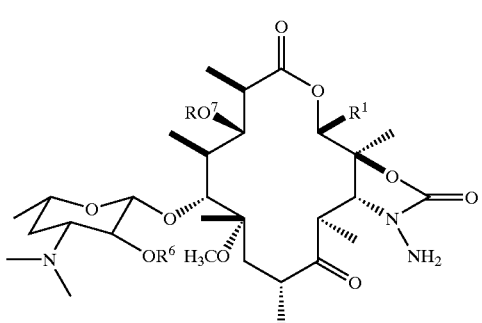

(2)

wherein:

$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from $C_1$–$C_4$ alkyl, $C_1$–$C_4$ alkoxy and $C_1$–$C_4$ alkylthio groups, halogen atoms, hydroxyl groups, trifluoromethyl, and cyano; or

117

$R^1$ is a formula (a) as shown below

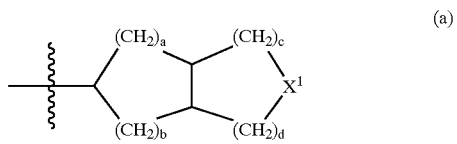

wherein $X^1$ is O, S or —$CH_2$—, a, b, c, and d are each independently selected from an integer ranging from 0 to 2 and a+b+c+d≦5, or $R^1$ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either or which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and each $R^4$ is independently $C_6$–$C_{10}$ aryl or 5 to 10 membered heterocycle, wherein said aryl and heterocycle groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n$($C_1$–$C_{10}$ alkyl) wherein n is an integer ranging from 0 to 2, and $SO_2NR^2R^3$; and $R^6$ is H, —$C(O)R^4$, or $C_1$–$C_{18}$ alkanoyl, wherein one or two carbons in the alkyl portion of said alkanoyl may be optionally replaced by a heteroatom selected from O, S, and $NR^2$; and $R^7$ is a radical of formula

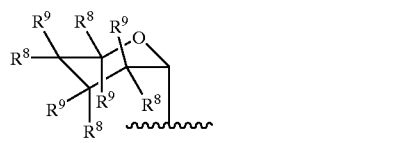

wherein each $R^8$ and $R^9$ are independently hydrogen, hydroxy, $C_1$–$C_6$ alkoxy, —OC(O)$R^4$, —OC(O)NHNH$_2$, —OSi($R^{10}$)$_3$, or $C_1$–$C_{18}$ O-alkanoyl, wherein one or two carbons in the alkyl portion of said alkanoyl may be optionally replaced by a heteroatom selected from O, S, and $NR^2$; and

118

$R^8$ & $R^9$ may be taken together to form

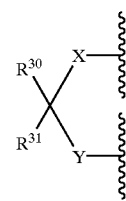

wherein:
X═O or S
Y═O or S
$R^{30}$, and $R^{31}$═H, $C_1$–$C_6$ alkyl, $C_6$–$C_{10}$ aryl, or $R^{30}$ and $R^{31}$ taken together form ═O or ═S
or $R^8$ & $R^9$ can be taken together to form

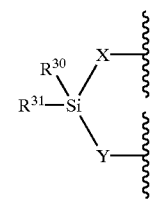

and each $R^{10}$ is independently $C_1$–$C_{10}$ alkyl or $C_6$–$C_{10}$ aryl,
with a reagent of the formula

H$_2$NOR$^5$ wherein $R^5$ is defined above,
as its acid addition salt in polar solvents with or without added base at a temperature between about 40° C. to 150° C.

44. The process according to claim 43 wherein said polar solvents are selected from the group consisting of methanol, ethanol, isopropanol, tert-butanol, dimethylformamide, N-methylpyrrolidinone, acetonitrile, dimethylacetamide, and dimethylsulfoxide and said base is chosen from the group consisting of pyridine, 2,6-lutidine, imidazole, amine bases, and dimethylaminopyridine.

45. The process according to claim 44 wherein the compound of formula H$_2$NOR$^5$ is methoxylamine hydrochloride.

46. The process according to claim 45 wherein the reaction is run in isopropanol.

47. The process according to claim 10 wherein a compound of formula 12 is prepared by the reaction of a compound of formula (20)

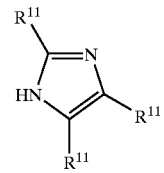

wherein:
each $R^{11}$ is independently selected from the group consisting of H, —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alky, —$NR^2R^3$, —S(O)$_n$(C$_1$–C$_{10}$ alkyl) wherein n is an integer ranging from 0 to 2, and SO$_2$NR$^2$R$^3$; wherein said aryl and heterocyclic groups are optionally replaced by 1 to 3 substituents independently selected from the group consisting of —C(O)O(C$_1$–C$_{10}$ alkyl), C$_1$–C$_{10}$ alkoxy, C$_1$–C$_{10}$ alkanoyl, halo, nitro, cyano, 5 to 10 membered heterocycle, C$_6$–C$_{10}$ aryl, C$_1$–C$_{10}$ alkyl, —NR$^2$R$^3$, —S(O)$_n$(C$_1$–C$_{10}$ alkyl) wherein n is an integer ranging from 0 to 2, and SO$_2$NR$^2$R$^3$; and wherein one or two carbons in the alkyl portion of said alkyl, alkoxy, or alkanoyl groups may be optionally replaced by a heteroatom selected from O, S, and NR$^2$;

with a compound of formula,

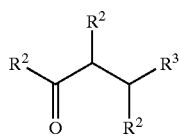

in an alcoholic solvent under acidic conditions.
wherein:

R$^2$ and R$^3$ are defined as above, the reaction is monitored for the formation of the intermediate of formula 11 at which point a compound of formula 10 is added.

48. The process according to claim 47 wherein the alcohol is selected from the group consisting of methanol, ethanol, isopropanol and tert-butanol.

49. The process according to claim 48 wherein the acid is selected from acetic and formic acid.

50. The process according to claim 47 wherein the acid is acetic acid and the solvent is ethanol.

51. The process according to claim 10 wherein a compound of formula 12 is prepared by the reaction of a compound of formula (20)

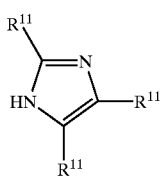

as its free base or acid addition salt wherein:

each R$^{11}$ is independently selected from the group consisting of H, —C(O)O(C$_1$–C$_{10}$ alkyl), C$_1$–C$_{10}$ alkoxy, C$_1$–C$_{10}$ alkanoyl, halo, nitro, cyano, 5 to 10 membered heterocycle, C$_6$–C$_{10}$ aryl, C$_1$–C$_{10}$ alkyl, —NR$^2$R$^3$, —S(O)$_n$(C$_1$–C$_{10}$ alkyl) wherein n is an integer ranging from 0 to 2, and SO$_2$NR$^2$R$^3$; wherein said aryl and heterocycle groups are optionally replaced by 1 to 3 substituents independently selected from the group consisting of —C(O)O(C$_1$–C$_{10}$ alkyl), C$_1$–C$_{10}$ alkoxy, C$_1$–C$_{10}$ alkanoyl, halo, nitro, cyano, 5 to 10 membered heterocycle, C$_6$–C$_{10}$ aryl, C$_1$–C$_{10}$ alkyl, —NR$^2$R$^3$, —S(O)$_n$(C$_1$–C$_{10}$ alkyl) wherein n is an integer ranging from 0 to 2, and SO$_2$NR$^2$R$^3$; and wherein one or two carbons in the alkyl portion of said alkyl, alkoxy, or alkanoyl groups may be optionally replaced by a heteroatom selected from O, S, and NR$^2$;

with a compound of formula

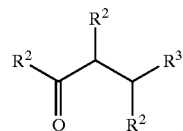

wherein:

R$^2$ and R$^3$ are defined as above, and a compound of formula 10 under acidic conditions.

52. The process according to claim 51 wherein the solvent is selected from the group consisting of acetic acid, formic acid, dichloromethane, dichloroethane, tetrachloroethane, and tetrahydrofuran.

53. The process according to claim 51 wherein the acid is selected from the group consisting of acetic and formic acid.

54. The process according to claim 5 wherein a compound of formula 13 is prepared by reacting a compound of formula 17 with a reagent of the formula

wherein R$^5$ is defined above, as its acid addition salt in polar solvents with or without added base at a temperature between about 40° C. to 150° C.

55. The process according to claim 54 wherein said polar solvents are selected from the group consisting of methanol, ethanol, isopropanol, tert-butanol, dimethylformamide, N-methylpyrrolidinone, acetonitrile, dimethylacetamide, and dimethylsulfoxide and said base is chosen from the group consisting of pyridine, 2,6-lutidine, imidazole, amine bases, or dimethylaminopyridine.

56. The process according to claim 54 wherein the compound of formula H$_2$NOR$^5$ is methoxylamine hydrochloride.

57. The process according to claim 56 wherein the reaction is run in isopropanol.

58. The process according to claim 54 wherein compound 17 is prepared by the reaction of a compound of the formula 1 with a carbonyl source and base in an inert solvent followed by reaction of a compound of formula (16).

59. The process according to claim 58 wherein the carbonyl source is selected from the group consisting of carbonyldiimidazole (CDI), phosgene, triphosgene, carbonyl bisbenzotriazole, carbonyl bishydroxybenzotriazole, and carbonyl bis-1,2,4-triazole.

60. The process according to claim 58 wherein the base is selected from the group consisting of 1,8-diazabicylco [5.4.0] undec-7-ene (DBU), 1,2-dimethyl-1,4,5,6-tetrahydropyrimidine, sodium hexamethyl disilazane, lithium diisopropylamide, potassium hexamethyl diisilazane, ortetramethyl guanidine in an inert solvent selected from the group consisting of isopropylether, dimethylformamide, N-methylpyrrolidinone, acetonitrile, dimethylacetamide, tetrahydrofuran, dimethylsulfoxide, dioxane, dimethoxyethane, dichloromethane, tetrachloroethane, and dichloroethane.

61. The process according to claim 58 wherein said reaction is monitored for the formation of an intermediate of formula 5.

62. The process according to claim 61 wherein once intermediate 5 is formed, a compound of formula 16 is added at a temperature between about 0° C. to 150° C.

63. The process according to claim 62 wherein the reaction is run in acetonitrile at reflux.

64. The process according to claim 40 wherein a compound of formula

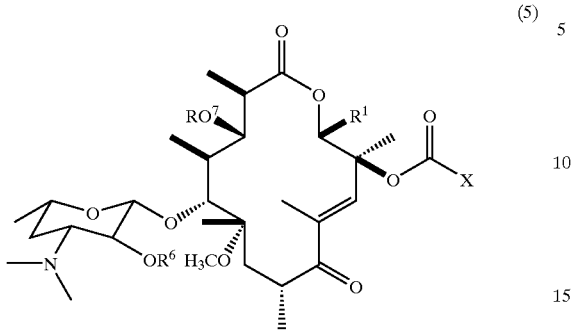

(5)

wherein:
- $R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from the consisting of hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or
- $R^1$ is phenyl which may be optionally replaced with one to three groups independently selected from $C_1$–$C_4$ alkyl, $C_1$–$C_4$ alkoxy and $C_1$–$C_4$ alkylthio groups, halogen atoms, hydroxyl groups, trifluoromethyl, and cyano; or
- $R^1$ is formula (a)

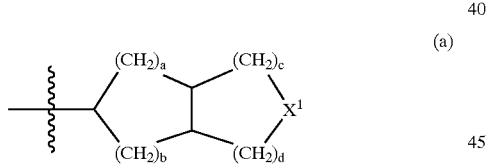

(a)

wherein $X^1$ is O, S or —$CH_2$—, a, b, c, and d are each independently selected from an integer ranging from 0 to 2 and a+b+c+d≦5; or $R^1$ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either of which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, phenyl $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and

- each $R^4$ is independently $C_6$–$C_{10}$ aryl or 5 to 10 membered heterocycle, wherein said aryl and heterocycle groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n(C_1$–$C_{10}$ alkyl) wherein n is an integer ranging from 0 to 2, and $SO_2NR^2R^3$; and
- $R^6$ is H, —$C(O)R^4$, or $C_1$–$C_{18}$ alkanoyl, wherein one or two carbons in the alkyl portion of said alkanoyl may be optionally replaced by a heteroatom selected from the group consisting of O, S, and $NR^2$; and
- $R^7$ is a radical of formula

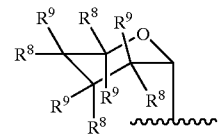

wherein each $R^8$ and $R^9$ are independently hydrogen, hydroxy, $C_1$–$C_6$ alkoxy, —$OC(O)R^4$, —$OC(O)NHNH_2$, —$OSi(R^{10})_3$, or $C_1$–$C_{18}$ O-alkanoyl, wherein one or two carbons in the alkyl portion of said alkanoyl may be optionally replaced by a heteroatom selected from the group consisting of O, S, and $NR^2$; and
- $R^8$ & $R^9$ may be taken together to form

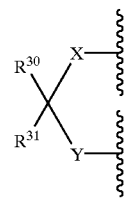

wherein:
  X=O or S
  Y=O or S
  $R^{30}$, and $R^{31}$=H, $C_1$–$C_6$ alkyl, $C_6$–$C_{10}$ aryl, or $R^{30}$ and $R^{31}$ taken together form =O or =S
  or $R^8$ & $R^9$ can be taken together to form

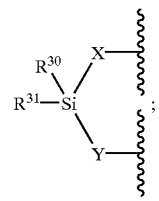

and each $R^{10}$ is independently $C_1$–$C_{10}$ alkyl or $C_6$–$C_{10}$ aryl, and
- X is imidazole, 1,2,4-triazole, hydroxybenzotriazole, or benzotriazole;

123 is prepared by the reaction of a compound of the formula

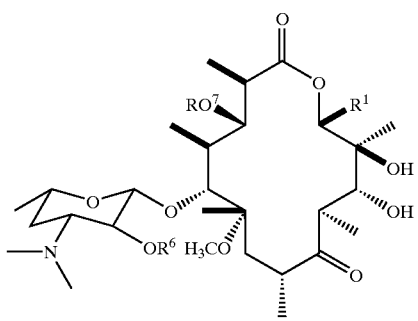

(1)

with a carbonyl source and a base in an inert solvent wherein in formula (1):

$R^1$ is an alpha-branched $C_3$–$C_8$ alkyl, alkenyl, alkynyl, alkoxyalkyl or alkylthioalkyl group any of which may optionally be substituted by one to three hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one to three groups independently selected from hydroxy, $C_1$–$C_4$ alkyl, and halo; or a 3 to 6 membered oxygen or sulphur containing heterocyclic ring which may be saturated, or fully or partially unsaturated and which may optionally be substituted by one to three $C_1$–$C_4$ alkyl groups or halo atoms; or $R^1$ is phenyl which may be optionally replaced with one to three groups independently selected from $C_1$–$C_4$ alkyl, $C_1$–$C_4$ alkoxy and $C_1$–$C_4$ alkylthio groups, halogen atoms, hydroxyl groups, trifluoromethyl, and cyano; or $R^1$ can be a formula (a) as shown below

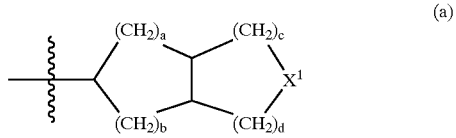

(a)

wherein $X^1$ is O, S or —$CH_2$—, a, b, c, and d are each independently selected from an integer ranging from 0 to 2 and a+b+c+d≦5; or $R^1$ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl, alkylthio or alkoxy group wherein any of said alkyl, alkoxy, alkenyl or alkynyl groups may be substituted by one to three hydroxyl groups or by one to three halo atoms; or a $C_3$–$C_8$cycloalkyl or $C_5$–$C_8$cycloalkenyl either or which may be optionally replaced by methyl or one to three $C_1$–$C_4$alkyl groups or halo atoms; or a 3 to 6 membered oxygen or sulphur containing heterocyclic ring which may be saturated or fully or partially unsaturated and which may optionally be substituted by one to three $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one to three $C_1$–$C_4$alkyl groups or halo atoms; and

124 each $R^4$ is independently $C_6$–$C_{10}$ aryl or 5 to 10 membered heterocycle, wherein said aryl and heterocycle groups are optionally replaced by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 5 to 10 membered heterocycle, $C_6$–$C_{10}$ aryl, $C_1$–$C_{10}$ alkyl, —$NR^2R^3$, —$S(O)_n$($C_1$–$C_{10}$ alkyl) wherein n is an integer ranging from 0 to 2, and $SO_2NR^2R^3$; and $R^6$ is H, —$C(O)R^4$, or $C_1$–$C_{18}$ alkanoyl, wherein one or two carbons in the alkyl portion of said alkanoyl may be optionally replaced by a heteroatom selected from the group consisting of O, S, and $NR^2$; and $R^7$ is a radical of formula

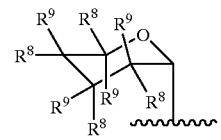

wherein each $R^8$ and $R^9$ are independently hydrogen, hydroxy, $C_1$–$C_6$ alkoxy, —$OC(O)R^4$, —$OC(O)NHNH_2$, —$OSi(R^{10})_3$, or $C_1$–$C_{18}$ O-alkanoyl, wherein one or two carbons in the alkyl portion of said alkanoyl may be optionally replaced by a heteroatom selected from the group consisting of O, S, and $NR^2$; and $R^8$ & $R^9$ may be taken together to form

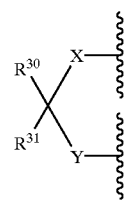

wherein:

X=O or S

Y=O or S $R^{30}$, and $R^{31}$=H, $C_1$–$C_6$ alkyl, $C_6$–$C_{10}$ aryl, or $R^{30}$ and $R^{31}$ taken together form =O or =S or $R^8$ & $R^9$ can be taken together to form

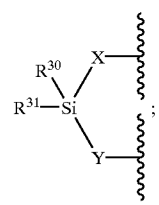

and each $R^{10}$ is independently $C_1$–$C_{10}$ alkyl or $C_6$–$C_{10}$ aryl.

65. The process according to claim 64 wherein the carbonyl source is selected from the group consisting of carbonyldiimidazole (CDI), phosgene, triphosgene, carbonyl bisbenzotriazole, carbonyl bishydroxybenzotriazole, and carbonyl bis-1,2,4-triazole.

66. The process according to claim 64 wherein the base is selected from the group consisting of 1,8-diazabicylco[5.4.0] undec-7-ene (DBU), 1,2-dimethyl-1,4,5,6-tetrahydro-pyrimidine, sodium hexamethyl disilazane, lithium diisopropylamide, potassium hexamethyl diisilazane, and tetramethyl guanidine in an inert solvents selected from the group consisting of isopropylether, dimethylformamide, N-methylpyrrolidinone, acetonitrile, dimethylacetamide, tetrahydrofuran, dimethylsulfoxide, dioxane, dimethoxyethane, dichloromethane, tetrachloroethane, and dichloroethane.

* * * * *